(12) United States Patent
Bonnette et al.

(10) Patent No.: US 7,226,433 B2
(45) Date of Patent: Jun. 5, 2007

(54) THROMBECTOMY CATHETER DEVICE HAVING A SELF-SEALING HEMOSTASIS VALVE

(75) Inventors: Michael John Bonnette, Minneapolis, MN (US); John Christopher Riles, Minneapolis, MN (US); Mark Alfred Hilse, Ham Lake, MN (US); Eric Joel Thor, Arden Hills, MN (US); Marvin Harris York, Richfield, MN (US)

(73) Assignee: Possis Medical, Inc., Minneapolis, MN (US)

( * ) Notice: Subject to any disclaimer, the term of this patent is extended or adjusted under 35 U.S.C. 154(b) by 309 days.

(21) Appl. No.: 10/455,096

(22) Filed: Jun. 5, 2003

(65) Prior Publication Data

US 2004/0210194 A1 Oct. 21, 2004

Related U.S. Application Data

(60) Continuation-in-part of application No. 10/198,264, filed on Jul. 16, 2002, now Pat. No. 6,875,193, which is a continuation-in-part of application No. 09/888,455, filed on Jun. 25, 2001, now Pat. No. 6,755,803, which is a continuation-in-part of application No. 09/356,783, filed on Jul. 16, 1999, now abandoned, which is a division of application No. 09/019,728, filed on Feb. 6, 1998, now Pat. No. 5,989,210.

(51) Int. Cl.
*A61M 25/00* (2006.01)

(52) U.S. Cl. .................. 604/164.01; 604/247; 604/264

(58) Field of Classification Search ................ 604/500, 604/506–510, 164.01–170.03, 264, 246, 604/247, 256, 523, 533, 537, 284, 158–163; 606/167; 251/229, 251, 340

See application file for complete search history.

(56) References Cited

U.S. PATENT DOCUMENTS

| | | | | |
|---|---|---|---|---|
| 5,989,210 A | * | 11/1999 | Morris et al. | 604/22 |
| 6,024,729 A | * | 2/2000 | Dehdashtian et al. | 604/256 |
| 6,063,069 A | * | 5/2000 | Cragg et al. | 604/508 |
| 6,287,280 B1 | * | 9/2001 | Lampropoulos et al. | 604/167.03 |
| 6,331,176 B1 | * | 12/2001 | Becker et al. | 604/533 |
| 2003/0127620 A1 | * | 7/2003 | Houde | 251/229 |
| 2004/0068248 A1 | * | 4/2004 | Mooney et al. | 604/500 |

* cited by examiner

*Primary Examiner*—Nicholas D. Lucchesi
*Assistant Examiner*—Melissa A. McCorkle
(74) *Attorney, Agent, or Firm*—Hugh D. Jaeger, Esq.

(57) ABSTRACT

A thrombectomy catheter device having an improved hemostasis valve which is self-sealing and which functions as a one-way valve. The self-sealing hemostasis valve can be factory preset to automatically seal with or without the inclusion of a guidewire at a certain desired pressure or allowable leakage. Such sealing is automatic without the need to manually manipulate a hemostasis nut to obtain hemostasis. The thrombectomy catheter device can, without hemostasis nut adjustment, be positioned along and about a guidewire while yet maintaining suitable pressure for sustaining hemostasis at a preferred level. Certain embodiments of the thrombectomy catheter device having a self-sealing hemostasis valve include an adjustable hemostasis nut which can be manually tightened to restrict flow or guidewire movement or loosened to reduce friction on the guidewire and allow fluid to flow out if desired. An introducer facilitates free passage of a guidewire in either direction through the hemostasis nut and hemostasis valving and can also be incorporated to purge internal air or fluids.

48 Claims, 48 Drawing Sheets

THROMBECTOMY CATHETER DEVICE HAVING A SELF-SEALING HEMOSTASIS VALVE

CROSS REFERENCES TO RELATED APPLICATIONS

This patent application is a continuation-in-part of Ser. No. 10/198,264 entitled "Rapid Exchange Fluid Jet Thrombectomy Device and Method" filed on Jul. 16, 2002, now U.S. Pat. No. 6,875,193, which is a continuation-in-part of Ser. No. 09/888,455 entitled "Single Operator Exchange Fluid Jet Thrombectomy Device" filed on Jun. 25, 2001, now U.S. Pat. No. 6,755,803, which is a continuation-in-part of Ser. No. 09/356,783 entitled "Rheolytic Thrombectomy Catheter and Method of Using Same" filed on Jul. 16, 1999, now abandoned, which is a divisional of Ser. No. 09/019,728 entitled "Rheolytic Thrombectomy Catheter and Method of Using Same" filed on Feb. 6, 1998, now U.S. Pat. No. 5,989,210. Patent application Serial No. 10/198,264 is also related to Ser. No. 09/417,395 entitled "Thrombectomy Catheter and System" (as amended) filed on Oct. 13, 1999, now U.S. Pat. No. 6,676,627, which is a continuation-in-part of Ser. No. 08/349,665 entitled "Thrombectomy Method" filed on Dec. 5, 1994, now U.S. Pat. No. 6,558,366, which is a divisional of Ser. No. 08/006,076 entitled "Thrombectomy Device" filed on Jan. 15, 1993, now U.S. Pat. No. 5,370,609, which is a continuation of Ser. No. 07/563,313 entitled "Thrombectomy Device and Method" filed on Aug. 6, 1990, abandoned. Patent application Ser. No. 10/198,264 is also related to Ser. No. 08/351,605 entitled "Thrombectomy and Tissue Removal Method and Device" filed on Dec. 8, 1994, now U.S. Pat. No. 6,471,683, which is a divisional of Ser. No. 07/976,367 entitled "Thrombectomy and Tissue Removal Method and Device" filed on Nov. 13, 1992, abandoned, which is a continuation-in-part of Ser. No. 07/563,313 entitled "Thrombectomy Device and Method" filed on Aug. 6, 1990, abandoned.

BACKGROUND OF THE INVENTION

1. Field of the Invention

The present invention relates to a thrombectomy catheter device in general, and more particularly, to a thrombectomy catheter device having a self-sealing hemostasis valve.

2. Description of the Prior Art

In current interventional thrombotic material removal procedures using thrombosis removal catheter devices, a guidewire is loaded into the tip of a thrombectomy catheter device, through the exhaust tube, through a seal, and out the hemostasis nut where the guidewire was most likely previously positioned within a patient using common interventional means. The hemostasis valve is then manually tightened by way of a hemostasis nut, which normally compresses a silicone ring or seal until it "flattens" to close off the inner diameter of the seal, thereby effecting a seal around and about the guidewire shaft. This seal is activated to keep blood, saline solution, and other fluids carrying debris from leaking out of the device during operation, which fluids carrying debris are normally exhausted out of the device via an exhaust line and collected in an exhaust bag. The seal further keeps blood from leaking out of the patient while the device is not in operation, but still within the patient. During a thrombectomy procedure, it is desirable to move the catheter device over the guidewire without moving the guidewire, while maintaining hemostasis via common interventional practices. The current hemostasis valve on the manifold, although adequate, is not optimized. It is difficult to move the device without moving the guidewire due to the nature of a compressive seal. If movement is improved by loosening the hemostasis nut, then leakage becomes an issue. It is also time-consuming and problematic to have to always manually tighten a hemostasis nut to achieve hemostasis. For example, the physician must remember an extra step to obtain hemostasis, in which the hemostasis nut may be loosened instead of tightened. This loosening then sometimes leads to the hemostasis nut becoming detached from the manifold, which then leads to the inability to obtain hemostasis. The other main issue is "fine tuning" the tightness of the nut to obtain the proper device movement over the guidewire (i.e., no guidewire movement). This often leads to some amount of leakage.

SUMMARY OF THE INVENTION

The general purpose of the present invention is to provide a thrombectomy catheter device having an improved and self-sealing hemostasis valve which can be preset to automatically seal with or without the inclusion of a guidewire at a certain desired pressure. Such sealing is automatic without the need to manually manipulate a hemostasis nut to obtain hemostasis. The thrombectomy catheter device can, without hemostasis nut adjustment, be positioned along and about a guidewire while yet maintaining suitable pressure or at an allowable leakage rate for sustaining hemostasis at a preferred level. Additionally, the hemostasis nut in several embodiments can be manually tightened to influence the self-sealing hemostasis valve to restrict flow or guidewire movement, or manually loosened to reduce friction on the guidewire and allow fluid to flow out, if desired. The present invention is a mechanical thrombectomy catheter device which uses high velocity saline jets shooting past a gap to entrain and macerate thrombus and other debris located within vessels by way of a low pressure zone and recirculation patterns, as described in previous patents and/or patent applications by the applicants. This basic design is further optimized using cross stream technology that has regions of inflow (low pressure) and outflow (high pressure) that maximize the recirculation pattern, among other things. The thrombectomy catheter device is primarily composed of a manifold and an exhaust line having a maceration tip which associates with and connects to commonly found thrombectomy removal systems such as, but not limited to, a pump, a high pressure supply line, and a drive unit. A cross stream effect occurs at the tip, which is described extensively in previous patents and applications by the applicants along with all of the other components. This particular improvement to this existing technology is concerned with the manifold of the device. The manifold allows for the connection of the high pressure supply line and an exhaust line, and includes structure for exiting of a guidewire which is sealed with a self-sealing hemostasis valve. The new improvement to the manifold is concerned primarily with the self-sealing hemostasis valve, although the current manifold is also improved over the old in such ways as being optimized for size, weight, manufacture, and compatibility with future improvements to the overall thrombectomy catheter system.

The preferred design of an improved self-sealing hemostasis valve for cross stream thrombectomy or other catheter devices, and related designs, is one in which the self-sealing hemostasis valve can be factory preset or manufactured to seal at a certain pressure or to maintain an allowable leakage. Presetting the self-sealing hemostasis valve allows the user to use the thrombectomy catheter devices without needing to manipulate a hemostasis nut on a conventional valve to obtain hemostasis. In this way, the seal is automatic or self-sealing. The self-sealing hemostasis valve will also seal at a preset pressure or allowable leakage factor with or without the guidewire in place. Catheters are usually primed where the tip is inserted in a bowl of saline and where the catheter is operated to remove air and fill the effluent line without the guidewire in place. The prior art designs required the hemostasis nut to be manually tightened to eliminate leakage out the manifold. In many instances, it is easy to forget this, and fluid would leak out and the hemostasis nut would need to be tightened to achieve stasis. The new self-sealing hemostasis valve overcomes the inadequacies of the prior art and is automatic and, therefore, more foolproof and easier to use, as fluid may be expelled therefrom by merely taking advantage of the new design in that the valve is also one-way directional flow. Air and fluid can be pushed out the back of the self-sealing hemostasis valve without repositioning the hemostasis nut, but none can be pulled in. This improves safety of the device since air cannot be pulled in under negative pressure circumstances which could lead to air embolization if the user tried to inject fluid, such as contrast fluid, through the manifold. Under normal usage conditions, the guidewire will travel through the self-sealing hemostasis valve without any additional manipulation. If the guidewire will not pass through the self-sealing hemostasis valve easily, as it would be with smaller diameter guidewires, then an introducer can be inserted to fully open the self-sealing hemostasis valve to aid in passage of the guidewire through the manifold, and the introducer can then be pulled out or retracted to create the seal. The introducer can be pushed through the self-sealing hemostasis valve in those embodiments incorporating adjustable hemostasis nuts where the hemostasis nut is fully open to disengage the automatic sealing feature about the guidewire to aid guidewire movement through the self-sealing hemostasis valve or to bleed out air/fluid. Alternatively, in embodiments not having an adjustable hemostasis nut, the introducer can be positioned to engage and open the self-sealing hemostasis valve to disengage the automatic sealing feature about the guidewire to aid guidewire movement through the self-sealing hemostasis valve or to bleed out air/fluid. If hemostasis is not achieved after these operations, then the hemostasis nut where adjustable can be tightened down to effect a seal. The other feature of this design is that the valve can be used as a regular hemostasis valve in that it can be tightened to restrict flow or guidewire movement more, or loosened to reduce friction on the guidewire and allow fluid to flow out, if desired. Another advantage of this design is that it eliminates components from previous similar designs (i.e., it is more manufacturable and has lower cost).

Alternate embodiments of the invention also address the issues of guidewire movement, adequate hemostasis, and manual sealing by way of a pliable self-sealing hemostasis valve that is designed much like a biological valve. The entire hemostasis features of the manifolds are composed of components that fit into an appropriately designed cavity in the manifold, a hemostasis nut that screws or otherwise affixes onto the manifold, and an introducer which engages into the hemostasis nut. In a first alternate embodiment, the first component inserted into the manifold is a dual seal, then a washer, then the self-sealing hemostasis valve, then another washer; then the hemostasis nut is snapped on or otherwise affixed and then screwed on as applicable. An introducer is then snapped into or otherwise engaged with the hemostasis nut. For most functions and in all the embodiments, the self-sealing hemostasis valve incorporated in the instant invention is the primary means incorporated for slidable engagement with the guidewire and for sealing engagement with the surrounding cavity in a manner similar to that of the preferred embodiment. In the first alternate embodiment, the dual seal acts as a normal compressive seal when the hemostasis nut is tightened down, as in most hemostasis valves. This secondary dual seal is only used in extreme cases when hemostasis cannot be achieved with the automatic self-sealing hemostasis valve. The washers aid in transferring force evenly and minimize seals or valves binding on each other when the hemostasis nut is tightened. The introducer is only used to aid guidewire movement through the seals or to bleed air out of the manifold. The introducer can be pushed through the self-sealing hemostasis valve while the hemostasis nut is fully open to disengage the automatic sealing feature to aid guidewire movement through this self-sealing hemostasis valve or to bleed out air/fluid. Under normal usage conditions, the guidewire will travel through the self-sealing hemostasis valve and achieve hemostasis without any additional manipulation of the assembly. If the guidewire will not pass through the self-sealing hemostasis valve easily, as it would be the case with smaller diameter guidewires, then the introducer can be pushed to fully open the self-sealing hemostasis valve to aid in passage of the guidewire through the manifold, and can then be pulled out to create the seal. If hemostasis is not achieved with these operations, then the hemostasis nut can be tightened down to engage the secondary seal.

According to the first embodiment of the present invention, there is provided a thrombectomy catheter device having a self-sealing hemostasis valve. The thrombectomy catheter device having a self-sealing hemostasis valve includes a centrally located manifold to which a variety of components attach and which are outwardly visible, and also includes features which are seen in exploded and cross sectional views. The manifold includes mutually connected interior passageways, some of which are of configured shape, which are located within a centrally located tubular body of the manifold or in branches of the manifold and which are available for attachment to other components of the instant invention by threaded surfaces located about the manifold. Located at one end of the manifold is a cavity body and a contained cavity for housing of a self-sealing hemostasis valve and an elongated washer. A hemostasis nut having an internal annular ring snappingly engages another annular ring at the proximal region of the manifold cavity body to be loosely connected to the manifold and to be available for threaded engagement thereto. A cylindrical boss is located interiorly of the hemostasis nut to impinge and to apply pressure to the self-sealing hemostasis valve and the elongated washer whereby the shape and other attributes of the self-sealing hemostasis valve may be influenced to achieve various states or stages of hemostasis. Some other items attached to or which are useful to the operation of the instant invention include Luer connectors, a strain relief, a catheter tube, a high pressure tube, a fluid jet emanator, a catheter tube tip, radiopaque markers, inflow and outflow orifices, a ferrule, a threaded high pressure connection port, and an introducer.

The first alternate embodiment of the instant invention includes a manifold having an alternately shaped cavity within the cavity body which receives a dual seal, a wide washer, a self-sealing hemostasis valve, and another washer.

Sealing to a guidewire is automatic where the self-sealing hemostasis valve is the primary method of sealment to effect hemostasis or, if desired, a hemostasis nut may be incorporated to alternately effect a seal between the dual seal and a guidewire, as well as a seal between the dual seal and the interior of the manifold. An introducer is also provided to aid in alternate accommodation of a guidewire and to provide for venting for the interior of the manifold.

A second alternate embodiment of the instant invention includes a manifold having a cavity within the cavity body which receives a self-sealing hemostasis valve, a washer and one end of an introducer. A nonadjustable hemostasis nut threadingly affixes to the proximal region of the manifold where a stop means determines the position of the hemostasis nut along the proximal region of the manifold. Such positioning advances a cylindrical boss residing in the hemostasis nut into contact with a self-sealing hemostasis valve. As in other embodiments, sealing to a guidewire is automatic where the self-sealing hemostasis valve is the primary method of sealment to effect hemostasis. A seal is also effected between the self-sealing hemostasis valve and the interior of the manifold. An introducer is also provided to aid in alternate accommodation of a guidewire and to provide for venting for the interior of the manifold. A cavity extension adjacent to the cavity accommodates the distal end of an affixed introducer when the introducer is optionally positioned distally to accommodate a guidewire or when the introducer is positioned distally to allow the release of air or fluid from the interior of the manifold or other catheter components.

A third alternate embodiment of the instant invention embraces the teaching of the second alternate embodiment whereby a cavity insert is included in a reconfigured and expanded length cavity in the manifold where the cavity extension of the second alternative embodiment is removed and a cavity insert is utilized in the expanded length cavity. The cavity insert includes a recess corresponding in size to that of the removed cavity extension to accommodate the distal end of an affixed introducer when the introducer is optionally positioned distally to accommodate a guidewire or when the introducer is positioned distally to allow the release of air or fluid from the interior of the manifold or other catheter components.

A fourth alternate embodiment of the instant invention embraces the teaching of the second alternate embodiment whereby the threads at the proximal region of the cavity body are replaced by a smooth cylindrical surface and the internal threads of the hemostasis nut are replaced by a smooth cylindrical surface. The smooth cylindrical surfaces of the proximal region of the cavity body and the smooth cylindrical surfaces of the hemostasis nut mutually accommodate each other and are bonded such as by adhesive or other suitable methods to affix the hemostasis nut to the distal region of the cavity body.

A fifth alternate embodiment of the instant invention includes a manifold having a cavity within the cavity body which receives a self-sealing hemostasis valve, a washer and one end of an introducer. A nonadjustable hemostasis nut threadingly affixes to the proximal region of the manifold where a stop means determines the position of the hemostasis nut along the proximal region of the manifold. Such positioning advances a cylindrical boss residing in the hemostasis nut into contact with a self-sealing hemostasis valve. As in other embodiments, sealing to a guidewire is automatic where the self-sealing hemostasis valve is the primary method of sealment to effect hemostasis. A seal is also effected between the self-sealing hemostasis valve and the interior of the manifold. An introducer is also provided to aid in alternate accommodation of a guidewire and to provide for venting for the interior of the manifold. A cavity extension adjacent to the cavity accommodates the distal end of an affixed introducer when the introducer is optionally positioned distally to accommodate a guidewire or when the introducer is positioned distally to allow the release of air or fluid from the interior of the manifold or other catheter components.

Structure of the fifth alternate embodiment is simplified and the number of components and complex structures is reduced. A streamlined flexible strain relief is furnished where one end is accommodated by a distally located flangeless tapered manifold region and is secured therein such as by adhesive or other suitable methods. A flangeless high pressure connection branch extending from the manifold accommodates a threaded high pressure connection port which secures therein by adhesive or other suitable methods.

Structure of a sixth alternate embodiment is also simplified and the number of components and complex structures is reduced, including the exclusion of a hemostasis nut. A self-sealing hemostasis valve is formed by the interference of a guidewire extending through and transmitting through an elongated hemostasis valve body having a close tolerance fit. The self-sealing hemostasis valve functions in either an active or a passive mode.

One significant aspect and feature of the present invention is a thrombectomy catheter device having a self-sealing hemostasis valve.

Another significant aspect and feature of the present invention is a thrombectomy catheter device which automatically slidingly engages and seals to a guidewire passing therethrough and does not require adjustment of a hemostasis nut.

Yet another significant aspect and feature of the present invention is a thrombectomy catheter device having a self-sealing hemostasis valve which seals to a proximally located manifold cavity wall.

A further significant aspect and feature of the present invention is a thrombectomy catheter device having a self-sealing hemostasis valve which includes opposing recessed surfaces whose central portions are radiused and increasingly thinner in a direction towards the center and which include a plurality of slits delineating a plurality of lobes to allow suitable lobe flexing, deforming and reshaping to sealingly and slidingly conform along and about the shape of a guidewire passing therethrough.

Yet another significant aspect and feature of the present invention is a thrombectomy catheter device having a self-sealing hemostasis valve which can be factory preset to maintain a desired manifold pressure with or without the inclusion of a guidewire.

Still another significant aspect and feature of the present invention is a thrombectomy catheter device having a hemostasis nut which can be utilized in addition to or in lieu of a suitable seal by the self-sealing hemostasis valve.

Still another significant aspect and feature of the present invention is a thrombectomy catheter device having a hemostasis nut which snappingly engages and remains engaged over and about the proximal region of the catheter device manifold.

Yet another significant aspect and feature of the present invention is a thrombectomy catheter device which can include the use of an introducer inserted through the hemostasis nut to assist in engagement of a guidewire in either direction.

Yet another significant aspect and feature of the present invention is a thrombectomy catheter device which can include the use of an introducer to bleed air or fluid from the manifold.

Still another significant aspect and feature of the present invention is a self-sealing hemostasis valve which limits flow to an outward direction to prevent the ingestion of foreign matter into the catheter device manifold.

Another significant aspect and feature of the present invention is a thrombectomy catheter device having a hemostasis nut which engages a stop to determine the position of the hemostasis nut along the proximal region of the manifold, thereby properly positioning a cylindrical boss against a self-sealing hemostasis valve.

Still another significant aspect and feature of the present invention is a thrombectomy catheter device having a cavity extension or cavity insert for accommodation of one end of an actuated introducer.

Still another significant aspect and feature of the present invention is a thrombectomy catheter device having a smooth cylindrical surface at the proximal region of a manifold which engages and secures to a smooth cylindrical surface interior to a hemostasis nut.

Another significant aspect and feature of the present invention is a thrombectomy catheter device having a self-sealing hemostasis valve of simplified structure including a streamlined flexible strain relief suitably attached, such as by adhesive, to the distal flangeless end of a manifold.

Another significant aspect and feature of the present invention is a thrombectomy catheter device having a self-sealing hemostasis valve of simplified structure including a flangeless high pressure connection branch extending from a manifold to accommodate a high pressure connection port secured suitably therein, such as by adhesive.

Another significant aspect and feature of the present invention is a thrombectomy catheter device having a self-sealing hemostasis valve where a self-sealing hemostasis valve is formed by the relationship of a guidewire and an elongated hemostasis valve passageway where the guidewire, which actively or passively transmits the elongated hemostasis valve passageway, offers interference within the elongated hemostasis valve passageway to form and act as a self-sealing hemostasis valve.

Having thus described embodiments of the present invention and mentioned significant aspects and features thereof, it is the principal object of the present invention to provide a thrombectomy catheter device having a self-sealing hemostasis valve.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
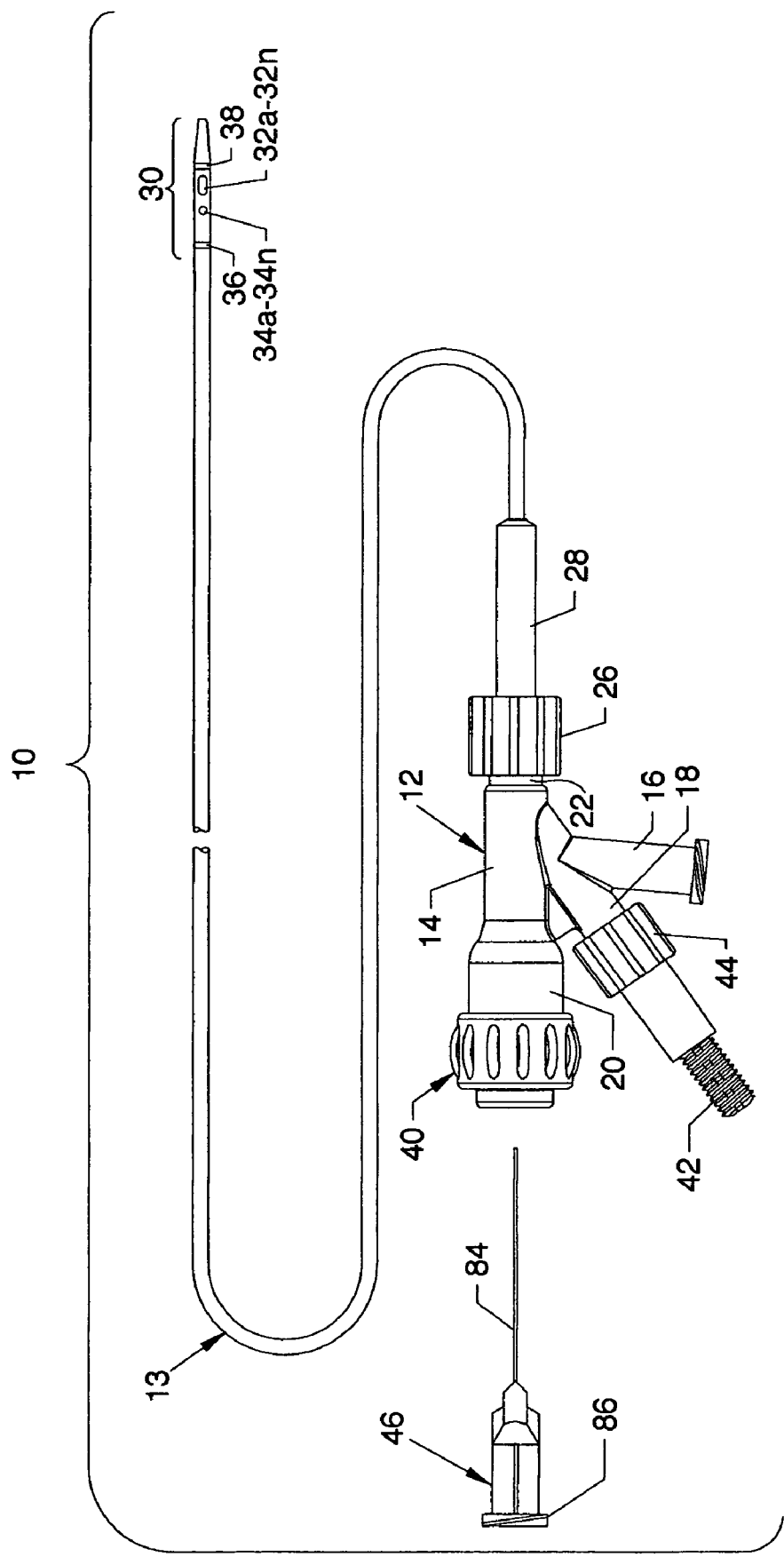
FIG. 1 is a plan view of the visible components of a thrombectomy catheter device having a self-sealing hemostasis valve, the present invention.

FIG. 1 is a plan view of the visible components of a thrombectomy catheter device having a self-sealing hemostasis valve 10, the present invention, including a one-piece manifold 12 having multiple structures extending therefrom or attached thereto and including a catheter tube 13 and other components as described herein. The visible portion of the one-piece manifold 12 includes a central tubular body 14, an exhaust branch 16 and a high pressure connection branch 18 extending angularly from the central tubular body 14, a cavity body 20 extending proximally from the central tubular body 14, and partially shown and extending distally from the central tubular body 14, a threaded connection port 22. The proximal end of the catheter tube 13 secures to the manifold 12 by the use of a Luer fitting 26 accommodated by the threaded connection port 22. The proximal end of the catheter tube 13 extends through a strain relief 28 and through the Luer fitting 26 to communicate with the manifold 12. The catheter tube 13 extends distally to a tip 30 which is tapered and which can be flexible in design. The tip 30 of the catheter tube 13 includes a plurality of inflow orifices 32a-32n and a plurality of outflow orifices 34a-34n, and radiopaque marker bands 36 and 38, all of which are disclosed and described in detail in previous patent applications and patents by the applicants. Also shown is a hemostasis nut 40 aligned to and snappingly engaged with the proximal region of the cavity body 20, and a threaded high pressure connection port 42 secured to the high pressure connection branch 18 by a Luer connector 44. An introducer 46 is also shown.

Figure 2:
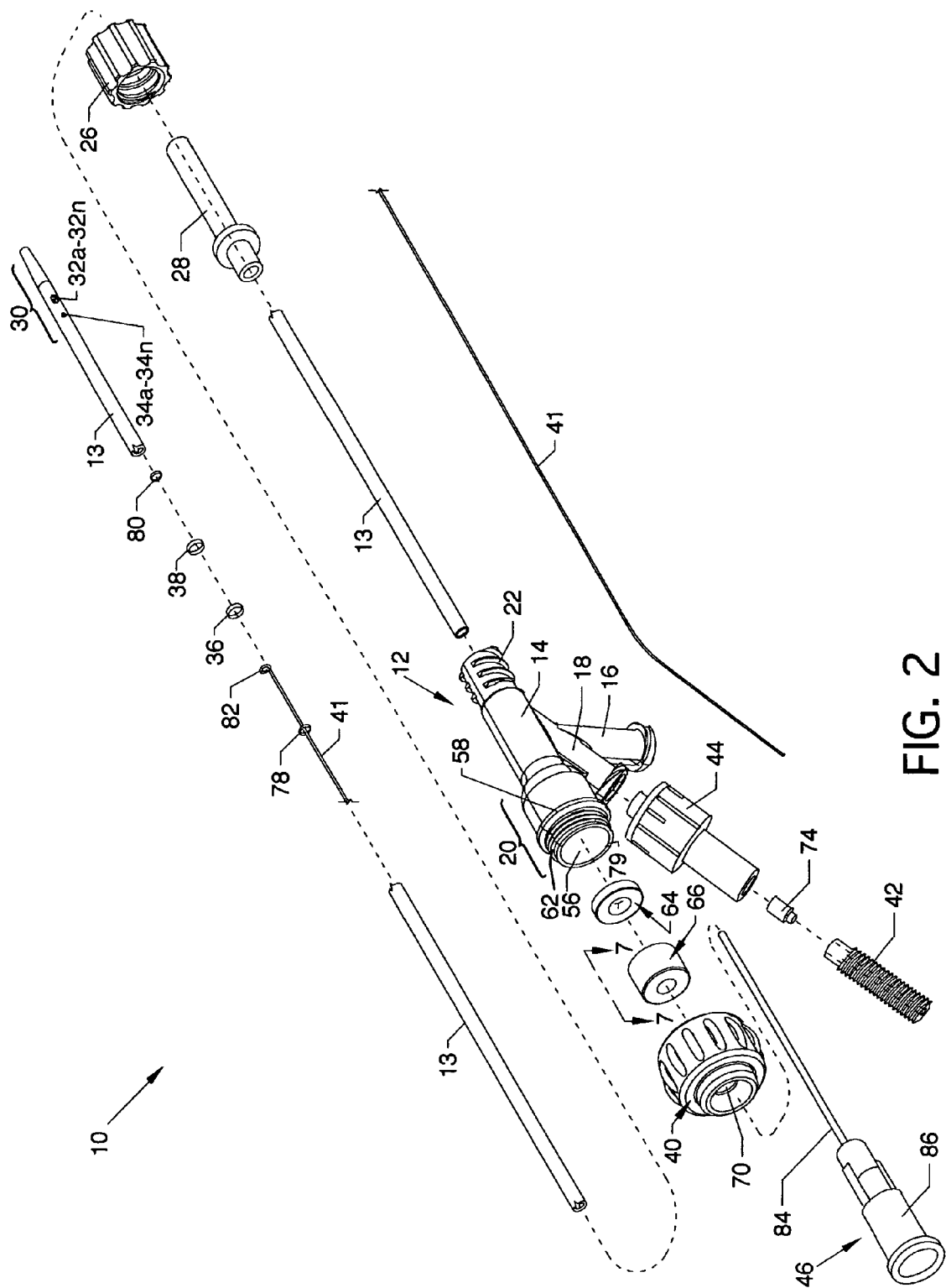
FIG. 2 is an isometric exploded view of the thrombectomy catheter device having a self-sealing hemostasis valve.
Figure 3:
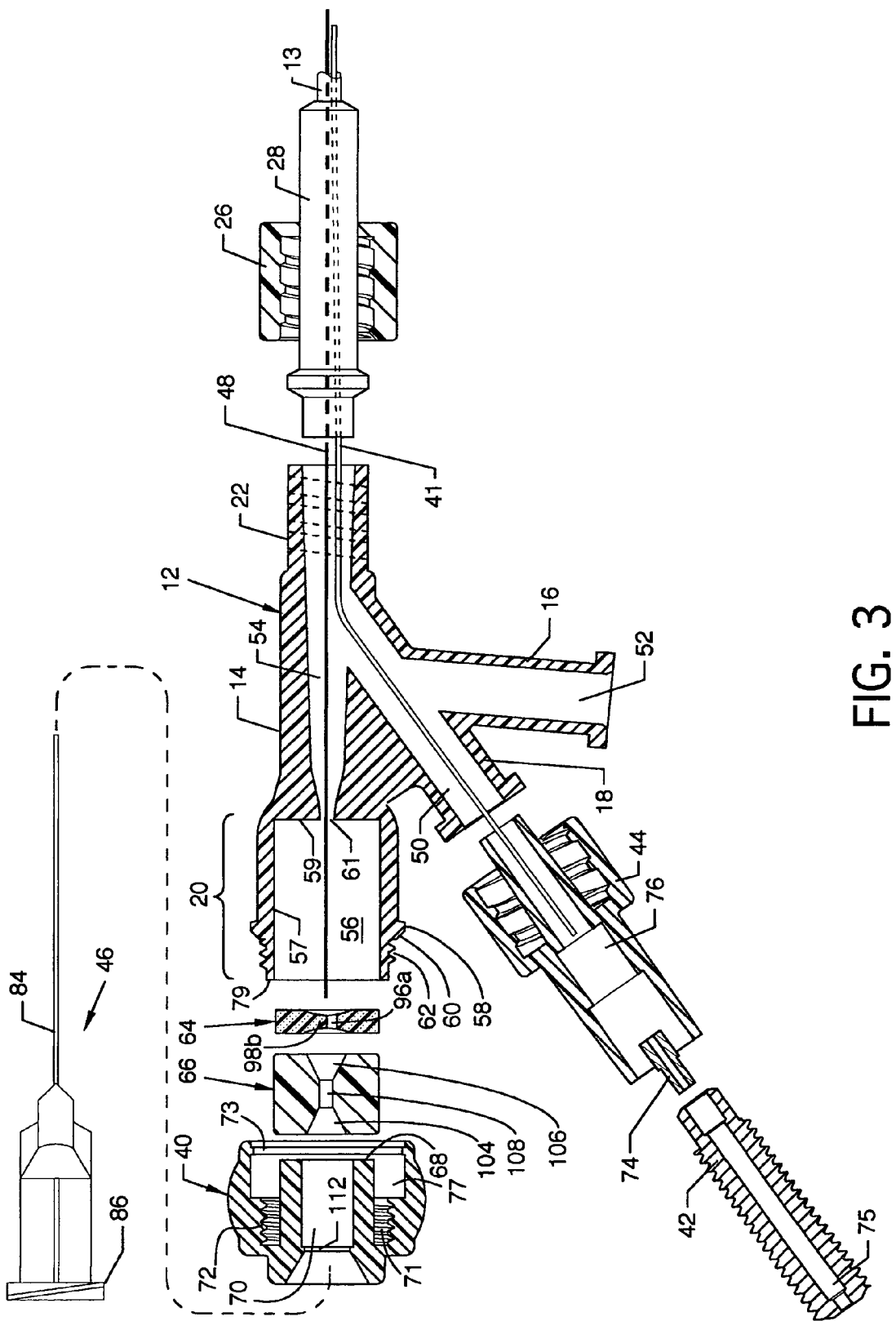
FIG. 3 is an exploded view in partial cross section of the components of the thrombectomy catheter device having a self-sealing hemostasis valve excluding the full length of the catheter tube and the included tip, but including a guidewire such as is incorporated in the use of the invention.

FIG. 2 is an isometric exploded view of the thrombectomy catheter device having a self-sealing hemostasis valve 10, the present invention, and FIG. 3 illustrates an exploded view in partial cross section of the components of the thrombectomy catheter device having a self-sealing hemostasis valve 10 excluding the full length of the catheter tube 13 and the included tip 30, but including a guidewire 48 such as is incorporated in the use of the invention. The catheter tube 13, which also serves and functions as an exhaust tube, and a high pressure tube 41 distal to the strain relief 28 are foreshortened and shown as partial lengths for the purpose of clarity.

With reference to FIG. 2 and FIG. 3, the instant invention is further described. The manifold 12 includes connected and communicating passageways and cavities (FIG. 3) including a high pressure connection branch passageway 50, an exhaust branch passageway 52, a tapered central passageway 54 extending from and through the threaded connection port 22 and through the central tubular body 14 to and communicating with a cavity 56, which preferably is cylindrical, located central to the cavity body 20. An annular ring 58 having an angled annular surface 60 is located around and about the cavity body 20 at the proximal region of the manifold 12, as well as threads 62 being proximal to the annular ring 58 and angled annular surface 60. The annular ring 58 and angled annular surface 60 provide in part for snap engagement of the hemostasis nut 40 to the manifold 12.

Figure 10:
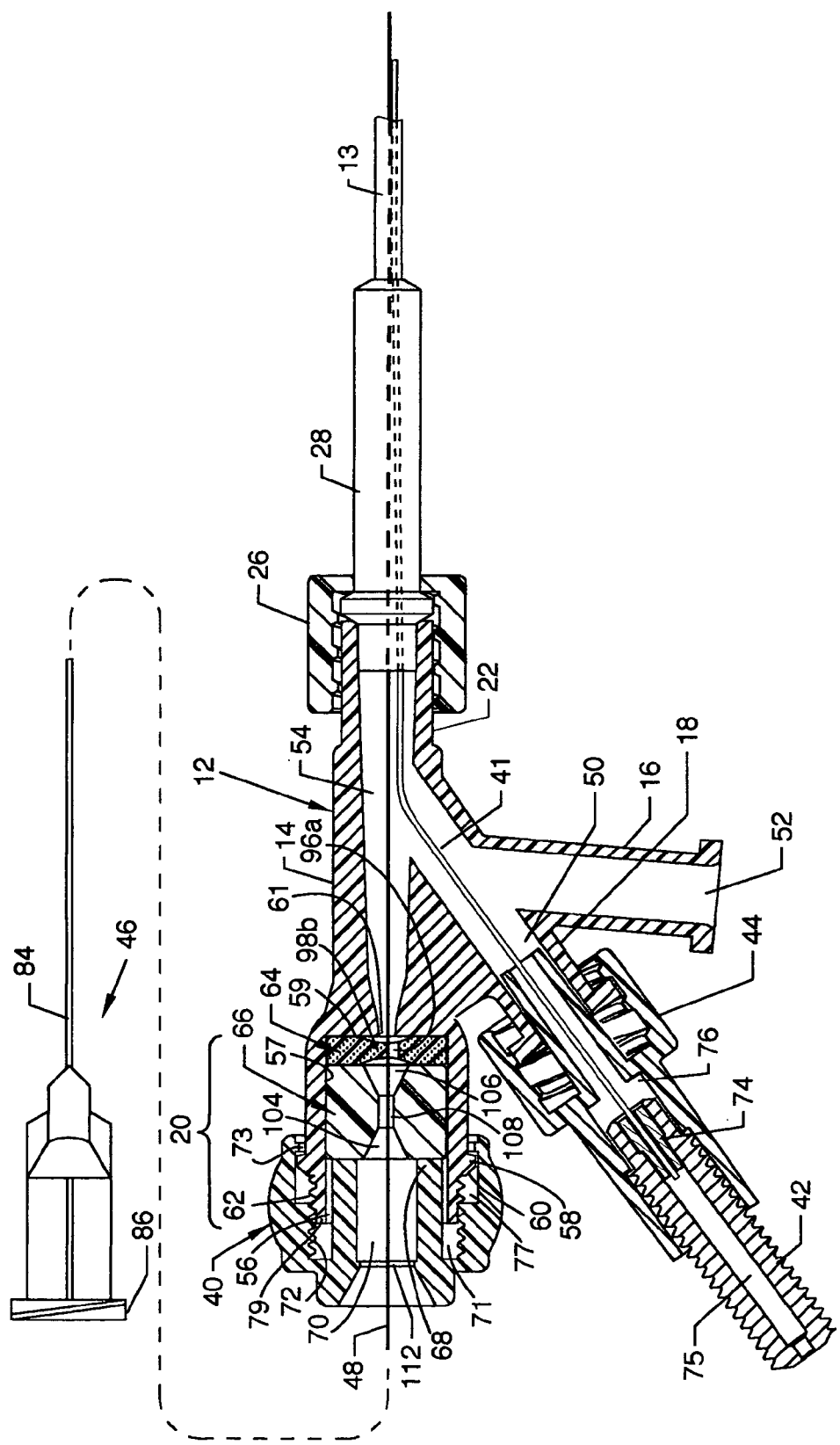
FIG. 10 is a view in partial cross section of the assembled components of FIG. 3 shown over and about and with the use of a guidewire and showing the introducer detached.
Figure 11:
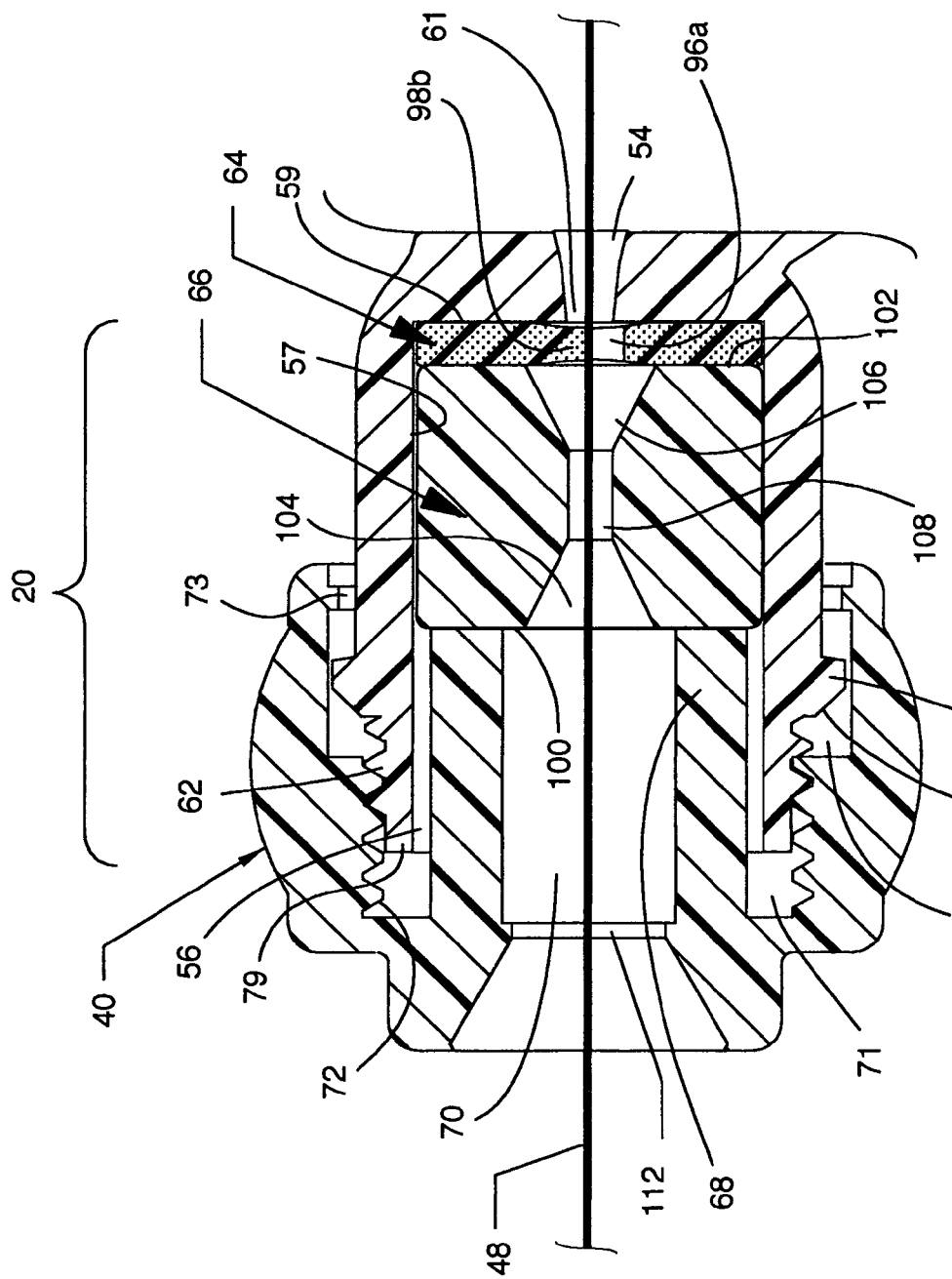
FIG. 11 is a fragmented view in cross section of the proximal region of the manifold showing the compression of the self-sealing hemostasis valve by the action of the hemostasis nut being advanced in a distal direction along the threads at the end of the cavity body of the manifold.

Beneficial to the instant invention is the use of a self-sealing hemostasis valve 64 and an elongated washer 66 located proximal to the self-sealing hemostasis valve 64, the shapes of and the functions of which are described later in detail. The self-sealing hemostasis valve 64 and the elongated washer 66 are aligned in and housed in the cavity 56 at the proximal region of the manifold 12. The cavity 56 is tubular in shape including a tubular cavity wall 57 and a planar surface 59 which is annular and circular and which intersects the tubular cavity wall 57. An orifice 61 located central to the planar surface 59 is common to the cavity 56 and the tapered central passageway 54. The hemostasis nut 40 includes a centrally located cylindrical boss 68, a beveled passageway 70 extending through and in part forming the cylindrical boss 68, and internal threads 72 distanced by a proximally located space 71 from the cylindrical boss 68. A distally located space 77 is located adjacent the proximally located space 71. The proximally located space 71 and the distally located space 77 accommodate the proximal end 79 of the manifold 12 including the threads 62 and the annular ring 58, respectively. An annular ring 73 is located distal to the internal threads 72 and the cylindrical boss 68 along and about the distal interior region of the hemostasis nut 40 for the purpose of snap engagement with and beyond the annular ring 58 of the cavity body 20. The angled annular surface 60 adjacent to the annular ring 58 facilitates snap engagement of the annular ring 58 along, beyond, and proximal to the annular ring 73 of the hemostasis nut 40. Such snap engagement (FIG. 12) loosely attaches the hemostasis nut 40 to the manifold 12 where the internal threads 72 of the hemostasis nut 40 can subsequently be made to engage the threads 62 of the manifold 12, whereby the cylindrical boss 68 is brought to bear against the elongated washer 66 to resultingly bring pressure to bear as required against the self-sealing hemostasis valve 64. Such engagements are shown in FIG. 10 and FIG. 11. The elongated washer 66 and the self-sealing hemostasis valve 64 are captured in the cavity 56 by engagement of the hemostasis nut 40 to the cavity body 20 of the manifold 12. Also included in the hemostasis nut 40 is an annular lip 112 which can be utilized for snap engagement of particular styles or types of introducers, as required and as later described in detail.

Also shown is a ferrule 74 which aligns within a passageway 75 of the threaded high pressure connection port 42 the combination of which aligns partially within the interior passageway 76 of the Luer connector 44. One end of the high pressure tube 41, shown in segmented form, is utilized for delivery of high pressure ablation liquids and suitably secures in a center passage of the ferrule 74 to communicate with the passageway 75 of the threaded high pressure connection port 42. The high pressure tube 41 also extends through the high pressure connection branch passageway 50, through part of the tapered central passageway 54, through the strain relief 28 and Luer fitting 26, and through the catheter tube 13, through the exhaust tube support rings 78 and 80 to the tip 30 where termination is provided in the form of a fluid jet emanator 82. The high pressure tube 41 can also be attached to the exhaust tube support ring 78, such as by welding or other suitable means, and can function as support for the catheter tube 13 in the region beneath the radiopaque marker 36. Support of the catheter tube 13 in the region beneath the radiopaque marker 38 can be provided by the exhaust tube support ring 80. The introducer 46 having a centrally located hollow shaft 84 and an actuating handle 86 is also shown.

Figure 4:
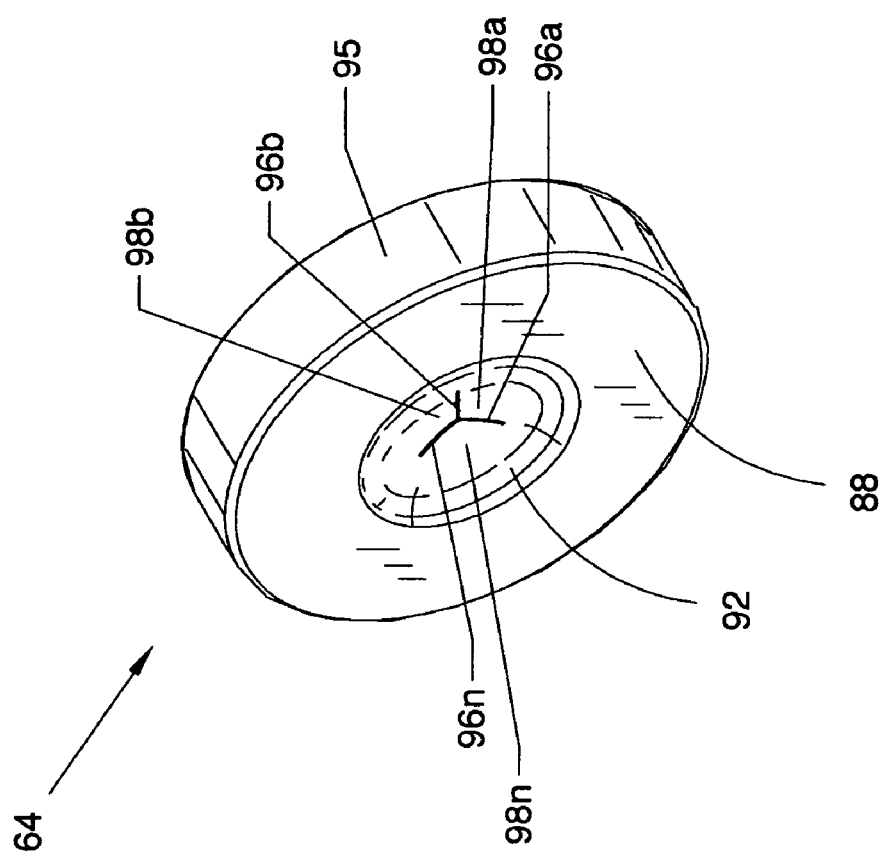
FIG. 4 is an isometric view of the self-sealing hemostasis valve.

FIG. 4 is an isometric view of the self-sealing hemostasis valve 64 which aligns in and which is housed in the cavity 56 and adjacent to and in contact with the elongated washer 66 in the cavity 56 at the proximal region of the manifold 12.

Figure 5:
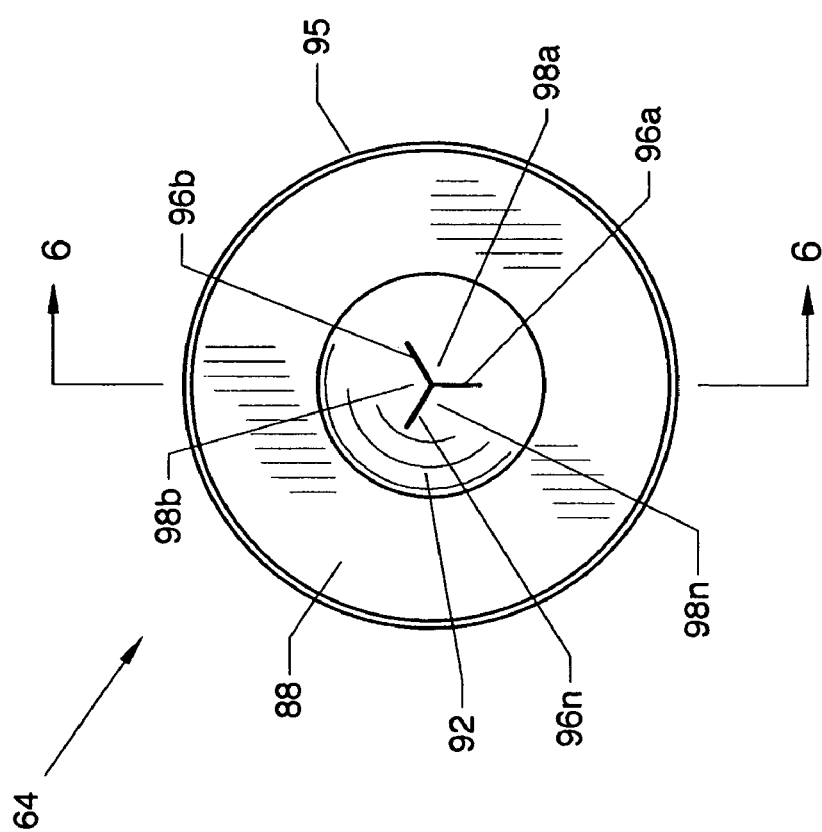
FIG. 5 is a proximal end view of the self-sealing hemostasis valve.
Figure 6:
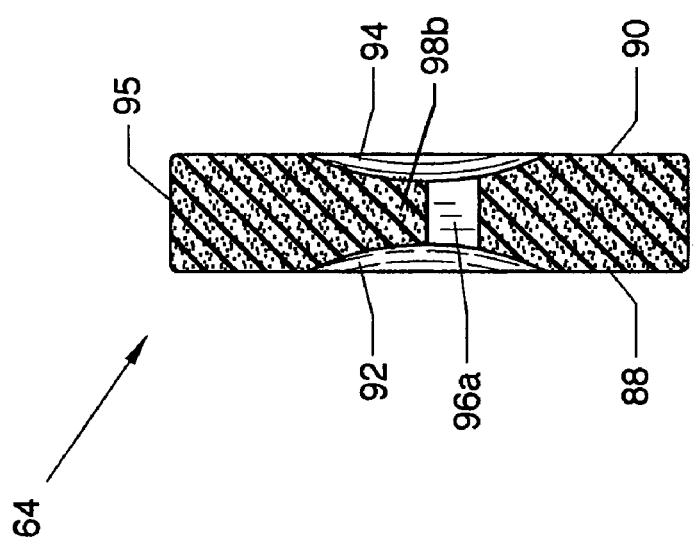
FIG. 6 is a cross section view of the self-sealing hemostasis valve along line 6-6 of FIG. 5.

FIG. 5 is a proximal end view of the self-sealing hemostasis valve 64, and FIG. 6 is a cross section view of the self-sealing hemostasis valve 64 along line 6-6 of FIG. 5. The self-sealing hemostasis valve 64 is made of medical grade silicone material and is symmetrically fashioned to include opposing mirror-like planar and circular-shaped faces 88 and 90 having opposing radiused recessed surfaces 92 and 94 extending therebetween and a circumferential edge 95 between the circular-shaped faces 88 and 90. The medical grade silicone material between the opposing radiused recessed surfaces 92 and 94 is increasingly thinner in a direction towards the center and is parted or otherwise separated to form a plurality of slits 96a-96n, each slit extending outwardly in radial fashion from the center of the self-sealing hemostasis valve 64 part of the distance along and between the radiused recessed surfaces 92 and 94, thus creating boundaries beneficial in defining lobes 98a-98n. That is to say, lobe 98a is located between slits 96a and 96b, lobe 98b is located between slits 96b and 96n, and lobe 98n is located between slits 96n and 96a. Adjacent lobes 98a-98n are in mutual contact along the slits 96a-96n to effect a seal from side to side of the self-sealing hemostasis valve 64. Although three lobes 98a-98n and three slits 96a-96n are shown, any number of each in correspondence can be utilized as desired and shall not be limiting to the scope of the invention. In the alternative, the silicone material of the self-sealing hemostasis valve 64 could be pierced between the recessed surfaces 92 and 94 to yet maintain a self-sealing quality. The self-sealing hemostasis valve 64 is preferably constructed of medical grade silicone but can be fashioned of other suitable flexible, pliable, and resilient material which can conform to and about existing shapes or forms as required, such as to a guidewire. The degree of flexibility of the lobes 98a-98n is influenced by the thickness of the lobes 98a-98n, each of which contains a portion of the radiused recessed surfaces 92 and 94. A guidewire can pass between the inner tips of the lobes 98a-98n while maintaining a seal between the guidewire and the self-sealing hemostasis valve 64. Due to the similar geometrical configuration of the opposing faces and associated structure therebetween, the self-sealing hemostasis valve 64 can be inserted into the cavity 56 without regard to orientation of the self-sealing hemostasis valve 64. The diameter of the self-sealing hemostasis valve 64 is slightly larger than that of the cavity 56 to provide for flexible but snug frictional engagement of the self-sealing hemostasis valve 64 within the cavity 56, as well as to provide for circumferential sealing of the self-sealing hemostasis valve 64 to the cavity 56. The self-sealing hemostasis valve 64 is also incorporated into following embodiments and is slightly larger than that cavity into which it is snugly and frictionally engaged to provide for circumferential sealing to the cavity in which it resides.

Figure 7:
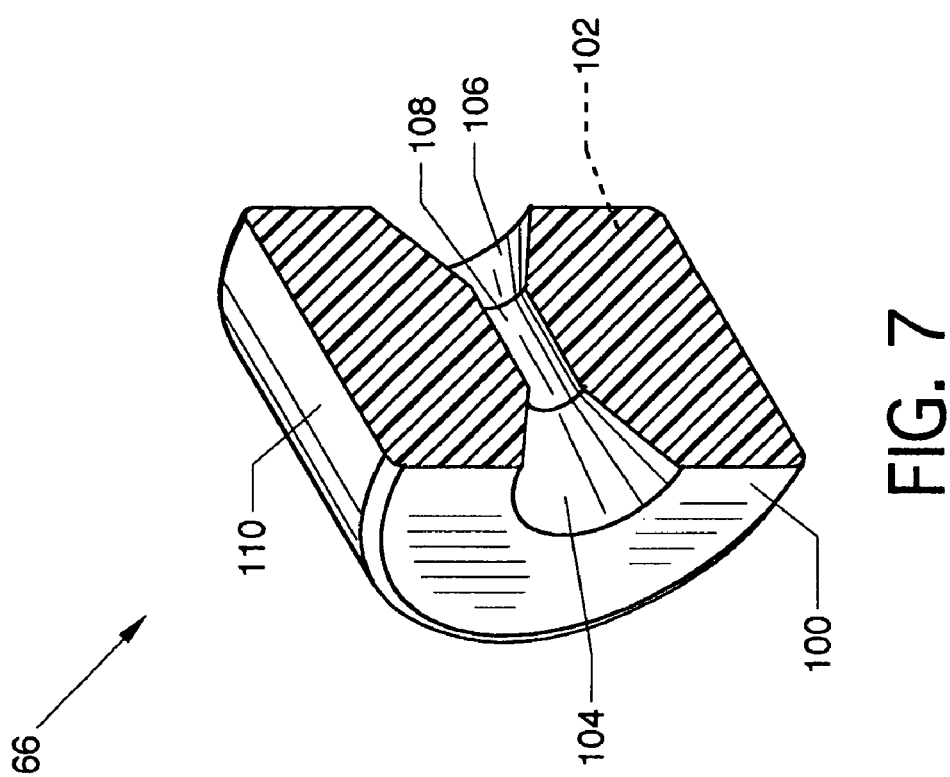
FIG. 7 is an isometric view in cross section of the elongated washer along line 7-7 of FIG. 2.

FIG. 7 is an isometric view in cross section of the elongated washer 66 along line 7-7 of FIG. 2. The elongated washer 66 aligns in and is housed proximally in the cavity 56 adjacent to and in contact with the self-sealing hemostasis valve 64 at the proximal region of the manifold 12.

Figure 8:
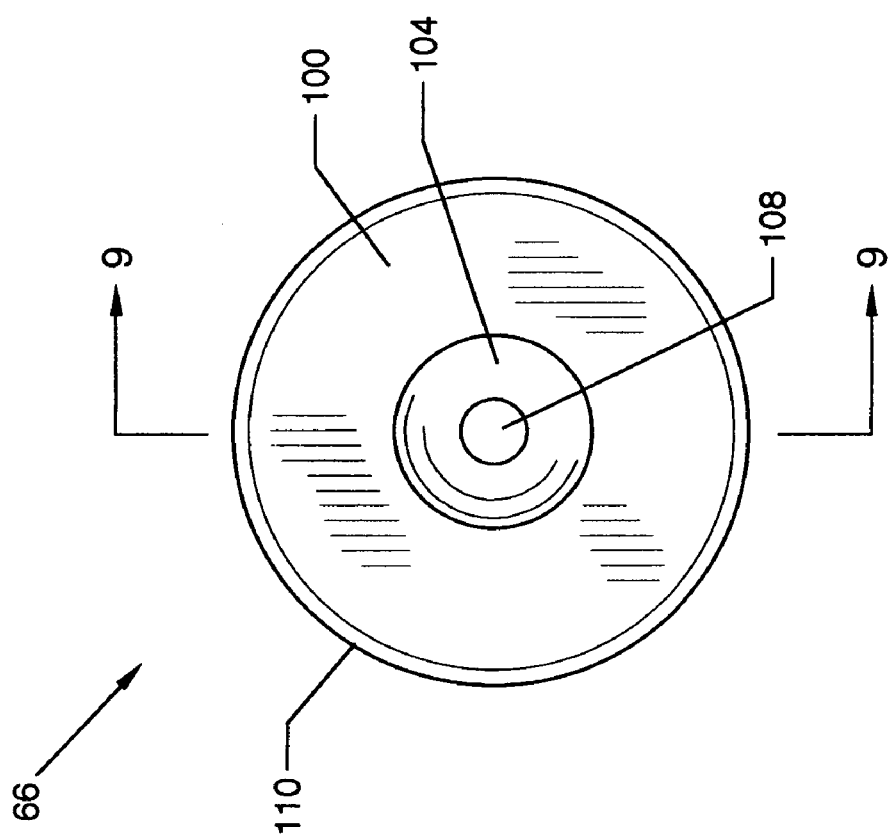
FIG. 8 is a proximal end view of the elongated washer.
Figure 9:
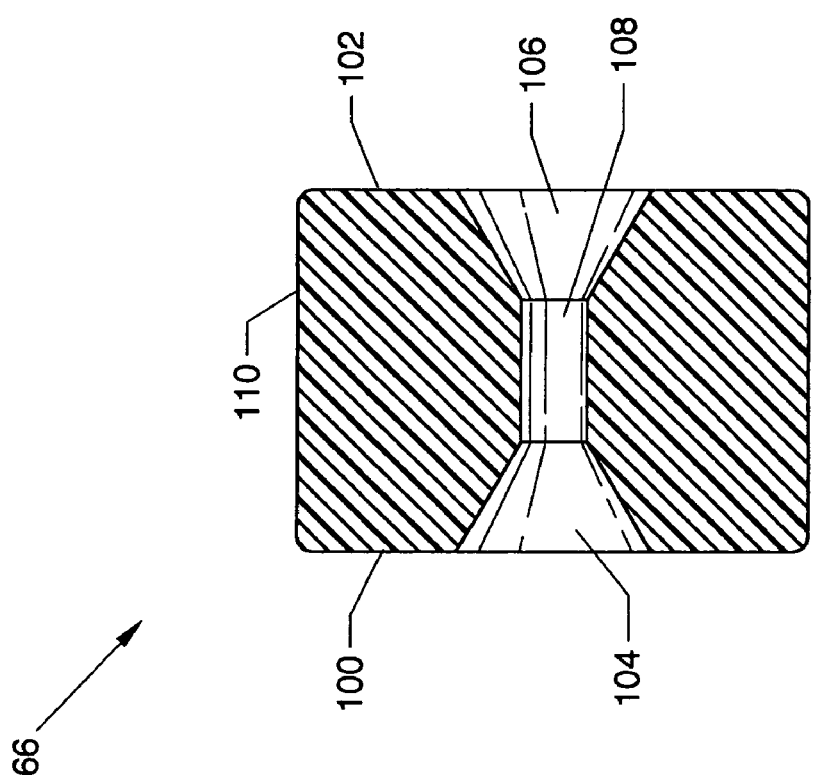
FIG. 9 is a cross section view of the elongated washer along line 9-9 of FIG. 8.

FIG. 8 is a proximal end view of the elongated washer 66, and FIG. 9 is a cross section view of the elongated washer 66 along line 9-9 of FIG. 8. The elongated washer 66 is symmetrically fashioned and preferably constructed of a suitable polycarbonate but could be fashioned of aluminum or other suitable material, as required. The elongated washer 66 is fashioned to include opposing mirror-like planar and circular-shaped faces 100 and 102 having opposing recessed passages 104 and 106, respectively, each having a guidance-friendly truncated conical shape, a central passage 108 extending between the inner portions of the opposing recessed passages 104 and 106, and a circumferential edge 110 between the circular-shaped faces 100 and 102. Due to the similar geometrical configuration of the opposing faces and associated structure therebetween, the elongated washer 66 can be inserted into the cavity 56 without regard to orientation of the elongated washer 66.

Mode of Operation

FIG. 10 is a view in partial cross section of the assembled components of FIG. 3 shown over and about and with the use of a guidewire 48 and showing the introducer 46 detached. In practice, the thrombectomy catheter device having a self-sealing hemostasis valve 10 is engaged over and about the guidewire 48, which could have been previously inserted into the vasculature of a patient. Such loading and engagement occurs where the proximal end of the guidewire 48 enters the tip 30 of the catheter tube 13 and where the proximal guidewire tip is negotiated by the fluid jet emanator 82, the catheter tube 13, the tapered central passageway 54, and the orifice 61 which centers the guidewire 48 to the junction of the tips of the lobes 98a-98n which concurrently locate with the inboard portion of the slits 96a-96n of the self-sealing hemostasis valve 64. Loading continues through the first of the recessed passages 106 or 104 depending on orientation of the elongated washer 66, the central passage 108, the remaining recessed passage 106 or 104 of the elongated washer 66, and thence exiting through the beveled passageway 70 of the hemostasis nut 40. Passage of the guidewire 48 through the junction of the tips of the lobes 98a-98n which concurrently locate with the inboard portion of the slits 96a-96n of the self-sealing hemostasis valve 64 causes the tips and areas immediately surrounding the tips of the lobes 98a-98n to sealingly and slidingly deform, distend, flex, conform or otherwise comply to and accommodate the profile of the guidewire 48. The guidewire 48 is shown in sealing and slidable engagement with the self-sealing hemostasis valve 64 where the pressure in the tapered central passageway 54 can be maintained at an undetermined low setting, as little or no influence by the uncompressed self-sealing hemostasis valve 64 takes place as the self-sealing hemostasis valve 64 is not yet under meaningful control of the hemostasis nut 40 which is only loosely coupled to the proximal region of the cavity body 20. For example, as shown, the cylindrical boss 68 of the hemostasis nut 40 does not yet bring significant pressure against the elongated washer 66 to cause compression of the self-sealing hemostasis valve 64 but still serves to keep the self-sealing hemostasis valve 64 and the elongated washer 66 positioned without movement within the cavity 56.

FIG. 11 is a fragmentary view in cross section of the proximal region of the manifold showing the compression of the self-sealing hemostasis valve 64 by the action of the hemostasis nut 40 being advanced in a distal direction along the threads 62 at the end of the cavity body 20 of the manifold 12. Such action causes forced impingement of the cylindrical boss 68 with the face 100 (assuming such orientation) of the elongated washer 66 to cause the face 102 of the elongated washer 66 to bear against the self-sealing hemostasis valve 64 to cause the self-sealing hemostasis valve 64 to sealingly and slidingly compress, deform, distend, flex, conform or otherwise comply to and accommodate the profile of the guidewire 48 in a forcible manner. Such tightening of the hemostasis nut 40 in the manner just described increases the tightness and effectiveness of a seal about the guidewire 48 by the self-sealing hemostasis valve 64 where a higher attainable pressure may be maintained within the tapered central passageway 54 of the manifold 12 while still maintaining the ability to slide the thrombectomy catheter device having a self-sealing hemostasis valve 10 along the guidewire 48. Tightening of the hemostasis nut 40 also causes expansion of the self-sealing hemostasis valve 64 in an outward direction and a distal direction against portions of the surrounding structure of the cavity 56 and in an inward direction against the guidewire 48, thus influencing the sealing capabilities of the invention.

The self-sealing hemostasis valve 64 is self-sealing when not engaging a guidewire and is self-sealing against an inserted guidewire. The hemostasis nut 40 can be adjusted in the manufacturing process to maintain a desired preset pressure in the tapered central passageway 54 for use in the field and can engage the guidewire 48 and maintain suitable pressure during sliding or static engagement thereof. If it is desired to modify the maintained pressure in the tapered central passageway 54 during use, the practitioner can simply rotate the hemostasis nut 40 to increase or decrease maintained pressure in the tapered central passageway 54 as required.

Figure 12:
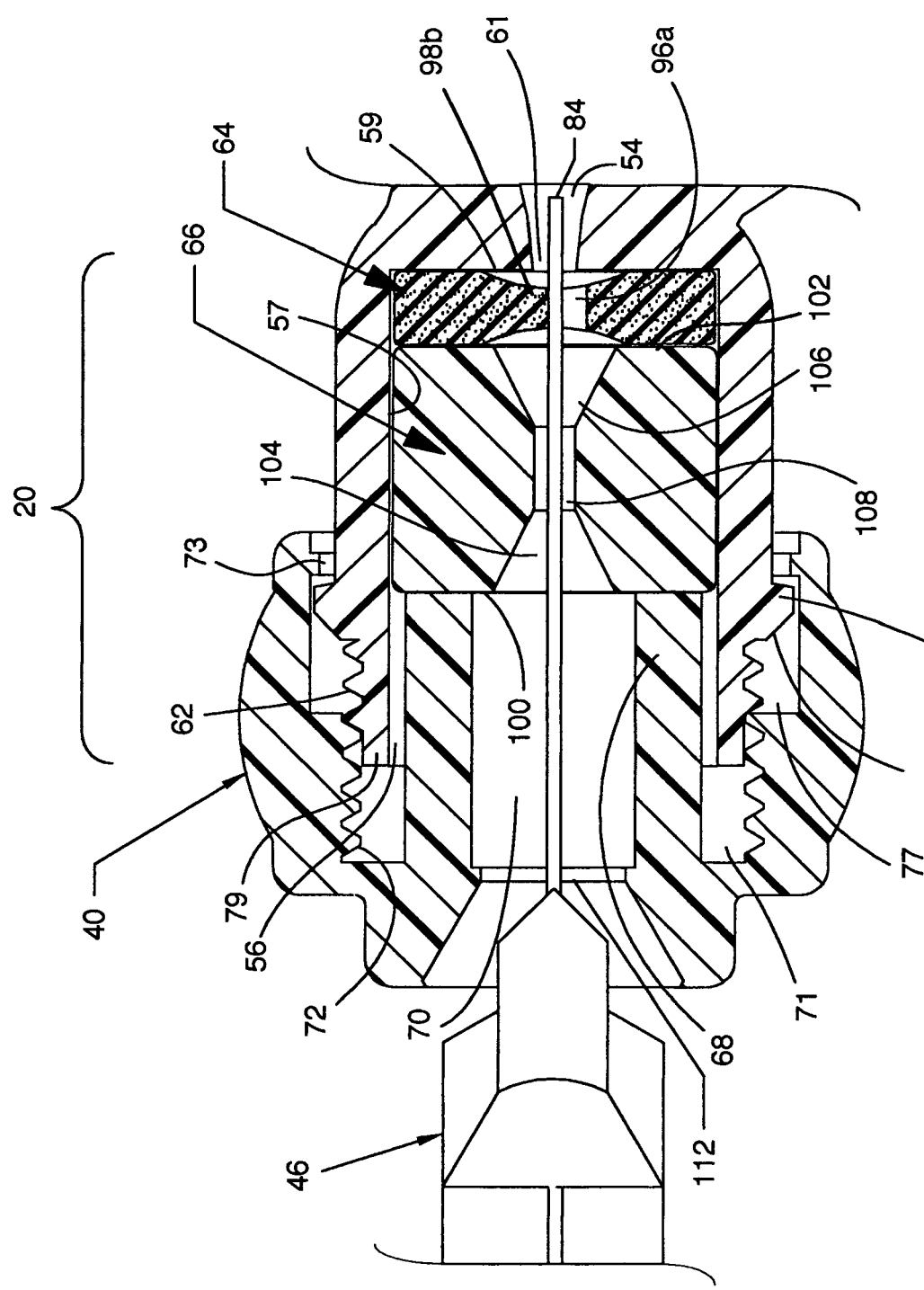
FIG. 12 is a view like FIG. 11 illustrating the use of an introducer, the hollow shaft of which can be inserted through the self-sealing hemostasis valve.

FIG. 12 is a view like FIG. 11 illustrating the use of the introducer 46 the hollow shaft 84 of which can be inserted through the self-sealing hemostasis valve 64 by way of the beveled passageway 70, the recessed passage 104 which serves as a guide to the central passage 108 which in turn serves as a guide for alignment of the hollow shaft 84 of the introducer 46 with the central portion of the self-sealing hemostasis valve 64, and through the intersection of inner tips of the lobes 98a-98n of the self-sealing hemostasis valve 64 and through the orifice 61 and into the tapered central passageway 54 to communicate with the tapered central passageway 54. Passage of the hollow shaft 84 therethrough can be beneficial for purging of air from the manifold 12 (or can be incorporated to assist in flexing of the lobes 98a-98n of the self-sealing hemostasis valve 64 to assist in passage of the guidewire 48 when the invention is loaded over a guidewire beginning at the tip 30). In the alternative, the introducer 46 can be utilized to load a guidewire through the proximal region of the manifold 12, as shown in FIG. 13.

The self-sealing hemostasis valve 64 can also serve as a one-way flow valve where the lobes 98a-98n are restricted to one-way movement. With the inclusion of a guidewire or in the absence of a guidewire and under higher than normal or required internal pressures significantly above those normally required, the lobes 98a-98n can flex in a proximal direction and inwardly and accommodatingly into the recessed passage 106 of the elongated washer 66 to break the seal offered by the lobes 98a-98n. However, negative pressure within the manifold 12 or other unforseen external influences cannot flex the lobes 98a-98n significantly in a distal direction as the planar surface 59 of the cavity 56 offers resistance to such movement and stems any flow in a distal direction. Due to this one-way flow, feature, ingestion of foreign or undesirable substances such as air or particles is denied the self-sealing hemostasis valve 64.

Figure 13:
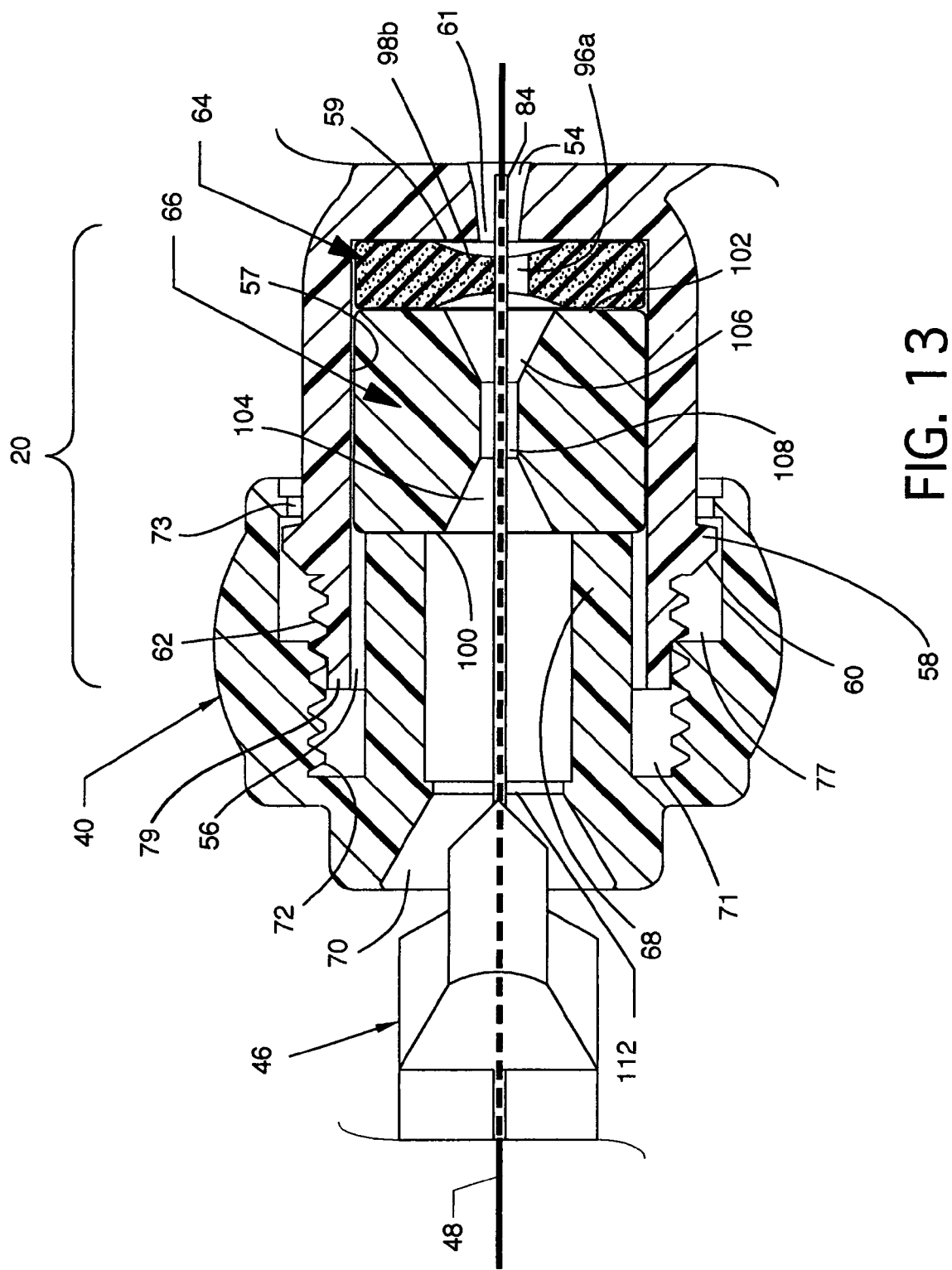
FIG. 13 is a view like FIG. 12 showing the introducer being utilized to load a guidewire through the proximal region of the manifold.

FIG. 13 is a view like FIG. 12 showing the introducer 46 being utilized to load a guidewire 48 through the proximal region of the manifold 12. This feature is useful if difficulty in negotiating the self-sealing hemostasis valve 64 by the guidewire 48 is encountered.

Figure 14:
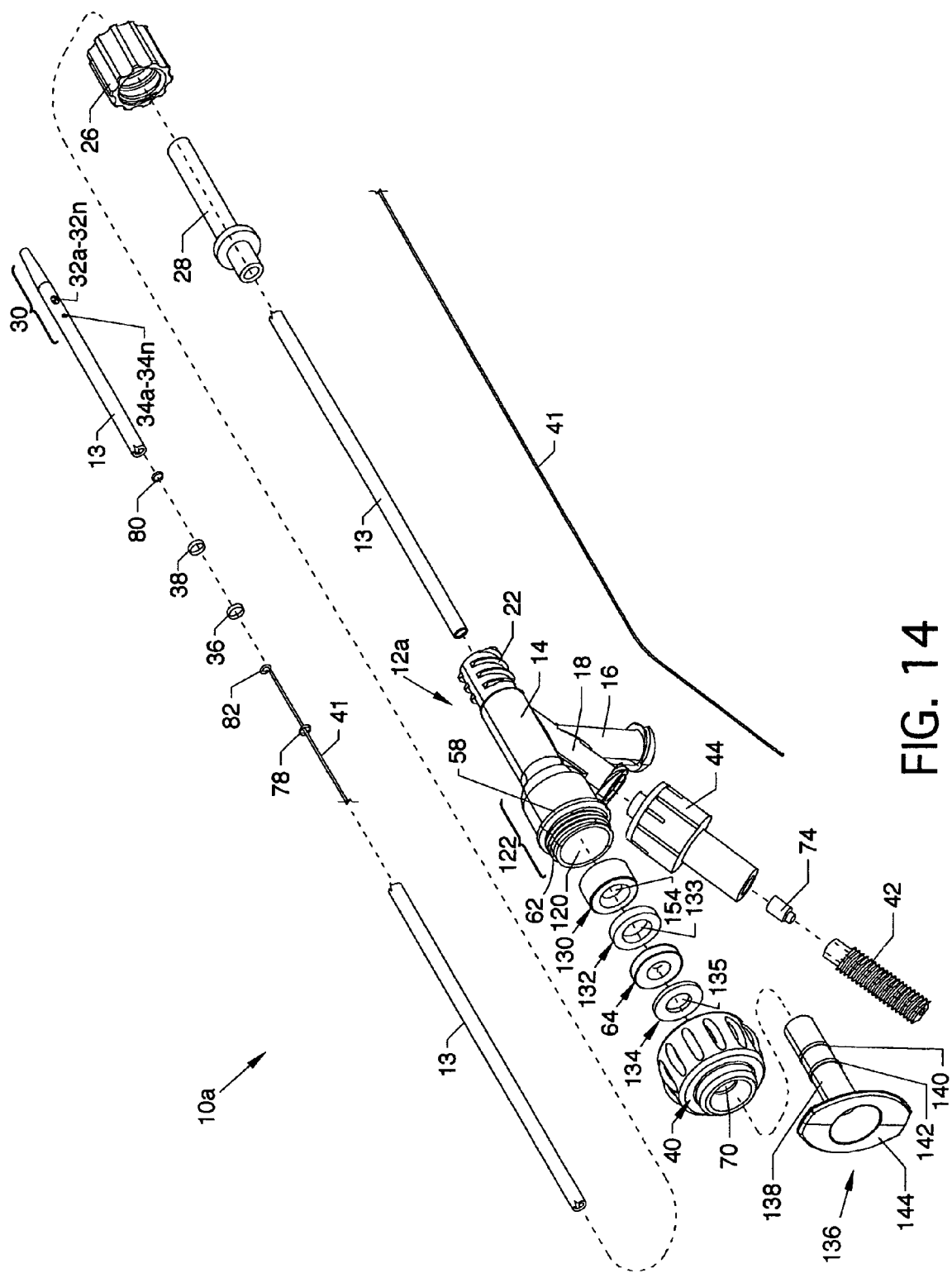
FIG. 14, a first alternate embodiment, is an isometric exploded view of a thrombectomy catheter device having a self-sealing hemostasis valve.
Figure 15:
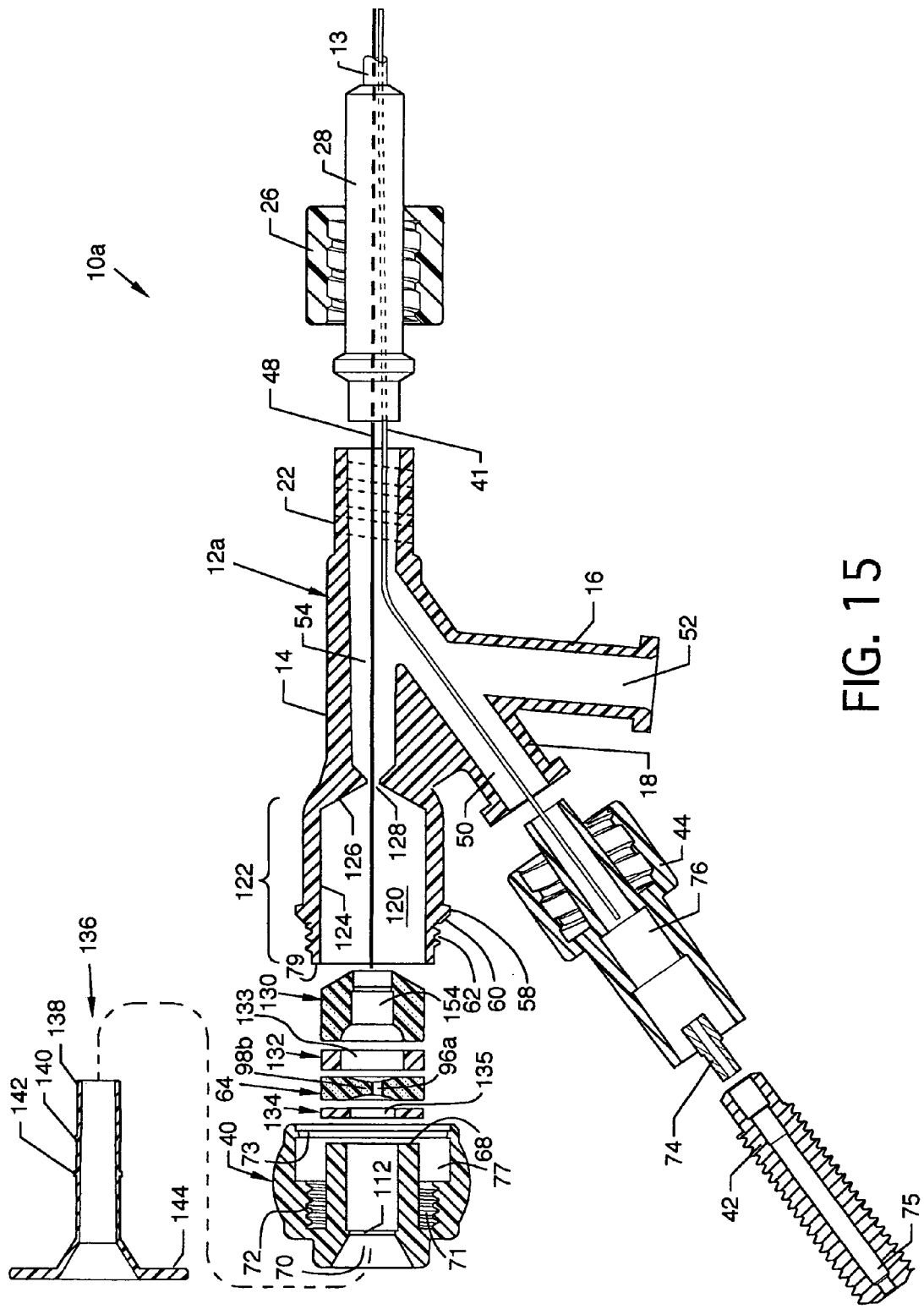
FIG. 15 is an exploded view in partial cross section of the components of the first alternate embodiment thrombectomy catheter device having a self-sealing hemostasis valve.

FIG. 14, a first alternate embodiment, is an isometric exploded view of a thrombectomy catheter device having a self-sealing hemostasis valve 10a, and FIG. 15 is an exploded view in partial cross section of the components of the thrombectomy catheter device having a self-sealing hemostasis valve 10a. The thrombectomy catheter device having a self-sealing hemostasis valve 10a utilizes the majority of the components, structures, and features of the previously described thrombectomy catheter device having a self-sealing hemostasis valve 10, and also operates similarly, but includes a different arrangement and/or type of components that align within and which are accommodated internally by an alternately configured cavity 120 located in a cavity body 122 of a manifold 12a. The cavity 120 is for the most part tubular in shape including a tubular cavity wall 124 and a truncated conical surface 126 which intersects the tubular cavity wall 124. An orifice 128 located central to the truncated conical surface 126 is common to the cavity 120 and the tapered central passageway 54. The cavity 120 accommodates, amongst other components, a dual seal 130 fashioned and preferably constructed of medical grade silicone or of other suitable flexible, pliable, and resilient material which can conform to and about existing shapes or forms as required, such as to a guidewire. The diameter of the dual seal 130 is slightly larger than that of the cavity 120 to provide for flexible but snug frictional engagement of the dual seal 130 within the cavity 120, as well as providing for circumferential sealing of the dual seal 130 to the cavity 120. The cavity 120 also accommodates, in order adjacent to the dual seal 130, a wide washer 132 of TEFLON® or other suitable flexible material having a central passage 133, the self-sealing hemostasis valve 64, previously described, and a washer 134, preferably similar in composition to the wide washer 132, having a central passage 135.

The washer 134 and the wide washer 132 may also be incorporated into other embodiments and function as low friction spacers to reduce rotational frictional binding to maintain the proper shape of the self-sealing hemostasis valve 64 and the dual seal 130 when the hemostasis nut 40 is tightened. Due to the similar geometrical configurations of the opposing faces and associated structure therebetween of the wide washer 132, the self-sealing hemostasis valve 64, and the washer 134, these three components can be inserted into the cavity 120 without regard to the orientation of each. Also provided as part of the invention is an introducer 136 having a hollow shaft 138, annular rings 140 and 142 about the hollow shaft 138, and an actuating handle 144. The washer 134 provides for accommodated communication with the introducer 136.

Figure 16:
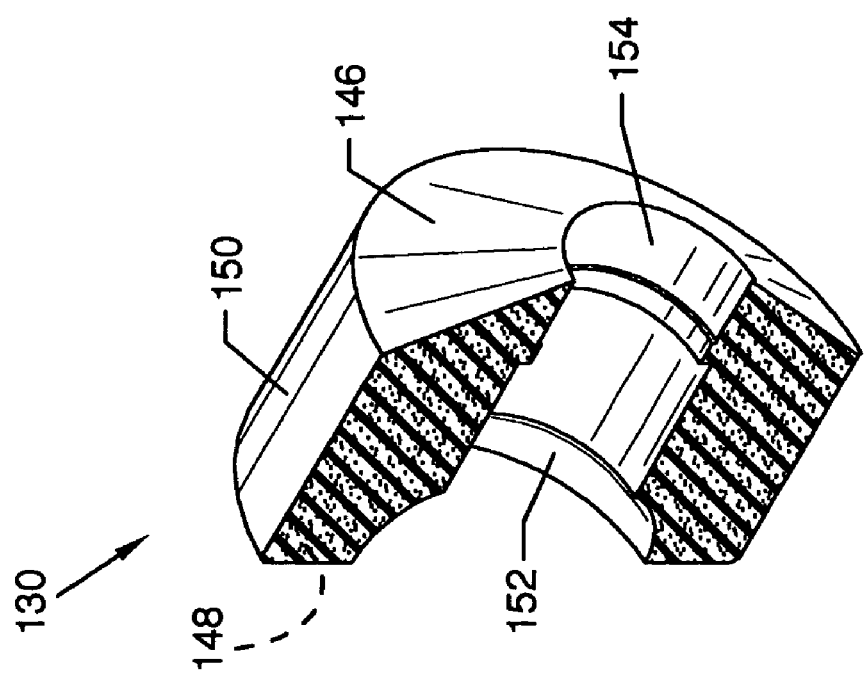
FIG. 16 is an isometric view in cross section of the dual seal which aligns in and which is housed distally in a cavity in the manifold.
Figure 17:
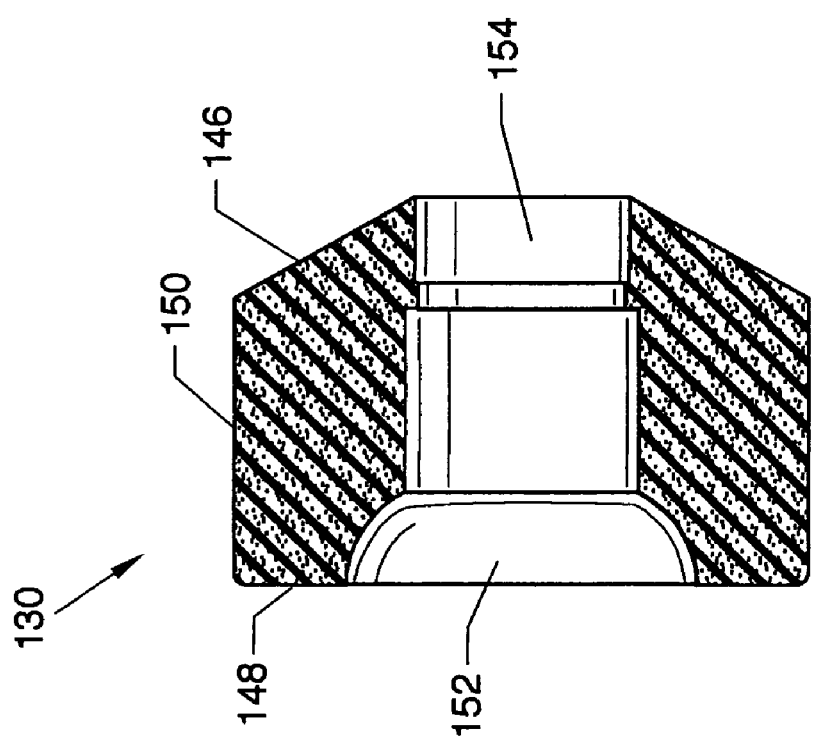
FIG. 17 is a longitudinal cross section view of the dual seal.
Figure 18:
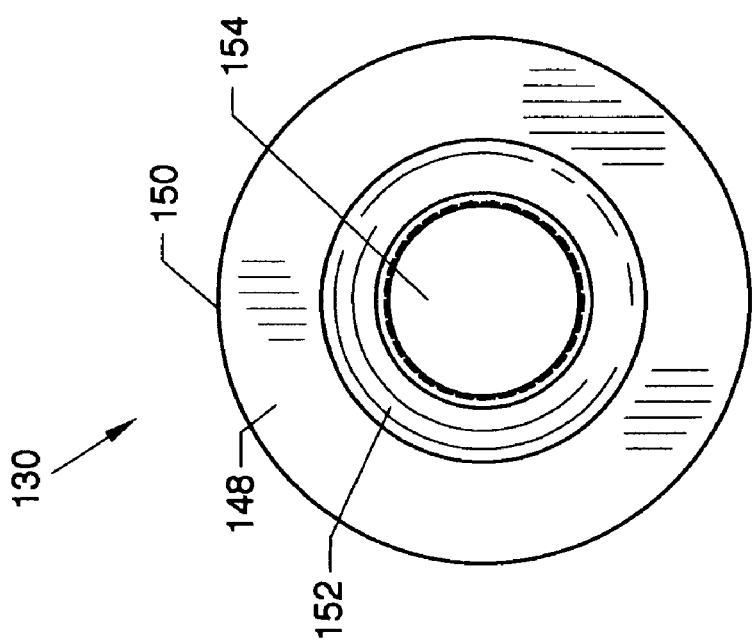
FIG. 18 is a proximal end view of the dual seal.

FIGS. 16, 17 and 18 illustrate the dual seal 130 which seals in dual, i.e., in different, directions along and about different regions. One such seal involving the dual seal 130 is effected in an outward direction against and in intimate contact with the surrounding structure of the cavity 120, and the other seal involving the dual seal 130 is effected in an inward direction against and in intimate contact with the guidewire 48 in the compressed stage, as later described in detail. FIG. 16 is an isometric view in cross section of the dual seal 130 which aligns in and is housed distally in the cavity 120 and adjacent to and in contact with the wide washer 132 in the manifold 12a. FIG. 17 is a longitudinal cross section view of the dual seal 130. FIG. 18 is a proximal end view of the dual seal 130. The dual seal 130 of medical grade silicone material is fashioned to include a distally located truncated conical surface 146 which is complementary to and which comes into intimate contact with the truncated conical surface 126 of the cavity 120, an opposing proximally located planar and circular-shaped face 148, an outer circumferential edge 150 extending between the truncated conical surface 146 and the face 148, a rounded recess 152 juxtaposing face 148, and a multi-radiused passageway 154 extending along the centerline between the rounded recess 152 and the truncated conical surface 146.

Mode of Operation

Figure 19:
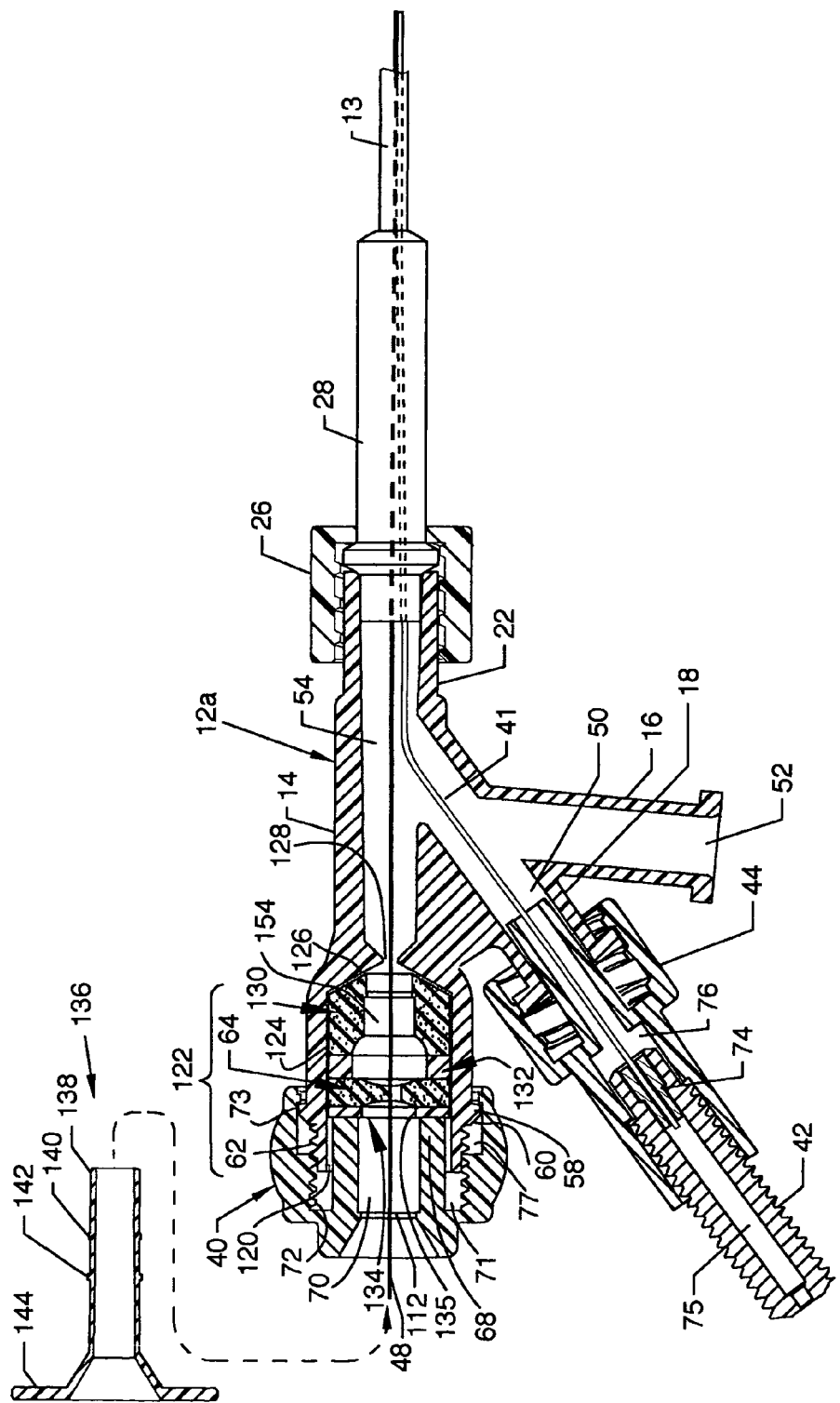
FIG. 19 is a view in partial cross section of the assembled components of the first alternate embodiment shown over and about and with the use of a guidewire and showing the introducer detached.

FIG. 19 is a view in partial cross section of the assembled components of the alternate embodiment shown in FIG. 15 shown over and about and with the use of a guidewire 48 and showing the introducer 136 detached. Such loading and engagement occurs much in the same fashion as previously described with reference to FIG. 10 where the proximal end of the guidewire 48 enters the tip 30 of the catheter tube 13 and where the proximal guidewire tip is negotiated by the fluid jet emanator 82, the catheter tube 13, the tapered central passageway 54, and the orifice 61 which centers the guidewire 48 to the components contained in the cavity 120. Such loading continues through the multi-radiused passageway 154 of the dual seal 130, the central passage 133 of the wide washer 132, and thence through the junction of the tips of the lobes 98a-98n which concurrently locate with the inboard portion of the slits 96a-96n of the self-sealing hemostasis valve 64 which, as previously described, can be oriented in either direction. Loading continues through the central passage 135 of the washer 134 and exiting through the beveled passageway 70 of the hemostasis nut 40. Passage of the guidewire through the junction of the tips of the lobes 98a-98n which concurrently locate with the inboard portion of the slits 96a-96n of the self-sealing hemostasis valve 64 causes the tips and areas immediately surrounding the tips of the lobes 98a-98n to sealingly and slidingly deform, distend, flex, conform or otherwise comply to and accommodate the profile of the guidewire 48. The guidewire 48 is shown in sealing and slidable engagement with the self-sealing hemostasis valve 64 where the pressure in the tapered central passageway 54 can be maintained at a low undetermined setting, as little or no influence by the uncompressed self-sealing hemostasis valve 64 takes place as the self-sealing hemostasis valve 64 is not yet under control of the hemostasis nut 40 which is only loosely coupled to the proximal region of the cavity body 122. For example, as shown, the cylindrical boss 68 of the hemostasis nut 40 does not yet bring significant pressure against the components residing in the cavity 120 including the dual seal 130, the wide washer 132, the self-sealing hemostasis valve 64, and the washer 134, but still serves to keep the dual seal 130, the wide washer 132, the self-sealing hemostasis valve 64, and the washer 134 positioned without movement within the cavity 120. As previously described, the hemostasis nut 40 can made to threadingly engage the proximal region of the manifold 12*a* and to be advanced to compress the components residing in the cavity 120. As shown in the following FIG. 20, the introducer 136 snappingly engages the hemostasis nut 40.

Figure 20:
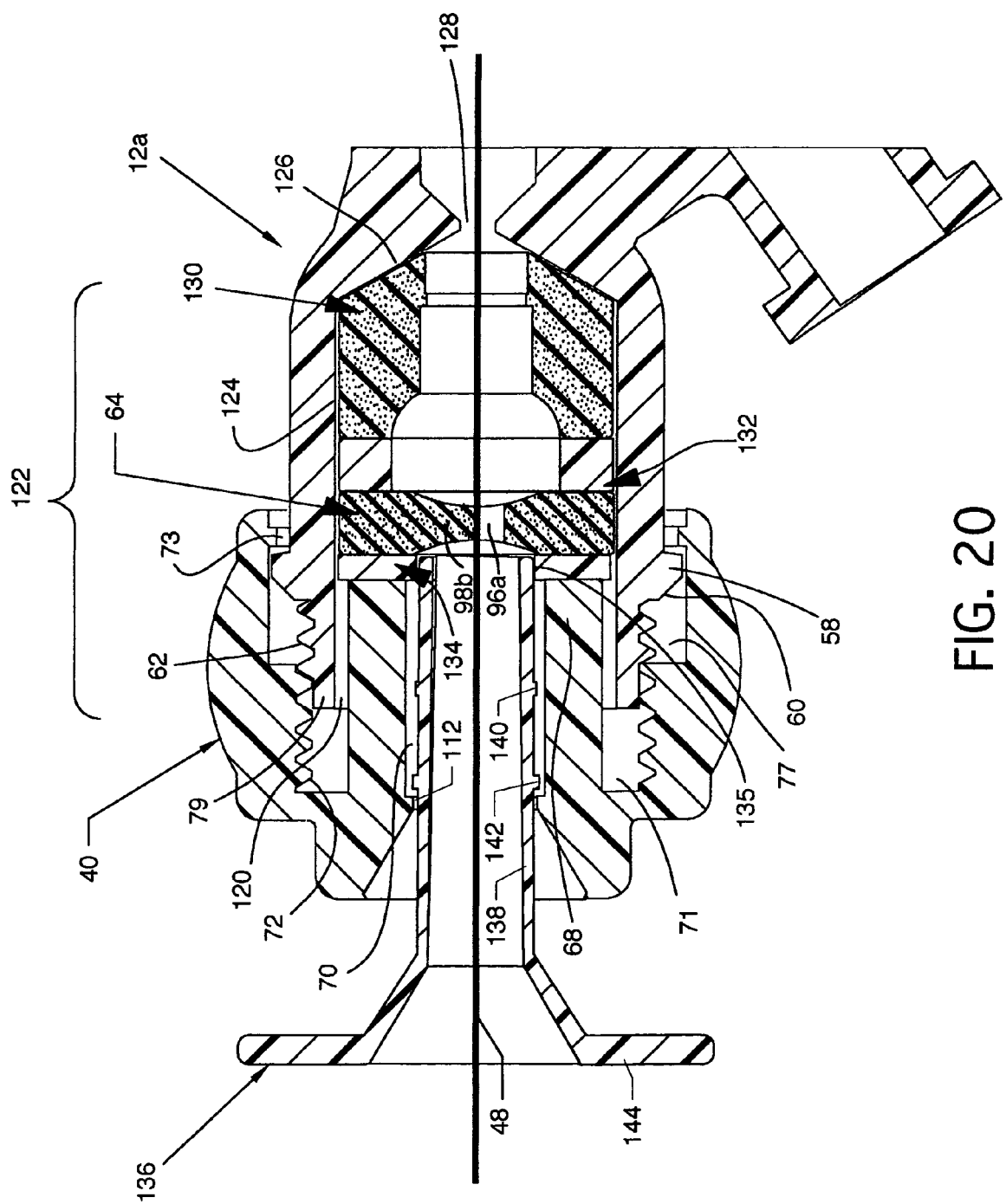
FIG. 20 is a fragmentary view in cross section of the proximal region of the manifold of the first alternate embodiment illustrating the introducer in engagement with the hemostasis nut and where the hemostasis nut is in loose engagement with the proximal region of the manifold.
Figure 21:
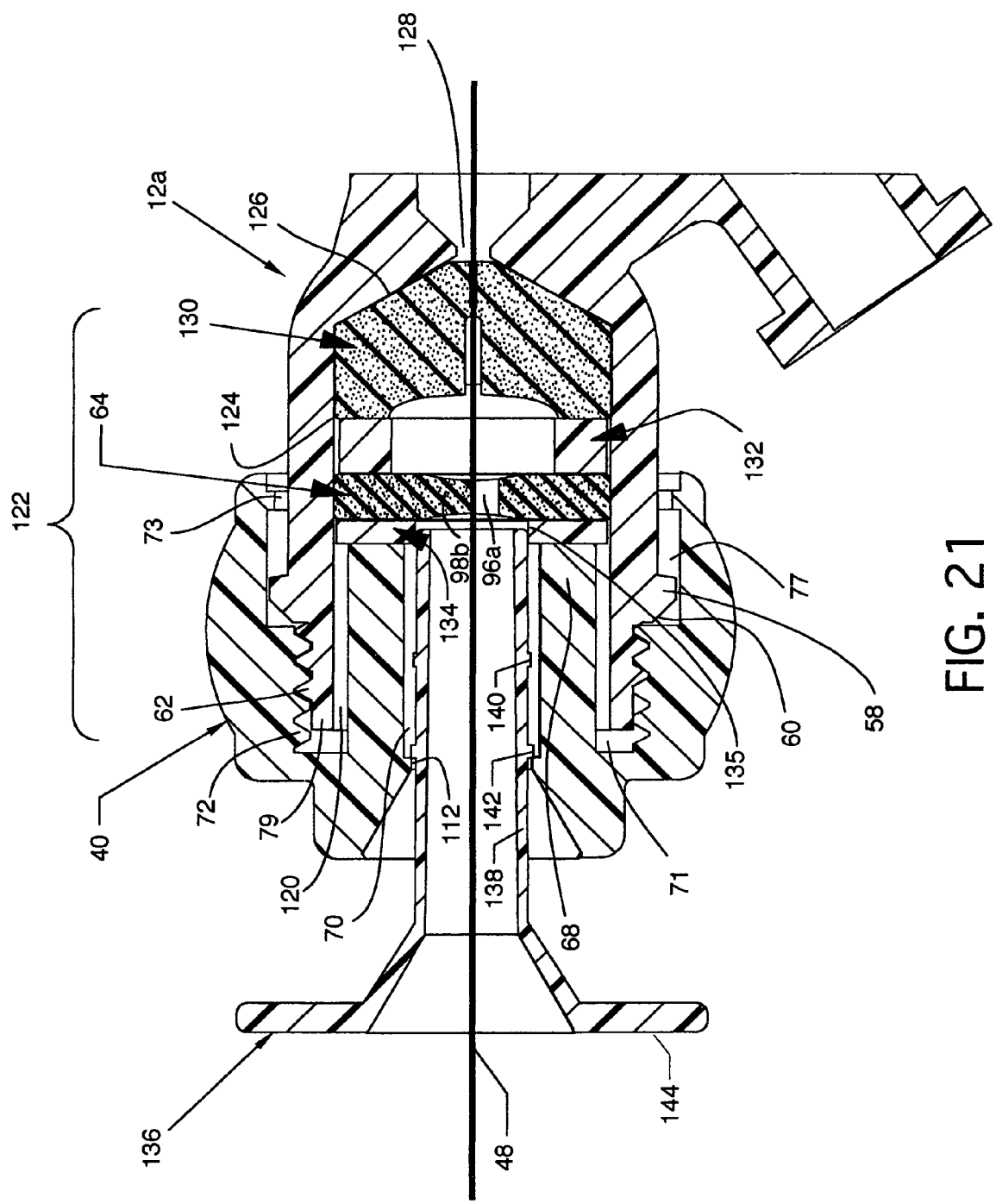
FIG. 21 is a view like FIG. 20 showing further advancement of the hemostasis nut distally to impact and utilize the sealing capabilities of the dual seal to effect hemostasis where a thinner guidewire is utilized and a seal between the self-sealing hemostasis valve and the thinner guidewire is not practicable.

FIG. 20 is a fragmentary view in cross section of the proximal region of the manifold 12*a* illustrating the introducer 136 in engagement with the hemostasis nut 40 and where the hemostasis nut 40 is in loose engagement with the proximal region of the manifold 12*a*. Engagement of the introducer 136 with the hemostasis nut 40 is accomplished by snap engagement of the annular ring 142 with and in a distal direction beyond the annular lip 112 of the hemostasis nut 40. The distal end of the hollow shaft 138 of the introducer 136 slidingly engages and is in intimate contact with the wall of the central passage 135 of the washer 134 to firm up the relationship of the introducer 136 with the hemostasis nut 40 so that the introducer 136 does not exhibit a tendency to appear in floppy or unsuitable connection to the hemostasis nut 40, thereby providing stabilization between the introducer and the hemostasis nut 40. The self-sealing hemostasis valve 64 provides for sealing about guidewire 48 in a manner as previously described dependent on the degree of compression applied to the self-sealing hemostasis valve 64 by advancement of the hemostasis nut 40 distally. The inclusion of the wide washer 132 and the washer 134 aids in transferring force evenly and minimizes binding of the self-sealing hemostasis valve 64 and the dual seal 130 when the hemostasis nut 40 is advanced to the desired setting. The hemostasis nut 40 can be factory adjusted to maintain a desired manifold pressure, as previously described. Adjustments other than those made in the factory setting affect both the self-sealing hemostasis valve 64 and the dual valve 130 simultaneously but to different degrees and in different stages where advancement of the hemostasis nut 40 distally firstly and significantly impacts and utilizes the sealing capabilities of the self-sealing hemostasis valve 64 to control pressure at and about the self-sealing hemostasis valve 64 where the relationship of the self-sealing hemostasis valve 64 to the guidewire 48 and to the surrounding cavity 120 is predominately the same as described for the preferred embodiment (FIG. 11). As shown in FIG. 21, further advancement of the hemostasis nut 40 distally utilizes the sealing capabilities of the self-sealing hemostasis valve 64 to whatever extent possible, and additionally impacts and utilizes the sealing capabilities of the dual seal 130 to effect hemostasis in special cases, one case being such as where a thinner guidewire is utilized and a seal between the self-sealing hemostasis valve 64 and the thinner guidewire is less than satisfactory. Such movement longitudinally compresses the dual seal 130 to cause the material of the dual seal 130 to expand in an outward direction against the cavity wall 124 to increase intimate contact pressure therebetween and to increase intimate contact pressure in a distal direction against the truncated conical surface 126 of the surrounding structure of the cavity 120 and to expand the structure of the dual seal 130 in an inward direction to force and form portions of the multi-radiused passageway 154 around, about and against a guidewire the preceding of which seals the dual seal 130 both against the walls of the cavity 120 and to the guidewire 48. Depending on the degree of compression about the guidewire 48 as caused by advancement of the hemostasis nut 40, the manifold 12*a* can be moved in either direction with a slight amount of lateral force; or in the case where friction along the guidewire 48 cannot be readily overcome, the hemostasis nut 40 can be adjusted a small amount to allow positioning of the manifold 12*a* along the guidewire 48 and then retightened while still effecting suitable hemostasis. Advancing the hemostasis nut 40 distally with respect to the cavity 120 during such engagement compresses the dual seal 130 increasingly to increase the allowable pressure which may be maintained within the manifold 12*a* to obtain suitable hemostasis. The hemostasis nut may be retarded proximally from an advanced distal position to controllingly decrease compression of the dual seal 130 about the guidewire and against the cavity 120 to maintain hemostasis at a lesser pressure if able.

Figure 22:
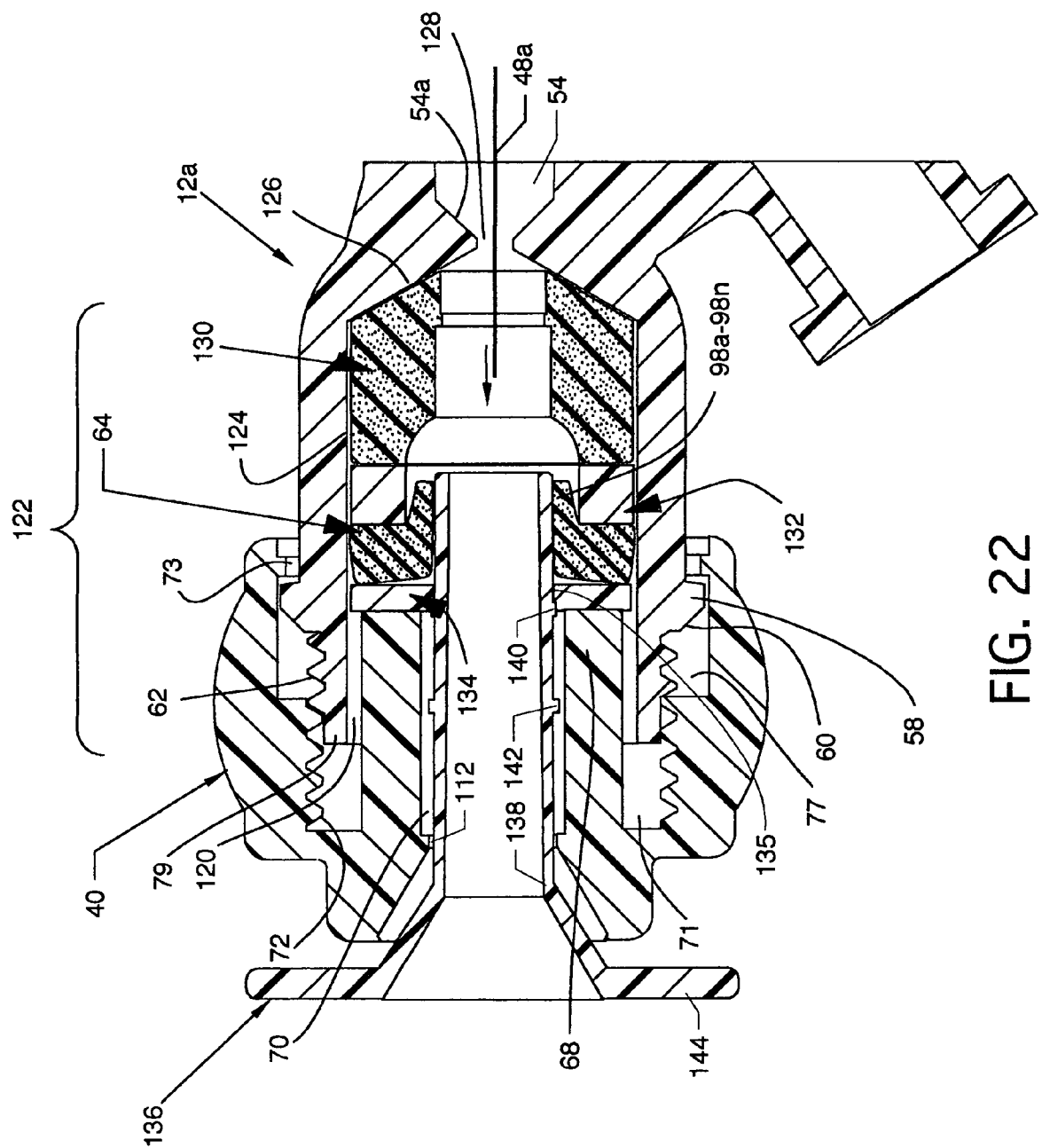
FIG. 22 is a view like FIG. 20 illustrating the actuation of the introducer to perform alternate functions as required either to bleed air out of the manifold or to aid guidewire movement through the dual seal and/or self-sealing hemostasis valve when the hemostasis nut is loosely engaging the proximal region of the manifold.

FIG. 22 is a view like FIG. 20 illustrating the function of the introducer 136 to perform alternate functions as required either to bleed air or fluids out of the manifold 12*a* or to aid guidewire movement through the dual seal 130 and/or self-sealing hemostasis valve 64 when the hemostasis nut 20 is loosely engaging the proximal region of the manifold 12*a* and having little or no significant effect upon the components residing in the cavity 120. To achieve usefulness, the actuating handle 144 of the introducer 136 is manually pushed in a distal direction to force the distal end of the hollow shaft 138 towards and through the slits 96*a*-96*n* of the self-sealing hemostasis valve 64. Such entry into and through the self-sealing hemostasis valve 64 flexes, deforms and distends the lobes 98*a*-98*n* apart and in a distal direction to render the sealing capability against a guidewire, such as guidewire 48, ineffective. The ability to spread or open the tips of the lobes 98*a*-98*n* is useful for use with an alternate guidewire, such as guidewire 48*a*, of a thinner or more flexible nature where the reduced thickness or increased flexibility thereof decreases or hinders the ability of the alternate guidewire 48*a* to successfully navigate, negotiate or pass through the lobes 98*a*-98*n* in their normal sealed position. In such state, any air of a pressure higher than ambient in the tapered central passageway 54 and connecting passages or tubes or other pertinent pressure carrying structures is vented to ambient through the hollow shaft 138 of the introducer 136. As readily seen in the illustration, the introducer 136 provides a relatively large passageway through the hollow shaft 138 for introduction of the proximal end of an alternate guidewire 48*a*, or the guidewire 48, for passage therethrough. The proximal end of the alternate guidewire 48*a* is aligned to the hollow shaft 138 by a taper 54*a* at the proximal end of the tapered central passageway 54 adjacent to the orifice 128 and by the orifice 128 common to both the tapered central passageway 54 and the cavity 120. Subsequent to passage of the proximal end of the guidewire 48*a* to a position proximal to the flexed, distended and deformed self-sealing hemostasis valve 64, the introducer can be retarded proximally to disengage from intimate contact with the self-sealing hemostasis valve 64, whereupon a seal is established with the guidewire 48*a* (or guidewire 48) and the self-sealing hemostasis valve 64 regains sealing qualities relating to the guidewire 48*a* (or guidewire 48) and cavity 120, such as previously described.

Figure 23:
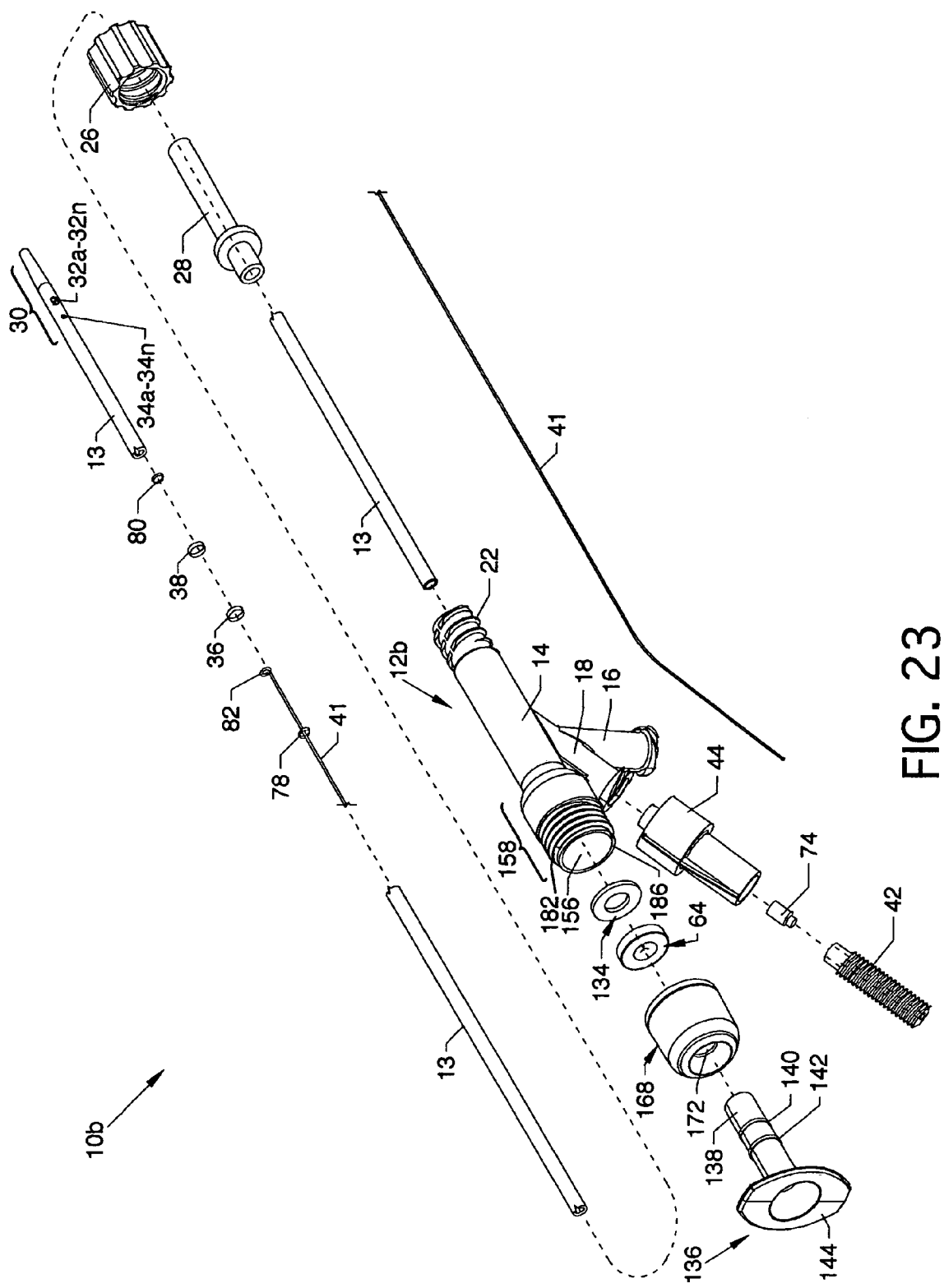
FIG. 23, a second alternate embodiment, is an isometric exploded view of a thrombectomy catheter device having a self-sealing hemostasis valve.
Figure 24:
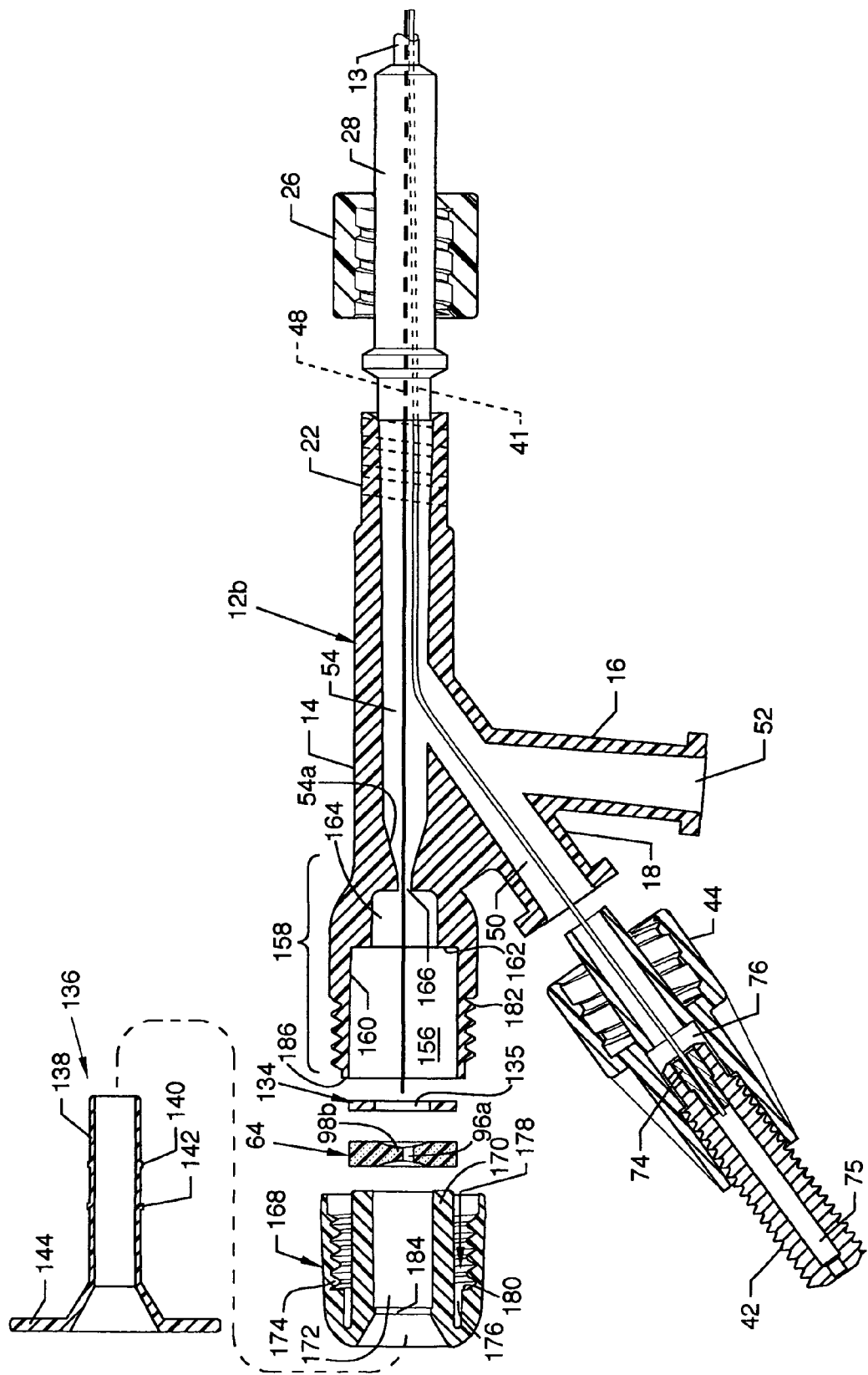
FIG. 24 is an exploded view in partial cross section of the components of the second alternate embodiment thrombectomy catheter device having a self-sealing hemostasis valve.

FIG. 23, a second alternate embodiment, is an isometric exploded view of a thrombectomy catheter device having a self-sealing hemostasis valve 10*b*, and FIG. 24 is an exploded view in partial cross section of the components of the second alternate embodiment thrombectomy catheter device having a self-sealing hemostasis valve 10*b*. The second alternate embodiment provides a thrombectomy catheter device having a self-sealing hemostasis valve 10*b* which features a nonadjustable hemostasis nut 168 fixed over and about the proximal region of a manifold 12*b*. The thrombectomy catheter device having a self-sealing hemostasis valve 10*b* utilizes a large number of the components, structures, and features of the previously described thrombectomy catheter devices having a self-sealing hemostasis valve 10 and 10*a* and also operates in a somewhat similar fashion, but includes a different arrangement and/or type of components that align within and/or which can be associated with and which can be accommodated internally by an alternately configured cavity 156 located in a cavity body 158 of the manifold 12*b*. The cavity 156 is for the most part tubular in shape including a tubular cavity wall 160 and a planar surface 162 which is annular and circular and which intersects the tubular cavity wall 160. A cavity extension 164, being for the most part tubular, extends distally from the cavity 156 beginning at the planar surface 162 to intersect and connect with an orifice 166. The orifice 166 is common to the cavity extension 164, the cavity 156 and to the tapered central passageway 54 located central to the central tubular body 14. The cavity 156 accommodates, in order adjacent to planar surface 162, the flexible washer 134 of TEFLON® or other suitable flexible material having the central passage 135 and the self-sealing hemostasis valve 64, previously described. The washer 134 functions as a low friction spacer to reduce rotational frictional binding to maintain the proper shape of the self-sealing hemostasis valve 64 when the hemostasis nut 168 is tightened. The washer 134 provides for stabilization introducer 136.

Figure 25:
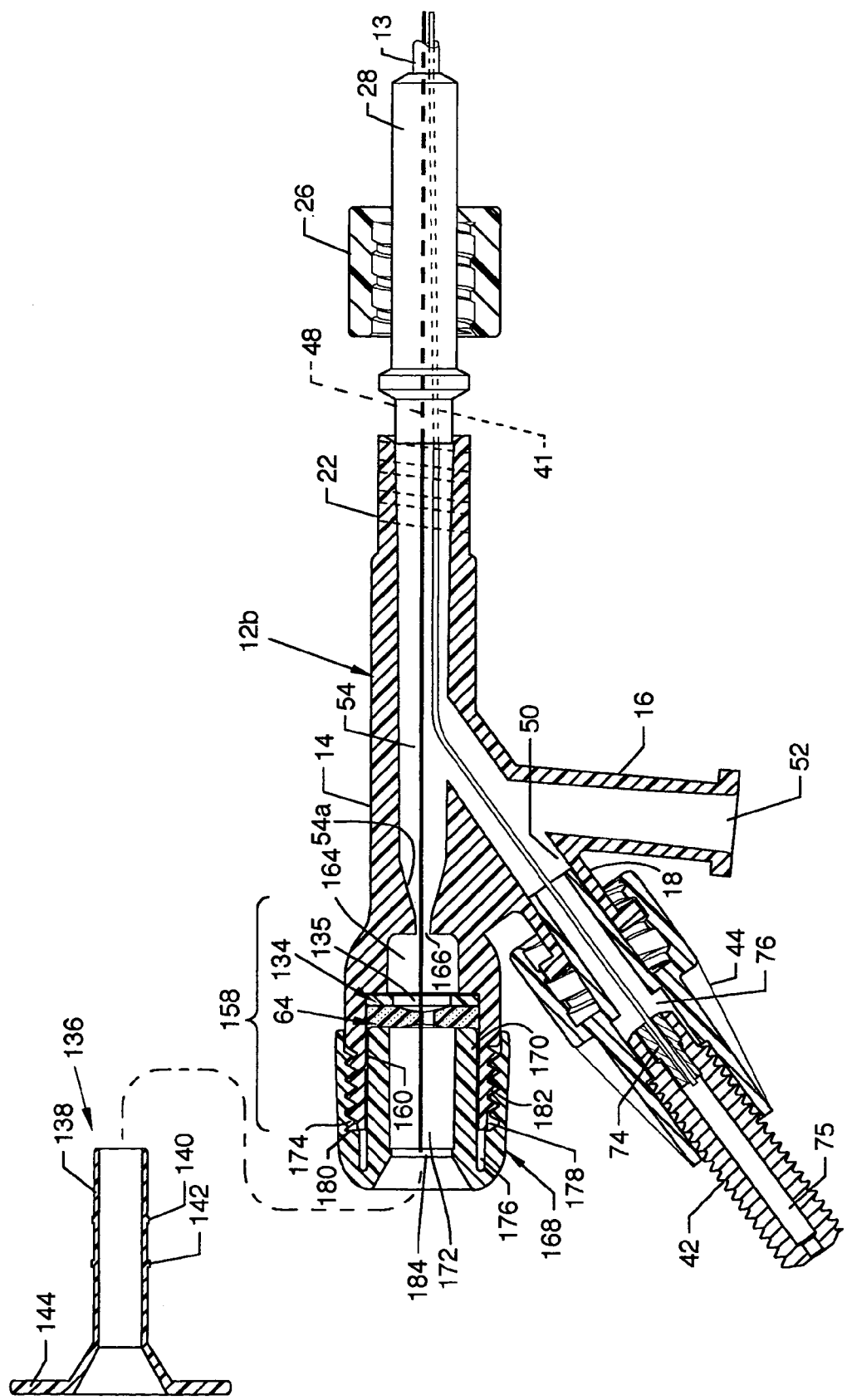
FIG. 25 is a view in partial cross section of the assembled components of the second alternate embodiment shown over and about and with the use of a guidewire and showing the introducer detached.
Figure 26:
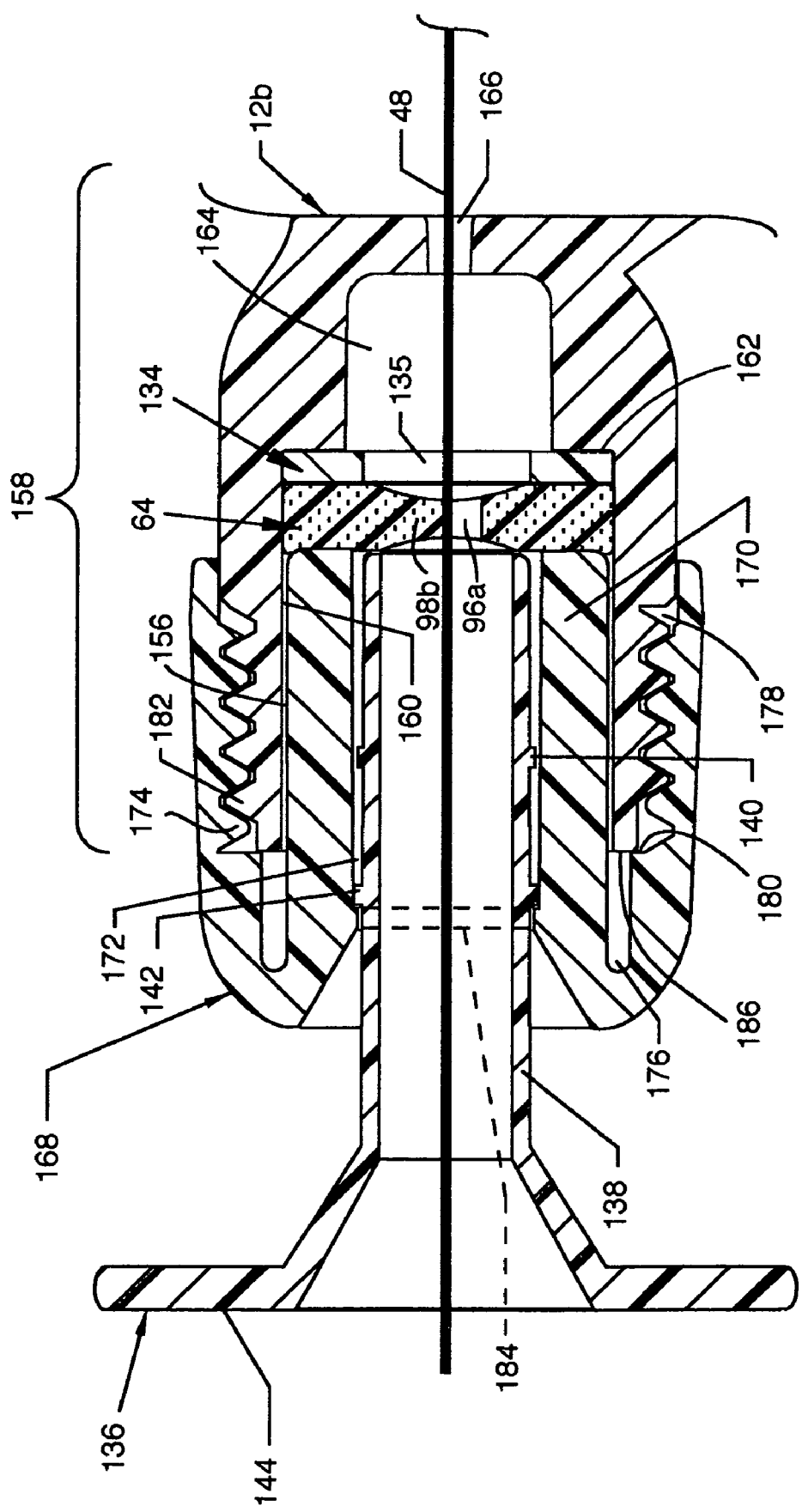
FIG. 26 is a fragmentary view in cross section of the proximal region of the manifold of the second alternate embodiment illustrating the introducer in normal engagement with the hemostasis nut and where the hemostasis nut is in fixed nonadjustable engagement with the proximal region of the manifold.

Also provided as part of the second alternate embodiment is the introducer 136, previously described, having a hollow shaft 138, annular rings 140 and 142 about the hollow shaft 138, and an actuating handle 144 which aligns in hemostasis nut 168. The hemostasis nut 168 includes a centrally located cylindrical boss 170, a beveled passageway 172 extending through and in part forming the cylindrical boss 170, and internal threads 174 distanced from the cylindrical boss 170 by a distally located space 178 extending along the internal threads 174 and along the distal portion of the cylindrical boss 170. A proximally located space 176 is located adjacent to the distally located space 178, and an annular stop surface 180 is located between the proximal region of the internal threads 174 and the distal region of the proximally located space 176. The distally located space 178 accommodates the proximal end 186 of the manifold 12*b* including threads 182 located along and about the proximal portion of the cavity body 158 of the manifold 12*b*. Also included in the hemostasis nut 168 is an annular lip 184 which can be utilized for snap engagement of the introducer 136 or other particular styles or types of introducers as required, as later described in detail. The hemostasis nut 168 threadingly engages the manifold 12*b* where the internal threads 174 of the hemostasis nut 168 engage and are advanced along the threads 182 of the manifold 12*b* until advancement of the hemostasis nut 168 is predeterminately stopped by impingement of the annular stop surface 180 against the proximal end 186 of the manifold 12*b*, whereby and whereupon the cylindrical boss 170 is brought to bear directly against the self-sealing hemostasis valve 64 which is in direct communication with the washer 134 to resultingly bring pressure to bear as required against the self-sealing hemostasis valve 64 and the washer 134 to foster and promote sealing of the hemostasis valve 64 with the cavity wall 160 of the cavity 156. A suitable adhesive can be applied to the internal threads 174 of the hemostasis nut 168 and to the threads 182 of the manifold 12*b* to ensure permanent fixation of the hemostasis nut 168 to the manifold 12*b*. Such engagement also ensures sealing of the self-sealing hemostasis valve 64 to a guidewire, such as previously described. Such engagements are shown in FIG. 25 and FIG. 26. The washer 134 and the self-sealing hemostasis valve 64 are captured in the cavity 156 by engagement of the hemostasis nut 168 to the cavity body 158 of the manifold 12*b*. Due to the similar geometrical configurations of the opposing faces and associated structure therebetween of the self-sealing hemostasis valve 64 and the washer 134, these components can be inserted into the cavity 156 without regard to the orientation of each.

Mode of Operation

FIG. 25 is a view in partial cross section of the assembled components of FIG. 24 shown loaded and engaged over and about and with the use of a guidewire 48. The introducer 136 is shown disengaged from its normal engaged position in the beveled passageway 172 for clarity. Such loading and engagement occurs much in the same fashion as previously described with reference to FIG. 10 or FIG. 19 where the proximal end of the guidewire 48 enters the tip 30 of the catheter tube 13 and where the proximal guidewire tip is negotiated by the fluid jet emanator 82, the catheter tube 13, the tapered central passageway 54, and the orifice 166 which centers the guidewire 48 with the cavity extension 164 and with the components contained in the cavity 156. Such loading continues through the cavity extension 164, through the central passage 135 of the washer 134, and thence through the junction of the tips of the lobes 98*a*-98*n* which concurrently locate with the inboard portion of the slits 96*a*-96*n* of the self-sealing hemostasis valve 64 which, as previously described, can be oriented in either direction. Loading continues with the guidewire 48 exiting through the beveled passageway 172 of the hemostasis nut 168 and concentrically and co-located hollow shaft 138 of the introducer 136, as best shown in FIG. 26. Passage of the guidewire 48 through the junction of the tips of the lobes 98*a*-98*n* which concurrently locate with the inboard portion of the slits 96*a*-96*n* of the self-sealing hemostasis valve 64 causes the tips and areas immediately surrounding the tips of the lobes 98*a*-98*n* to sealingly and slidingly deform, distend, flex, conform or otherwise comply to and accommodate the profile of the guidewire 48. The guidewire 48 is shown in sealing and slidable engagement with the self-sealing hemostasis valve 64 where the pressure in the tapered central passageway 54 can be maintained at a setting which allows minimal leakage of fluids, such as blood or saline solution, proximally through the seal created between the self-sealing hemostasis valve 64 and the guidewire 48. Such pressure setting is determined by the position of the cylindrical boss 170 of the hemostasis nut 168 in relation to the self-sealing hemostasis valve 64, as described later in detail. The hemostasis nut 168 serves to keep the self-sealing hemostasis valve 64 and the washer 134 positioned without movement within the cavity 156 and to compress the components residing in the cavity 156 at a suitable level.

FIG. 26 is a fragmentary view in cross section of the proximal region of the manifold 12*b* illustrating the introducer 136 in normal engagement with the hemostasis nut 168 and where the hemostasis nut 168 is in fixed nonadjustable engagement with the proximal end 186 located at the proximal region of the manifold 12*b*. The self-sealing hemostasis valve 64 provides for sealing which is nonadjustable about guidewire 48 in a manner as previously described dependent on the degree of compression applied to the self-sealing hemostasis valve 64 by the fixed position of the hemostasis nut 168. Compression of the self-sealing hemostasis valve 64 and of the washer 134 is influenced by the pressure applied thereto by the cylindrical boss 170 extending from the interior of the hemostasis nut 168. Such pressure is determined by the relationship of the longitudinal position of the hemostasis nut 168 with respect to the proximal end 186 of the manifold 12*b* where the proximal end 186 impinges the annular stop surface 180 to influence such a relationship. If during fabrication the proximal end 186 is of a lengthened dimension proximally, the hemostasis nut 168 would correspondingly be located in a position more proximal, thereby applying less compressive force applied by the cylindrical boss 170 upon the self-sealing hemostasis valve 64 and the washer 134, thereby decreasing the sealing capabilities against the guidewire 48 and against the cavity wall 160 of the cavity 156. Conversely, if during fabrication the proximal end 186 is of a shortened dimension distally, the hemostasis nut 168 would correspondingly be located in a position more distal, thereby applying more compressive force by the cylindrical boss 170 upon the self-sealing hemostasis valve 64 and the washer 134, thereby increasing the sealing capabilities against the guidewire 48 and against the cavity wall 160 of the cavity 156. The annular ring 142 around and about the hollow shaft 138 of the introducer 136 snappingly engages the annular lip 184 of the beveled passageway 172 to capture hollow shaft 138 of the introducer 136 within the beveled passageway 172, whereby the introducer 136 is positioned as shown for normal use where the distal end of the introducer 136 is in close proximity to the self-sealing hemostasis valve 64.

Figure 27:
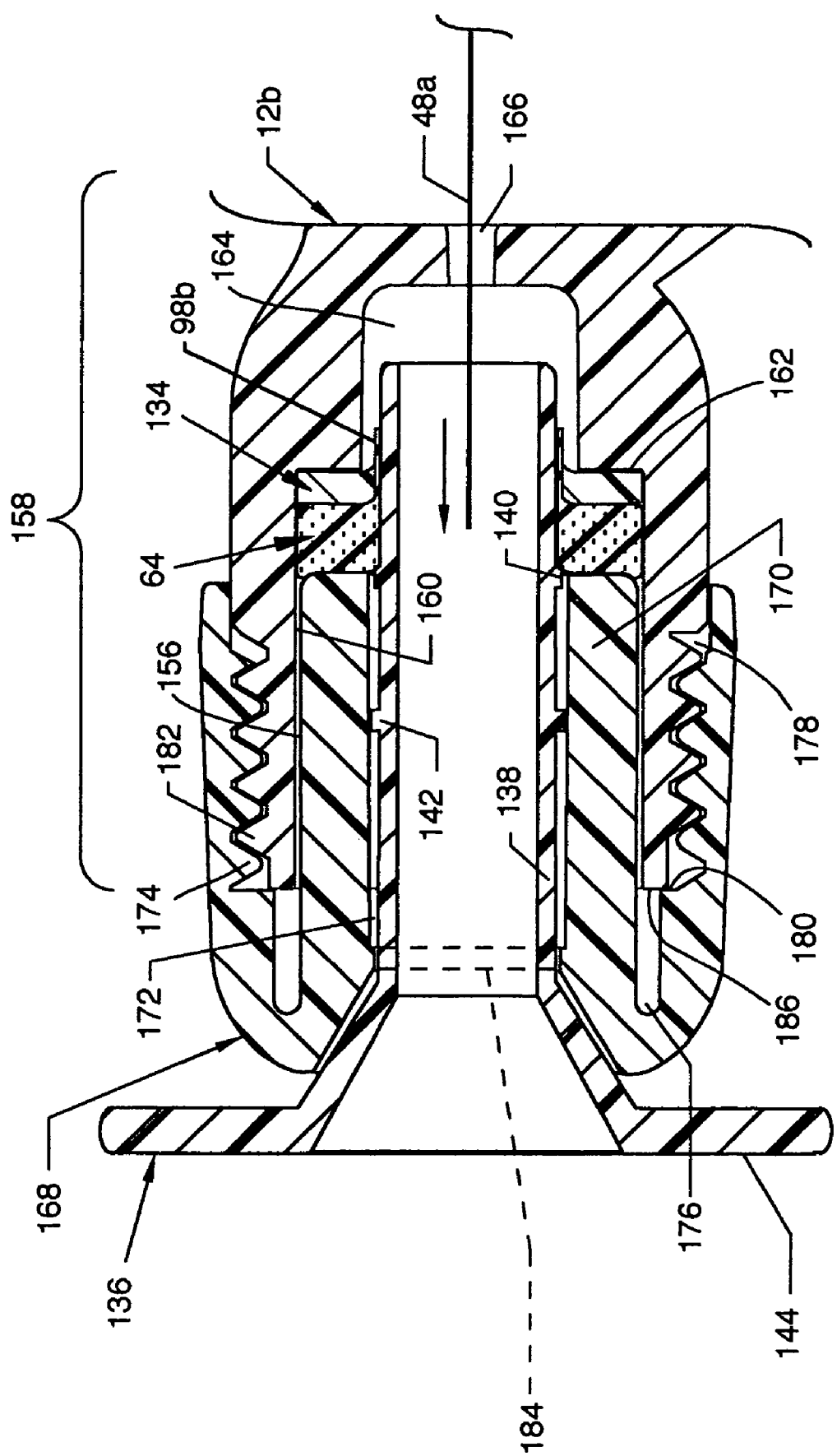
FIG. 27 is a view like FIG. 26 illustrating the function of the introducer to perform alternate functions as required either to bleed air out of the manifold or to aid guidewire movement through the self-sealing hemostasis valve.

FIG. 27 is a view like FIG. 26 illustrating the function of the introducer 136 to perform alternate functions as required either to bleed air or fluids out of the manifold 12*b* or to aid guidewire movement through the self-sealing hemostasis valve 64. To achieve such usefulness, the actuating handle 144 of the introducer 136 is manually pushed in a distal direction to force the distal end of the hollow shaft 138 towards and through the slits 96*a*-96*n* of the self-sealing hemostasis valve 64 and through the central passage 135 of the washer 134. Such entry into and through the self-sealing hemostasis valve 64 flexes, deforms and distends the lobes 98*a*-98*n* apart and in a distal direction to render the sealing capability against a guidewire, such as guidewire 48, ineffective, as well as slightly deforming the washer 134. The distal portion of the introducer 136 is accommodated by the cavity extension 164 during actuation of the introducer 136 in a distal direction. The ability to spread or open the tips of the lobes 98*a*-98*n* is useful for use with an alternate guidewire, such as guidewire 48*a*, of a thinner or more flexible nature where the reduced thickness or increased flexibility thereof decreases or hinders the ability of the alternate guidewire 48*a* to successfully navigate, negotiate or pass through the lobes 98*a*-98*n* in their normal sealed position. In such state, any air of a pressure higher than ambient in the tapered central passageway 54 and connecting passages or tubes or other pertinent pressure carrying structures is vented to ambient through the hollow shaft 138 of the introducer 136. As readily seen in the illustration, the introducer 136 provides a relatively large passageway through the hollow shaft 138 for introduction of the proximal end of an alternate guidewire 48*a*, or the guidewire 48, for passage therethrough. The proximal end of the alternate guidewire 48*a* is aligned to the hollow shaft 138 by a taper 54*a* (FIG. 25) at the proximal end of the tapered central passageway 54 adjacent to the orifice 166. The introducer 136, having been manually positioned as shown, remains held in that position by the engagement to the flexed, deformed and distended lobes 98*a*-98*n* of the self-sealing hemostasis valve 64. Subsequent to passage of the proximal end of the guidewire 48*a* to a position proximal to the flexed, distended and deformed self-sealing hemostasis valve 64, the introducer 136 can be manually retarded proximally to the position shown in FIG. 26 to disengage from intimate contact with the self-sealing hemostasis valve 64, whereupon a seal is established with the guidewire 48*a* (or guidewire 48) and the self-sealing hemostasis valve 64 regains sealing qualities relating to the guidewire 48*a* (or guidewire 48) and cavity 156, such as previously described.

Figure 28:
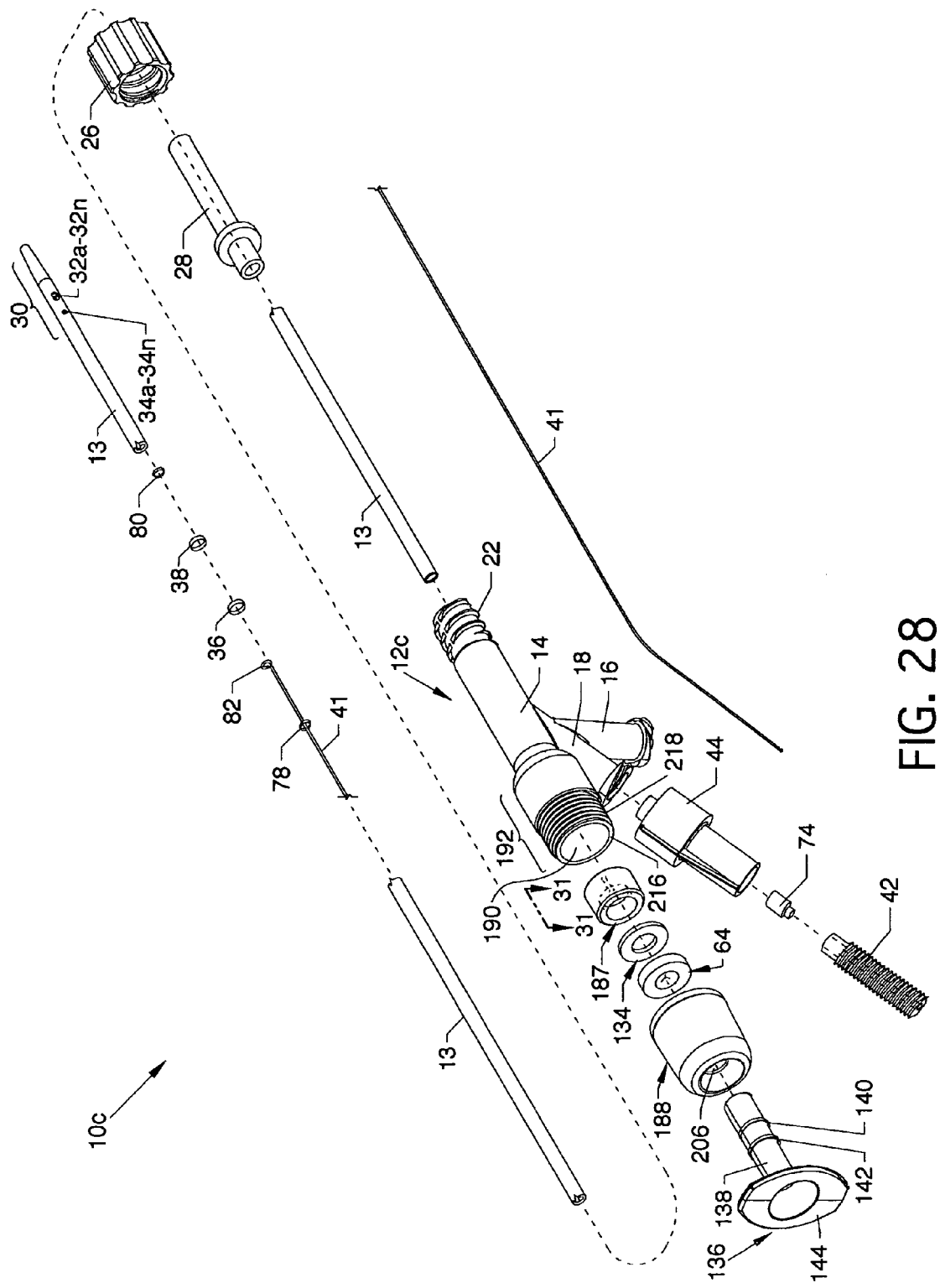
FIG. 28, a third alternate embodiment, is an isometric exploded view of a thrombectomy catheter device having a self-sealing hemostasis valve.
Figure 29:
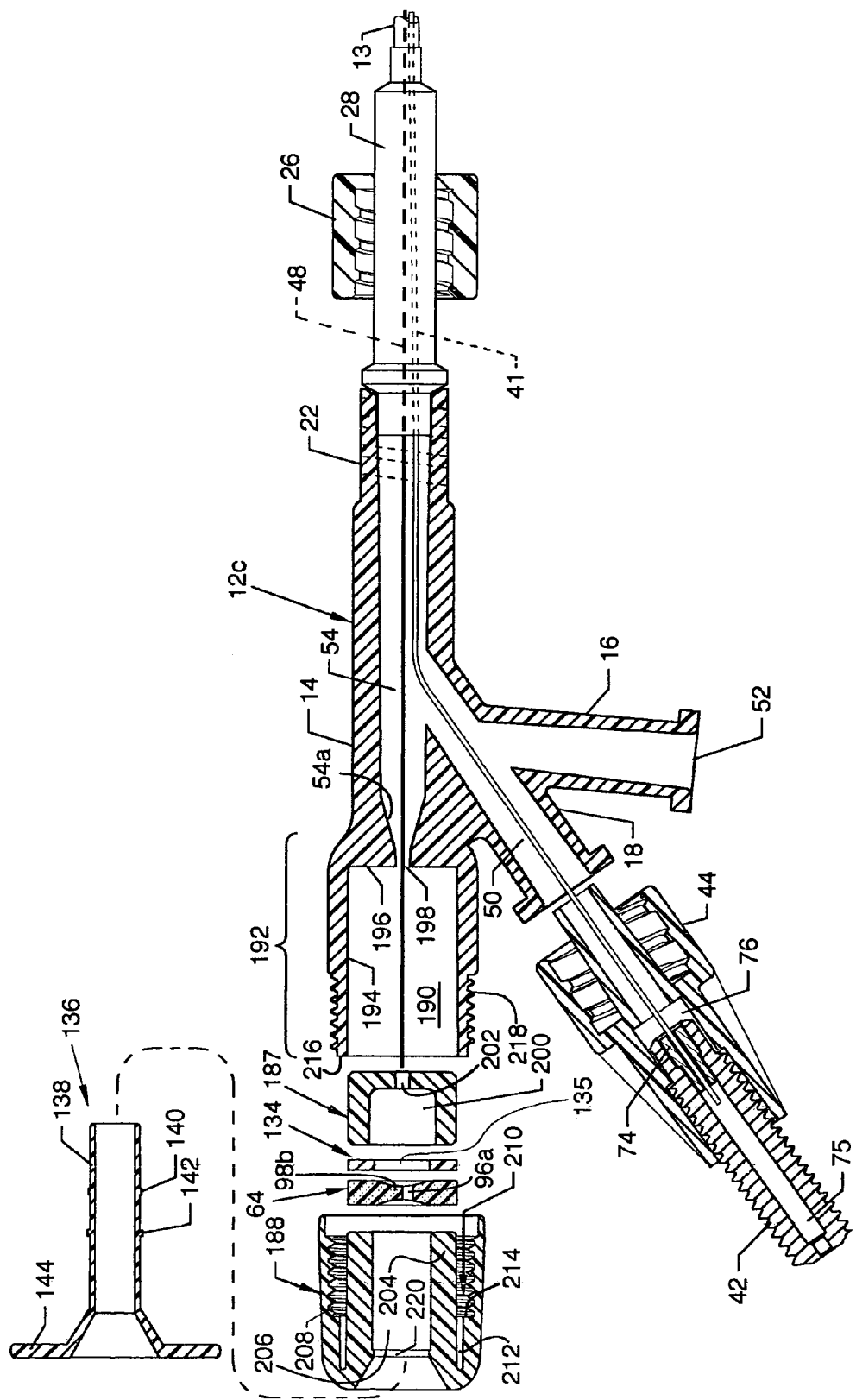
FIG. 29 is an exploded view in partial cross section of the components of the third alternate embodiment thrombectomy catheter device having a self-sealing hemostasis valve.

FIG. 28, a third alternate embodiment, is an isometric exploded view of a thrombectomy catheter device having a self-sealing hemostasis valve 10*c*, and FIG. 29 is an exploded view in partial cross section of the components of the third alternative embodiment thrombectomy catheter device having a self-sealing hemostasis valve 10*c*. The third alternate embodiment provides a thrombectomy catheter device having a self-sealing hemostasis valve 10*c* which features a cavity insert 187 in addition to a nonadjustable hemostasis nut 188 fixed over and about the proximal region of a manifold 12*c*. The thrombectomy catheter device having a self-sealing hemostasis valve 10*c* utilizes a large number of the components, structures, and features of the previously described thrombectomy catheter devices having a self-sealing hemostasis valve 10, 10*a* and 10*b*, and also operates in a somewhat similar fashion, but includes a different arrangement and/or type of components that align within and/or which can be associated with and which can be accommodated internally by an alternately configured cavity 190 located in a cavity body 192 of the manifold 12*c*. The cavity 190 is, for the most part, tubular in shape, including a tubular cavity wall 194 and a planar surface 196 which is annular and circular and which intersects the tubular cavity wall 194. The cavity insert 181, which aligns in the cavity 190, includes a centrally located recess 200 which is cylindrical in shape and a passage 202 aligned with and common to the recess 200. An orifice 198 is common to the cavity 190 and to the tapered central passageway 54 located central to the central tubular body 14. The cavity 190 accommodates, in order adjacent to planar surface 196, the cavity insert 187, the flexible washer 134 of TEFLON® or other suitable flexible material having the central passage 135 and the self-sealing hemostasis valve 64, previously described. The washer 134 functions as a low friction spacer to reduce rotational frictional binding to maintain the proper shape of the self-sealing hemostasis valve 64 when the hemostasis nut 168 is tightened. The washer 134 provides for stabilization with the introducer 136.

Figure 31:
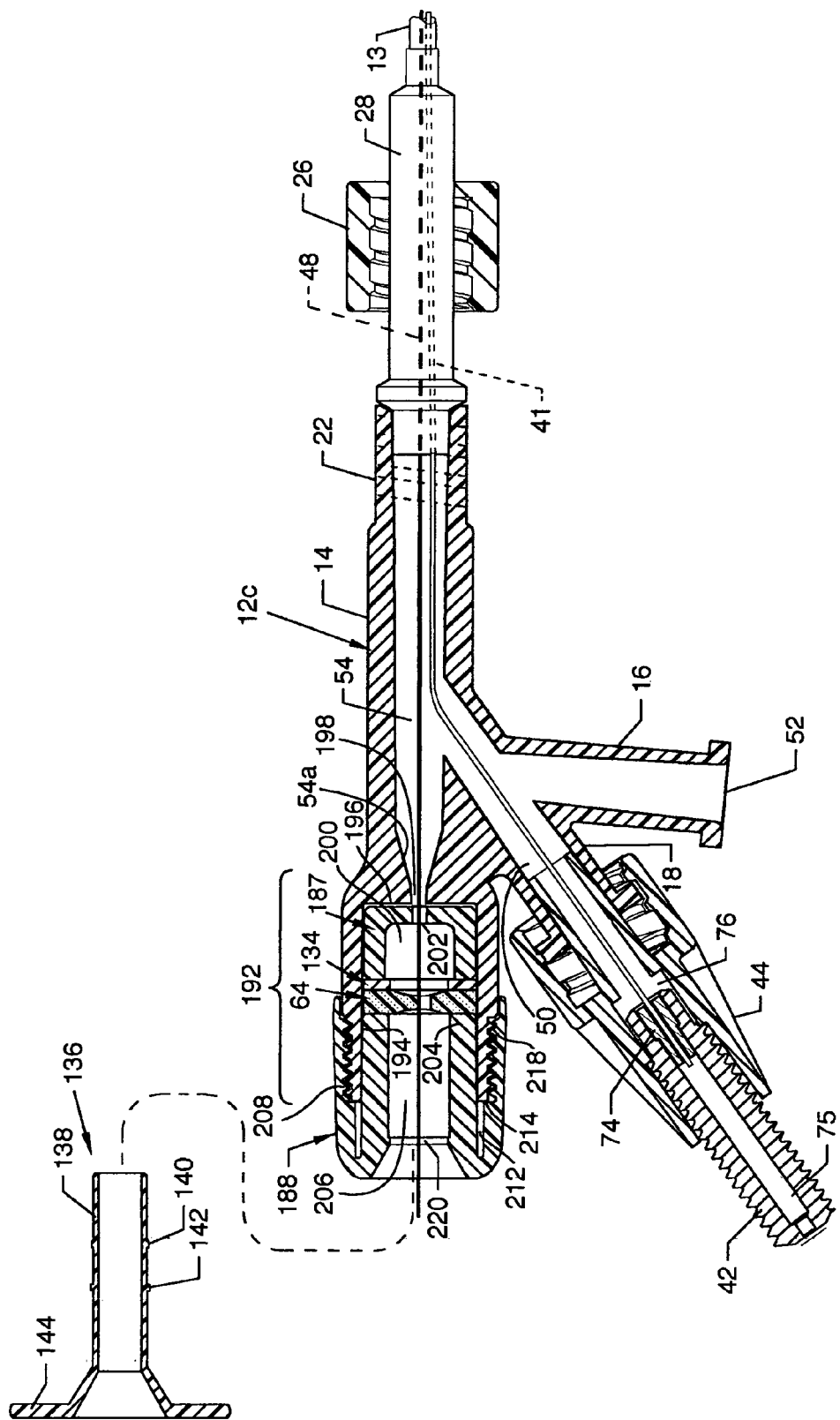
FIG. 31 is a view in partial cross section of the assembled components of the third alternate embodiment shown over and about and with the use of a guidewire and showing the introducer detached.
Figure 32:
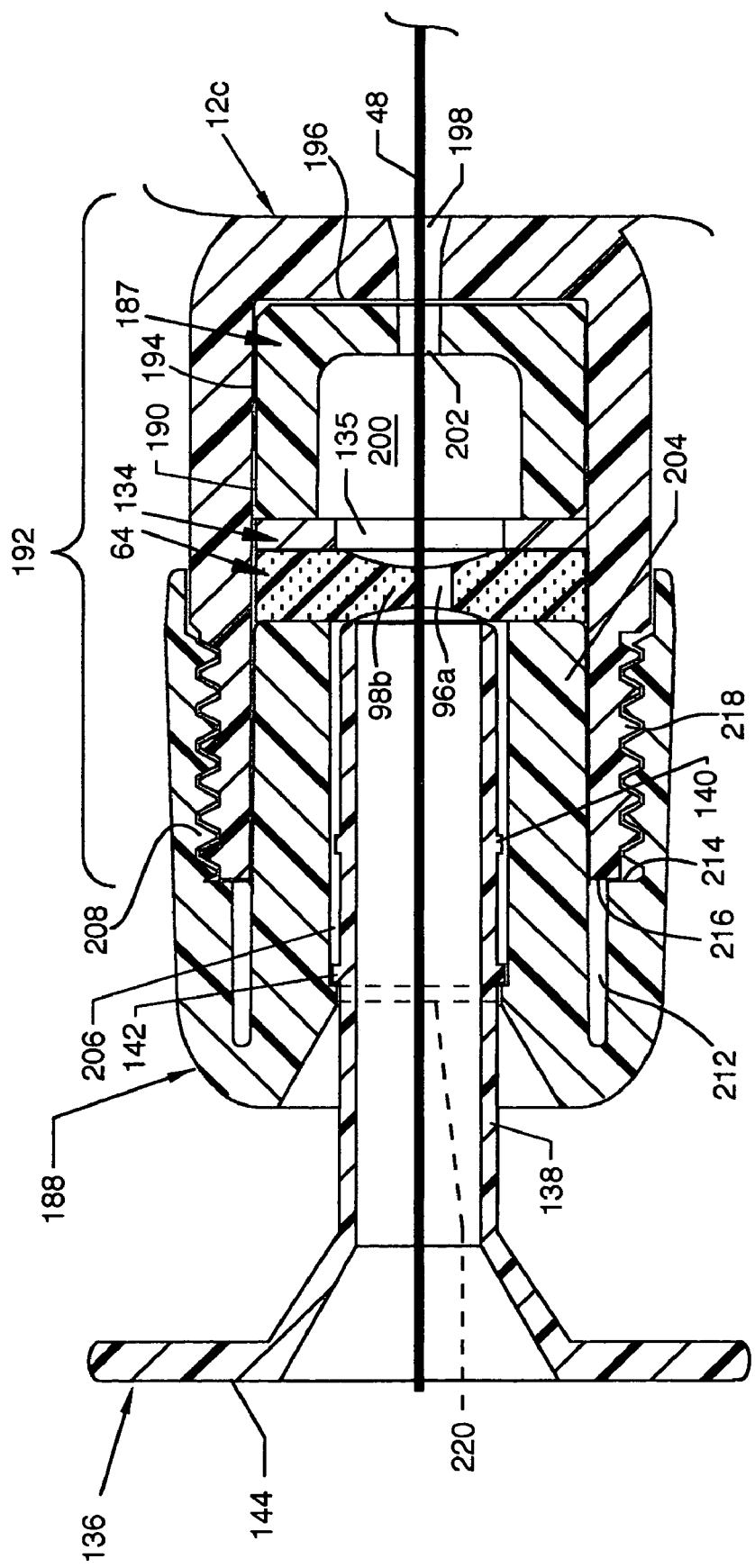
FIG. 32 is a fragmentary view in cross section of the proximal region of the manifold of the third alternate embodiment illustrating the introducer in normal engagement with the hemostasis nut and where the hemostasis nut is in fixed nonadjustable engagement with the proximal region of the manifold.

Also provided as part of the third alternate embodiment is the introducer 136, previously described, having a hollow shaft 138, annular rings 140 and 142 about the hollow shaft 138, and an actuating handle 144 which aligns in hemostasis nut 188. The hemostasis nut 188 includes a centrally located cylindrical boss 204, a beveled passageway 206 extending through and in part forming the cylindrical boss 204, and internal threads 208 distanced from the cylindrical boss 204 by a distally located space 210 extending along the internal threads 208 and along the distal portion of the cylindrical boss 204. A proximally located space 212 is located adjacent to the distally located space 210, and an annular stop surface 214 is located between the proximal region of the internal threads 208 and the distal region of the proximally located space 212. The distally located space 210 accommodates the proximal end 216 of the manifold 12*c* including threads 218 located along and about the proximal portion of the cavity body 192 of the manifold 12c. Also included in the hemostasis nut 188 is an annular lip 220 which can be utilized for snap engagement of the introducer 136 or other particular styles or types of introducers as required, as later described in detail. The hemostasis nut 188 threadingly engages the manifold 12c where the internal threads 208 of the hemostasis nut 188 engage and are advanced along the threads 218 of the manifold 12c until advancement of the hemostasis nut 188 is predeterminately stopped by the annular stop surface 214, whereby and whereupon the cylindrical boss 204 is brought to bear directly against the self-sealing hemostasis valve 64 which is in direct communication with the washer 134 to resultingly bring pressure to bear as required against the self-sealing hemostasis valve 64 and the washer 134 to foster and promote sealing of the hemostasis valve 64 with the cavity wall 194 of the cavity 190. A suitable adhesive can be applied to the internal threads 208 of the hemostasis nut 188 and to the threads 218 of the manifold 12c to ensure permanent fixation of the hemostasis nut 188 to the manifold 12c. Such engagement also ensures sealing of the self-sealing hemostasis valve 64 to a guidewire, such as previously described. Such engagements are shown in FIG. 31 and FIG. 32. The cavity insert 187, the washer 134, and the self-sealing hemostasis valve 64 are captured in the cavity 190 by engagement of the hemostasis nut 188 to the cavity body 192 of the manifold 12c. Due to the similar geometrical configurations of the opposing faces and associated structure therebetween of the self-sealing hemostasis valve 64 and the washer 134, these components can be inserted into the cavity 190 without regard to the orientation of each; however, the cavity insert 187 must be oriented as shown.

Figure 30:
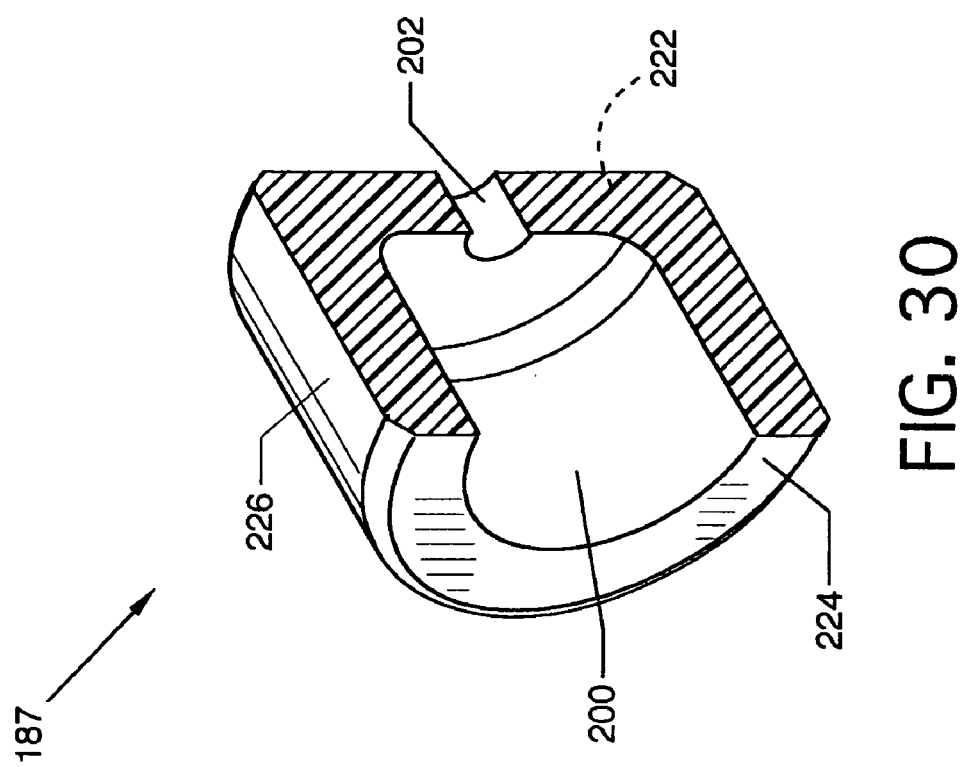
FIG. 30 is a proximal cross section end view of the cavity insert along line 31-31 of FIG. 28.

FIG. 30 is a proximal cross section end view of the cavity insert 187 along line 31-31 of FIG. 28. The cavity insert 187, which aligns in the cavity 190 of the cavity body 192, is fashioned and preferably constructed of a suitable polycarbonate but could be fashioned of aluminum or other suitable material, as required. The cavity insert 187 includes the centrally located recess 200 which is cylindrical in shape juxtaposing the passage 202. Also included are opposing circular-shaped faces 222 and 224 where face 224 is interrupted by the recess 200. A circumferential edge 226 aligns between the circular-shaped faces 222 and 224.

Mode of Operation

FIG. 31 is a view in partial cross section of the assembled components of FIG. 29 shown loaded and engaged over and about and with the use of a guidewire 48. The introducer 136 is shown disengaged from its normal engaged position in the beveled passageway 206 for the purpose of clarity. Such loading and engagement occurs much in the same fashion as previously described with reference to FIG. 10, FIG. 19 or FIG. 25 where the proximal end of the guidewire 48 enters the tip 30 of the catheter tube 13 and where the proximal guidewire tip is negotiated by the fluid jet emanator 82, the catheter tube 13, the tapered central passageway 54, and the orifice 198 which centers the guidewire 48 with the passage 202 and the recess 200 of the cavity insert 187 and with the components contained in the cavity 190. Such loading continues through the cavity insert 187, through the central passage 135 of the washer 134, and thence through the junction of the tips of the lobes 98a-98n which concurrently locate with the inboard portion of the slits 96a-96n of the self-sealing hemostasis valve 64 which, as previously described, can be oriented in either direction. Loading continues with the guidewire 48 exiting through the beveled passageway 206 of the hemostasis nut 188 and concentrically and co-located hollow shaft 138 of the introducer 136, as best shown in FIG. 32. Passage of the guidewire 48 through the junction of the tips of the lobes 98a-98n which concurrently locate with the inboard portion of the slits 96a-96n of the self-sealing hemostasis valve 64 causes the tips and areas immediately surrounding the tips of the lobes 98a-98n to sealingly and slidingly deform, distend, flex, conform or otherwise comply to and accommodate the profile of the guidewire 48. The guidewire 48 is shown in sealing and slidable engagement with the self-sealing hemostasis valve 64 where the pressure in the tapered central passageway 54 can be maintained at a setting which allows minimal leakage of fluids, such as blood or saline solution, proximally through the seal created between the self-sealing hemostasis valve 64 and the guidewire 48. Such pressure setting is determined by the position of the cylindrical boss 204 of the hemostasis nut 188 in relation to the self-sealing hemostasis valve 64, as described later in detail. The hemostasis nut 188 serves to keep the self-sealing hemostasis valve 64, the washer 134 and the cavity insert 187 positioned without movement within the cavity 190 and to compress the components residing in the cavity 190 at a suitable level.

FIG. 32 is a fragmentary view in cross section of the proximal region of the manifold 12c illustrating the introducer 136 in normal engagement with the hemostasis nut 188 and where the hemostasis nut 188 is in fixed nonadjustable engagement with the proximal end 216 located at the proximal region of the manifold 12c. The self-sealing hemostasis valve 64 provides for sealing which is nonadjustable about guidewire 48 in a manner as previously described dependent on the degree of compression applied to the self-sealing hemostasis valve 64 by the fixed position of the hemostasis nut 188. Compression of the self-sealing hemostasis valve 64 and of the washer 134 is influenced by the pressure applied thereto by the cylindrical boss 204 extending from the interior of the hemostasis nut 188. Such pressure is determined by the relationship of the longitudinal position of the hemostasis nut 188 with respect to the proximal end 216 of the manifold 12c where the proximal end 216 impinges the annular stop surface 214 to influence such a relationship. If during fabrication the proximal end 216 is of a lengthened dimension proximally, the hemostasis nut 188 would correspondingly be located in a position more proximal, thereby applying less compressive force applied by the cylindrical boss 204 upon the self-sealing hemostasis valve 64 and the washer 134, thereby decreasing the sealing capabilities against the guidewire 48 and against the cavity wall 194 of the cavity 190. Conversely, if during fabrication the proximal end 216 is of a shortened dimension distally, the hemostasis nut 188 would correspondingly be located in a position more distal, thereby applying more compressive force by the cylindrical boss 204 upon the self-sealing hemostasis valve 64 and the washer 134, thereby increasing the sealing capabilities against the guidewire 48 and against the cavity wall 194 of the cavity 190. The annular ring 142 around and about the hollow shaft 138 of the introducer 136 snappingly engages the annular lip 220 of the beveled passageway 206 to capture the hollow shaft 138 of the introducer 136 within the beveled passageway 206, whereby the introducer 136 is positioned as shown for normal use where the distal end of the introducer 136 is in close proximity to the self-sealing hemostasis valve 64.

Figure 33:
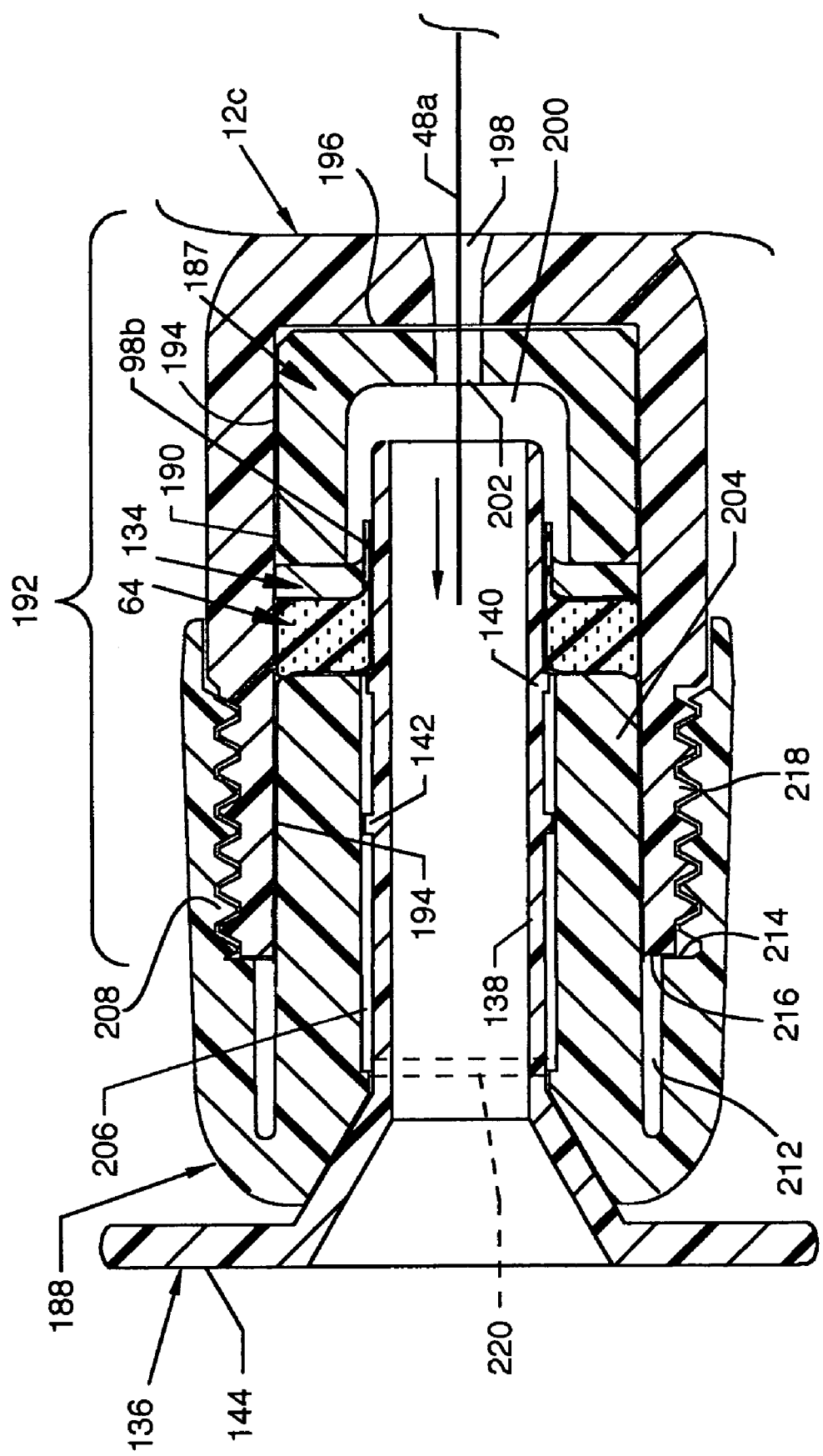
FIG. 33 is a view like FIG. 32 illustrating the function of the introducer to perform alternate functions as required either to bleed air out of the manifold or to aid guidewire movement through the self-sealing hemostasis valve.

FIG. 33 is a view like FIG. 32 illustrating the function of the introducer 136 to perform alternate functions as required either to bleed air or fluids out of the manifold 12c or to aid guidewire movement through the self-sealing hemostasis valve 64. To achieve such usefulness, the actuating handle 144 of the introducer 136 is manually pushed in a distal direction to force the distal end of the hollow shaft 138 towards and through the slits 96a-96n of the self-sealing hemostasis valve 64 and through the central passage 135 of the washer 134. Such entry into and through the self-sealing hemostasis valve 64 flexes, deforms and distends the lobes 98a-98n apart and in a distal direction to render the sealing capability against a guidewire, such as guidewire 48, ineffective, as well as slightly deforming the washer 134. The distal portion of the introducer 136 is accommodated by the recess 200 of the cavity insert 187 during actuation of the introducer 136 in a distal direction. The ability to spread or open the tips of the lobes 98a-98n is useful for use with an alternate guidewire, such as guidewire 48a, of a thinner or more flexible nature where the reduced thickness or increased flexibility thereof decreases or hinders the ability of the alternate guidewire 48a to successfully navigate, negotiate or pass through the lobes 98a-98n in their normal sealed position. In such state, any air of a pressure higher than ambient in the tapered central passageway 54 and connecting passages or tubes or other pertinent pressure carrying structures is vented to ambient through the hollow shaft 138 of the introducer 136. As readily seen in the illustration, the introducer 136 provides a relatively large passageway through the hollow shaft 138 for introduction of the proximal end of an alternate guidewire 48a, or the guidewire 48, for passage therethrough. The proximal end of the alternate guidewire 48a is aligned to the hollow shaft 138 by the taper 54a at the proximal end of the tapered central passageway 54 adjacent to the orifice 198. The introducer 136, having been manually positioned as shown, remains held in that position by the engagement to the flexed, deformed and distended lobes 98a-98n of the self-sealing hemostasis valve 64. Subsequent to passage of the proximal end of the guidewire 48a to a position proximal to the flexed, distended and deformed self-sealing hemostasis valve 64, the introducer 136 can be manually retarded proximally to the position shown in FIG. 32 to disengage from intimate contact with the self-sealing hemostasis valve 64, whereupon a seal is established with the guidewire 48a (or guidewire 48) and the self-sealing hemostasis valve 64 regains sealing qualities relating to the guidewire 48a (or guidewire 48) and cavity 190, such as previously described.

Figure 34:
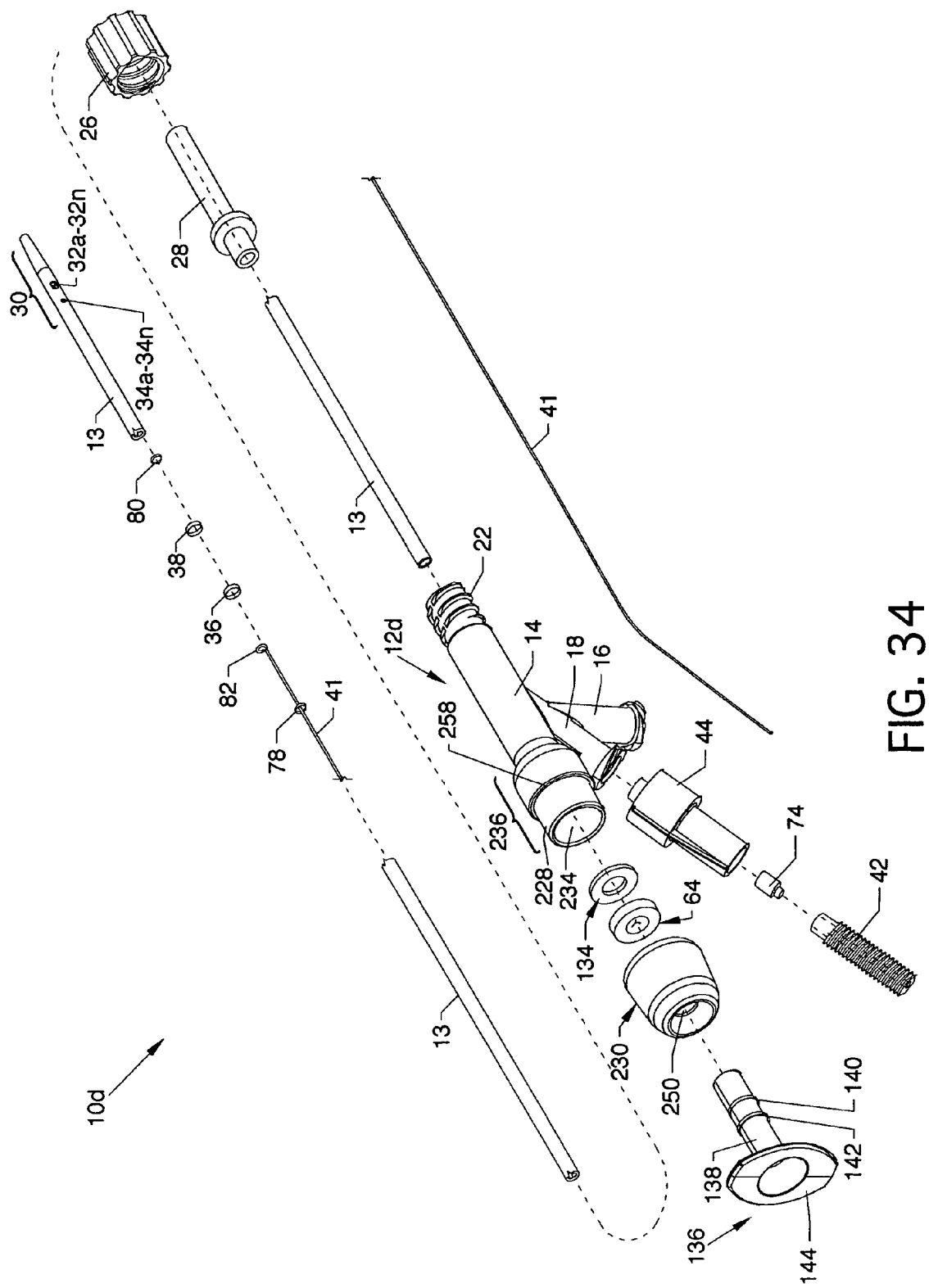
FIG. 34, a fourth alternate embodiment, is an isometric exploded view of a thrombectomy catheter device having a self-sealing hemostasis valve.
Figure 35:
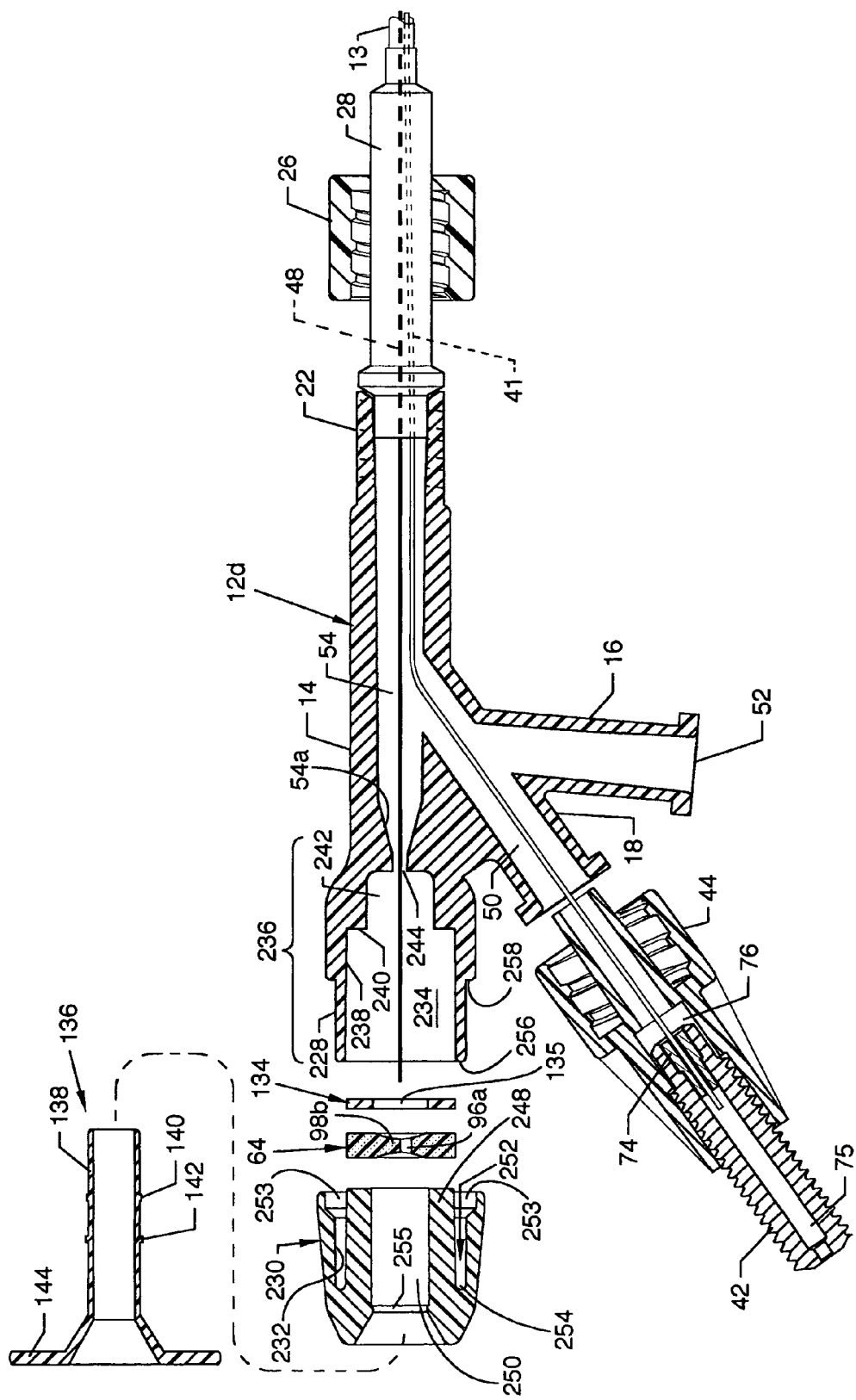
FIG. 35 is an exploded view in partial cross section of the components of the fourth alternate embodiment thrombectomy catheter device having a self-sealing hemostasis valve.

FIG. 34, a fourth alternate embodiment, is an isometric exploded view of a thrombectomy catheter device having a self-sealing hemostasis valve 10d, and FIG. 35 is an exploded view in partial cross section of the components of the thrombectomy catheter device having a self-sealing hemostasis valve 10d. The fourth alternate embodiment provides a thrombectomy catheter device having a self-sealing hemostasis valve 10d which replaces the threads, such as threads 218, shown on the proximal region of a manifold 12c, as shown in FIG. 29, by a smooth cylindrical surface 228 in addition to a nonadjustable hemostasis nut 230 where the internal threads, such as internal threads 208 as shown in FIG. 29, are replaced by a smooth cylindrical surface 232. In this embodiment, the nonadjustable hemostasis nut 230 is adhesively fixed to the smooth cylindrical surface 228 at a predetermined position to cause a desired longitudinal force to maintain a leak-proof seal in the range of 25 to 50 psi or at other desired pressure values. The thrombectomy catheter device having a self-sealing hemostasis valve 10d utilizes a large number of the components, structures, and features of the previously described thrombectomy catheter devices having a self-sealing hemostasis valve 10, 10a, 10b and 10c and also operates in a somewhat similar fashion, but includes a different arrangement and/or type of components that align within and/or which can be associated with and which can be accommodated internally by a cavity 234 located in a cavity body 236 of a manifold 12d. The cavity 234 is, for the most part, tubular in shape, including a tubular cavity wall 238 and a planar surface 240 which is annular and circular and which intersects the tubular cavity wall 238. A cavity extension 242, for the most part being tubular, extends distally from the cavity 234 beginning at the planar surface 240 to intersect and connect with an orifice 244 which is common to the cavity 234 and to the tapered central passageway 54 located central to the central tubular body 14. The cavity 234 accommodates, in order adjacent to planar surface 240, the flexible washer 134 of TEFLON® or other suitable flexible material having the central passage 135 and the self-sealing hemostasis valve 64, previously described. The washer 134 functions as a low friction spacer to reduce rotational frictional binding to maintain the proper shape of the self-sealing hemostasis valve 64 when the hemostasis nut 230 is tightened. The washer 134 provides for stabilization with the introducer 136.

Figure 36:
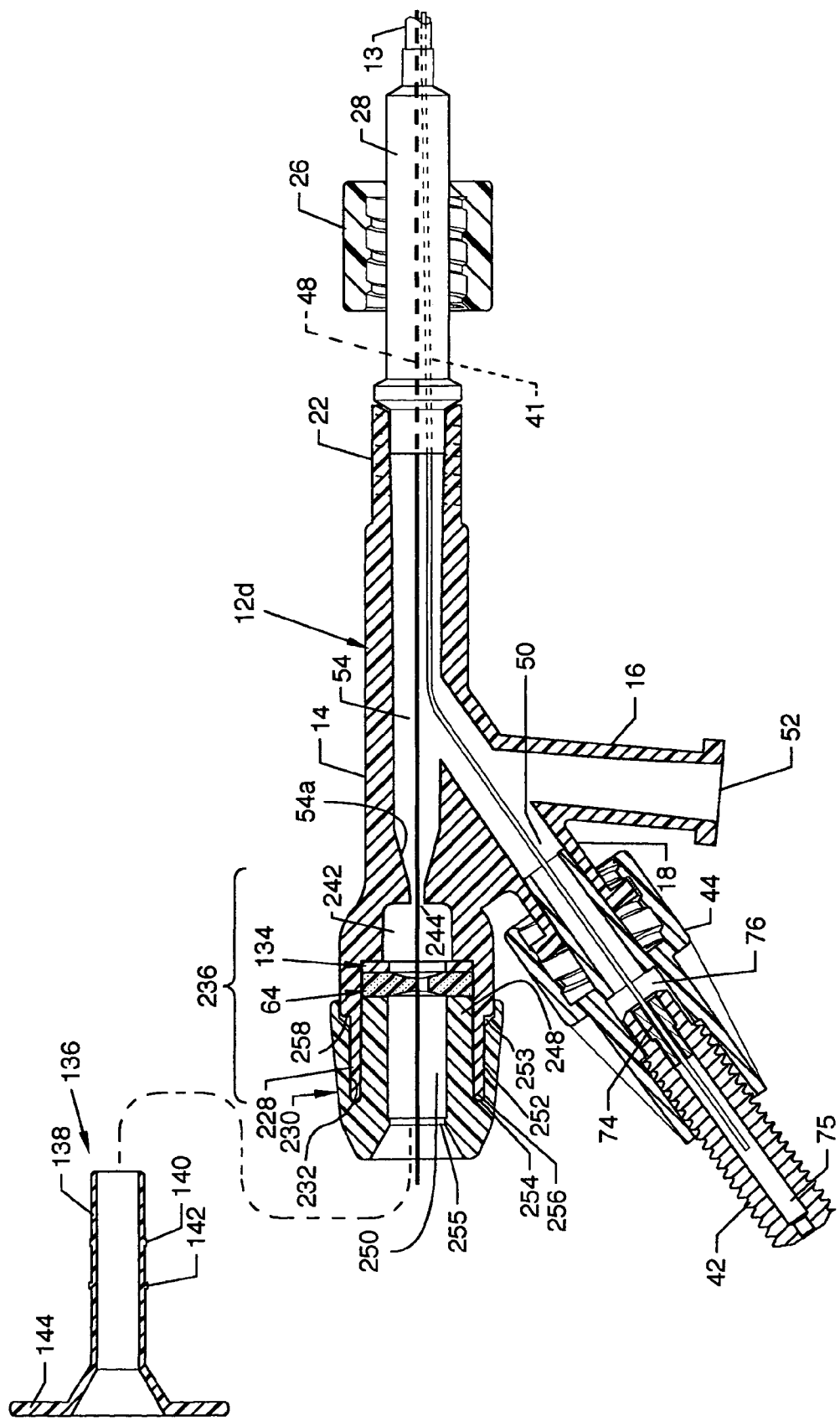
FIG. 36 is a view in partial cross section of the assembled components of the fourth alternate embodiment shown over and about and with the use of a guidewire and showing the introducer detached.
Figure 37:
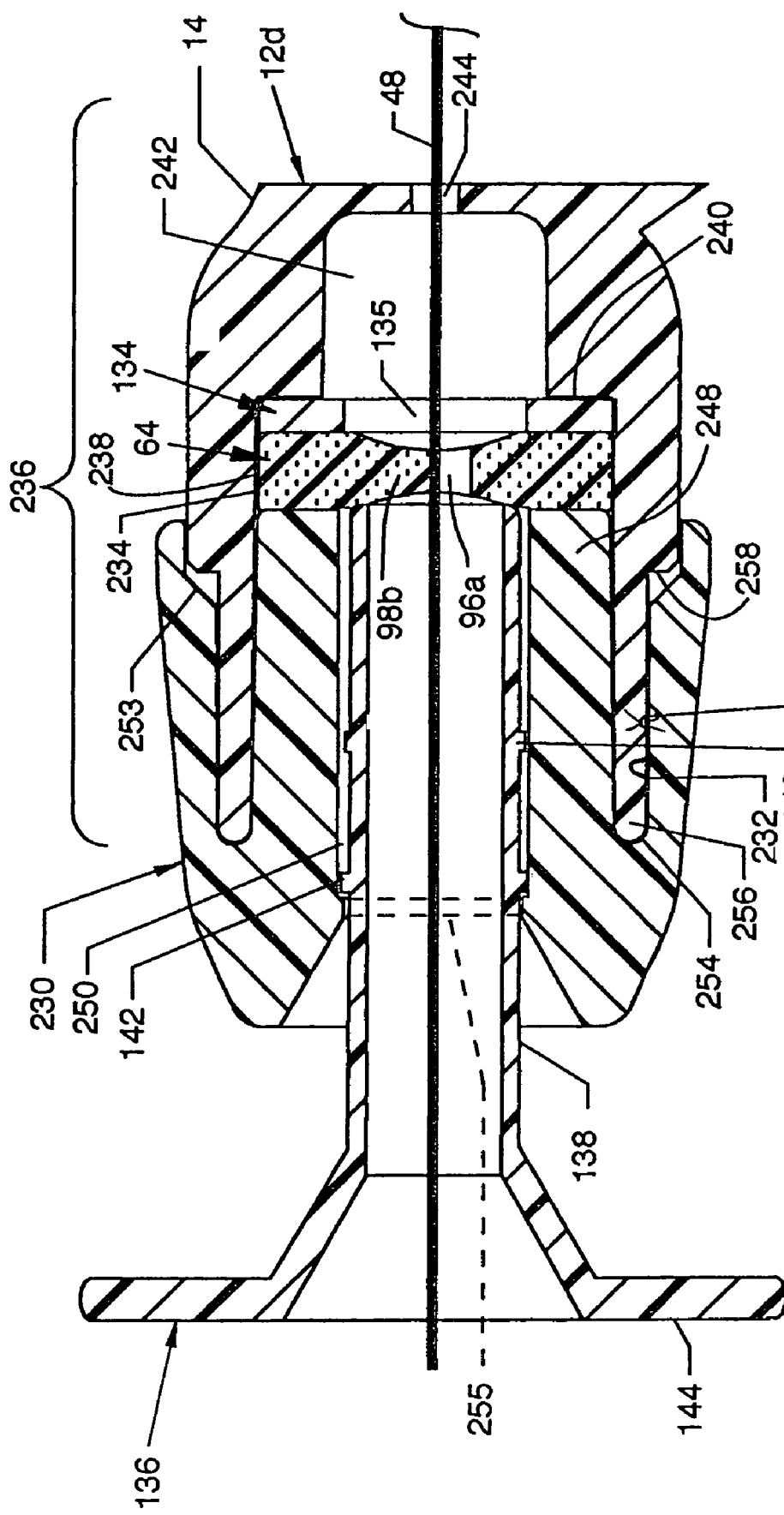
FIG. 37 is a fragmentary view in cross section of the proximal region of the manifold of the fourth alternate embodiment illustrating the introducer in normal engagement with the hemostasis nut and where the hemostasis nut is in fixed nonadjustable engagement with the proximal region of the manifold.

Also provided as part of the fourth alternate embodiment is the introducer 136, previously described, having a hollow shaft 138, annular rings 140 and 142 about the hollow shaft 138, and an actuating handle 144 which aligns in hemostasis nut 230. The hemostasis nut 230 includes a centrally located cylindrical boss 248, a beveled passageway 250 extending through and in part forming the cylindrical boss 248, and a smooth cylindrical surface 232 distanced from the cylindrical boss 248 by a proximally located space 252 extending between the smooth cylindrical surface 232 and the cylindrical boss 248. A distally located space 253 is located adjacent to the proximally located space 252 and an annular stop surface 254 is located at the proximal region of the proximally located space 252. The proximally located space 252 accommodates the proximal end 256 of the manifold 12d including the smooth cylindrical surface 228 located along and about the proximal region of the cavity body 236 of the manifold 12d. Also included in the hemostasis nut 230 is an annular lip 255 which can be utilized for snap engagement of the introducer 136 or other particular styles or types of introducers as required, as later described in detail. The hemostasis nut 230 engages the manifold 12d where the smooth cylindrical surface 232 of the hemostasis nut 230 engages the smooth cylindrical surface 228 of the manifold 12d until advancement of the hemostasis nut 230 is predeterminately stopped by impingement of the proximal end 256 of the manifold 12d by the annular stop surface 254 of the hemostasis nut 230, whereby and whereupon the cylindrical boss 248 is brought to bear directly against the self-sealing hemostasis valve 64 which is in direct communication with the washer 134 to resultingly bring pressure to bear as required against the self-sealing hemostasis valve 64 and the washer 134 to foster and promote sealing of the hemostasis valve 64 with the cavity wall 238 of the cavity 234 optionally, and with suitable dimensioning, additional engagement of the hemostasis nut 230 to the manifold 12d can be obtained by engagement of the walls or other surfaces of the distally located space 253 of the hemostasis nut 230 with an annular shoulder 258 located midway along the cavity body 236 at the distal end of the smooth cylindrical surface 228 which can also act as a stop. A suitable adhesive can be applied to the smooth cylindrical surface 232 of the hemostasis nut 230 and to the smooth cylindrical surface 228 of the manifold 12d to ensure permanent fixation of the hemostasis nut 230 to the manifold 12d. Such engagements also ensure sealing of the self-sealing hemostasis valve 64 to a guidewire, such as previously described. Such engagements are shown in FIG. 36 and FIG. 37. The washer 134 and the self-sealing hemostasis valve 64 are captured in the cavity 234 by engagement of the hemostasis nut 230 to the cavity body 236 of the manifold 12*d*. Due to the similar geometrical configurations of the opposing faces and associated structure therebetween of the self-sealing hemostasis valve 64 and the washer 134, these components can be inserted into the cavity 234 without regard to the orientation of each.

Mode of Operation

FIG. 36 is a view in partial cross section of the assembled components of FIG. 35 shown loaded and engaged over and about and with the use of a guidewire 48. The introducer 136 is shown disengaged from its normal engaged position in the beveled passageway 250 for the purpose of clarity. Such loading and engagement occurs much in the same fashion as previously described with reference to FIG. 10, FIG. 19, FIG. 25 or FIG. 31 where the proximal end of the guidewire 48 enters the tip 30 of the catheter tube 13 and where the proximal guidewire tip is negotiated by the fluid jet emanator 82, the catheter tube 13, the tapered central passageway 54, and the orifice 244 which centers the guidewire 48 with the cavity extension 242 and with the components contained in the cavity 234. Such loading continues through the cavity extension 242, through the central passage 135 of the washer 134, and thence through the junction of the tips of the lobes 98*a*-98*n* which concurrently locate with the inboard portion of the slits 96*a*-96*n* of the self-sealing hemostasis valve 64 which, as previously described, can be oriented in either direction. Loading continues with the guidewire 48 exiting through the beveled passageway 250 of the hemostasis nut 230 and concentrically and co-located hollow shaft 138 of the introducer 136, as best shown in FIG. 37. Passage of the guidewire 48 through the junction of the tips of the lobes 98*a*-98*n* which concurrently locate with the inboard portion of the slits 96*a*-96*n* of the self-sealing hemostasis valve 64 causes the tips and areas immediately surrounding the tips of the lobes 98*a*-98*n* to sealingly and slidingly deform, distend, flex, conform or otherwise comply to and accommodate the profile of the guidewire 48. The guidewire 48 is shown in sealing and slidable engagement with the self-sealing hemostasis valve 64 where the pressure in the tapered central passageway 54 can be maintained at a setting which allows minimal leakage of fluids, such as blood or saline solution, proximally through the seal created between the self-sealing hemostasis valve 64 and the guidewire 48. Such a pressure setting is determined by the position of the cylindrical boss 248 of the hemostasis nut 230 in relation to the self-sealing hemostasis valve 64, as described later in detail. The hemostasis nut 230 serves to keep the self-sealing hemostasis valve 64 and the washer 134 positioned without movement within the cavity 234 and to compress the components residing in the cavity 234 at a suitable level.

FIG. 37 is a fragmentary view in cross section of the proximal region of the manifold 12*d* illustrating the introducer 136 in normal engagement with the hemostasis nut 230 and where the hemostasis nut 230 is in fixed nonadjustable engagement with the proximal end 256 located at the proximal region of the manifold 12*d*. The self-sealing hemostasis valve 64 provides for sealing which is nonadjustable about guidewire 48 in a manner as previously described dependent on the degree of compression applied to the self-sealing hemostasis valve 64 by the fixed position of the hemostasis nut 230. Compression of the self-sealing hemostasis valve 64 and of the washer 134 is influenced by the pressure applied thereto by the cylindrical boss 248 extending from the interior of the hemostasis nut 230. Such pressure is determined by the relationship of the longitudinal position of the hemostasis nut 230 with respect to the proximal end 256 of the manifold 12*d* where the proximal end 256 impinges the annular stop surface 254 to influence such a relationship. If during fabrication the proximal end 256 is of a lengthened dimension proximally, the hemostasis nut 230 would correspondingly be located in a position more proximal, thereby applying less compressive force applied by the cylindrical boss 248 upon the self-sealing hemostasis valve 64 and the washer 134, thereby decreasing the sealing capabilities against the guidewire 48 and against the cavity wall 238 of the cavity 234. Conversely, if during fabrication the proximal end 256 is of a shortened dimension distally, the hemostasis nut 230 would correspondingly be located in a position more distal, thereby applying more compressive force by the cylindrical boss 248 upon the self-sealing hemostasis valve 64 and the washer 134, thereby increasing the sealing capabilities against the guidewire 48 and against the cavity wall 238 of the cavity 234. The annular ring 142 around and about the hollow shaft 138 of the introducer 136 snappingly engages the annular lip 255 of the beveled passageway 250 to capture the hollow shaft 138 of the introducer 136 within the beveled passageway 250, whereby the introducer 136 is positioned as shown for normal use where the distal end of the introducer 136 is in close proximity to the self-sealing hemostasis valve 64.

Figure 38:
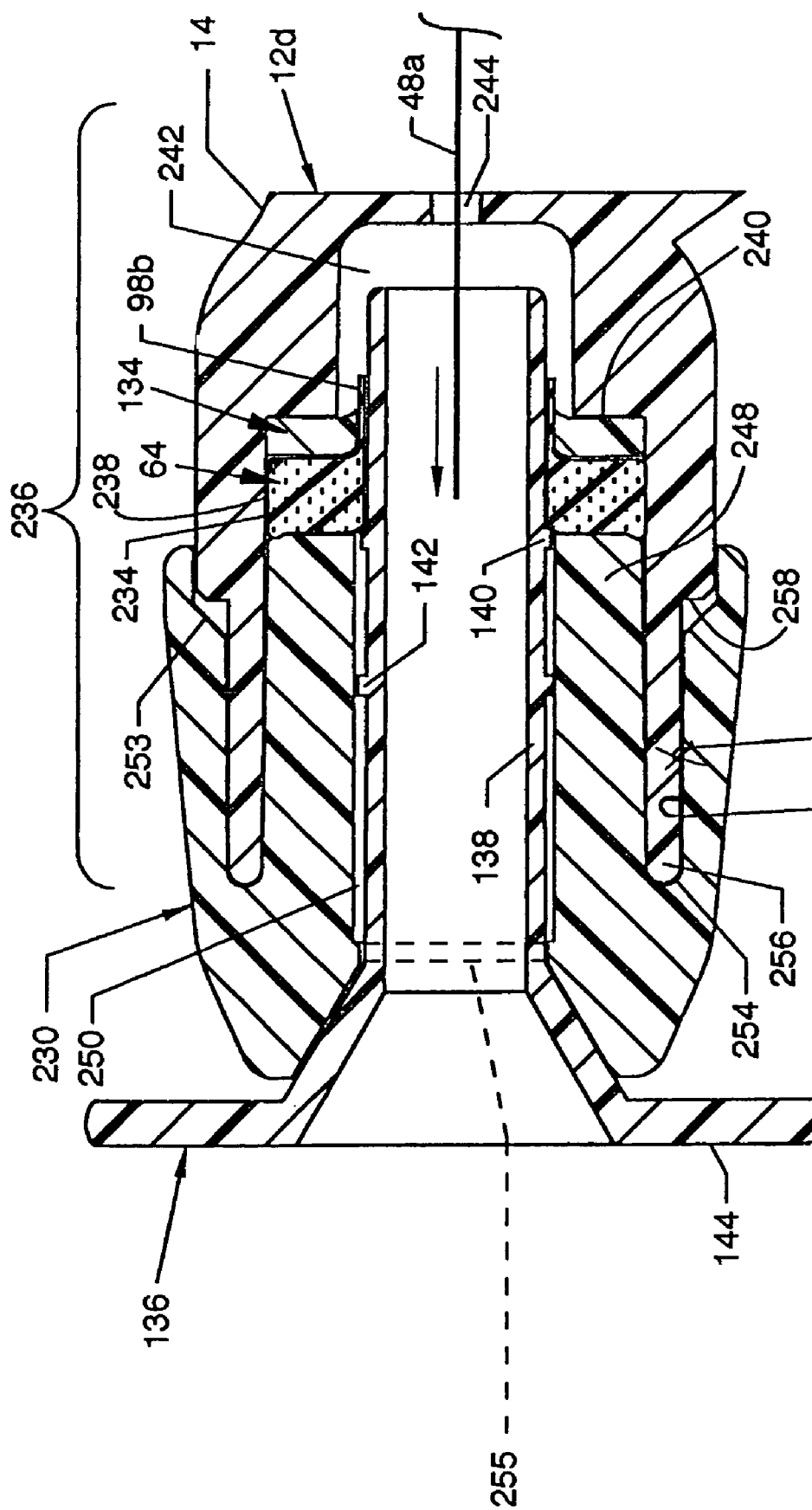
FIG. 38 is a view like FIG. 37 illustrating the function of the introducer to perform alternate functions as required either to bleed air out of the manifold or to aid guidewire movement through the self-sealing hemostasis valve.

FIG. 38 is a view like FIG. 37 illustrating the function of the introducer 136 to perform alternate functions as required either to bleed air or fluids out of the manifold 12*d* or to aid guidewire movement through the self-sealing hemostasis valve 64. To achieve such usefulness, the actuating handle 144 of the introducer 136 is manually pushed in a distal direction to force the distal end of the hollow shaft 138 towards and through the slits 96*a*-96*n* of the self-sealing hemostasis valve 64 and through the central passage 135 of the washer 134. Such entry into and through the self-sealing hemostasis valve 64 flexes, deforms and distends the lobes 98*a*-98*n* apart and in a distal direction to render the sealing capability against a guidewire, such as guidewire 48, ineffective, as well as slightly deforming the washer 134. The distal portion of the introducer 136 is accommodated by the cavity extension 242 during actuation of the introducer 136 in a distal direction. The ability to spread or open the tips of the lobes 98*a*-98*n* is useful for use with an alternate guidewire, such as guidewire 48*a*, of a thinner or more flexible nature where the reduced thickness or increased flexibility thereof decreases or hinders the ability of the alternate guidewire 48*a* to successfully navigate, negotiate or pass through the lobes 98*a*-98*n* in their normal sealed position. In such state, any air of a pressure higher than ambient in the tapered central passageway 54 and connecting passages or tubes or other pertinent pressure carrying structures is vented to ambient through the hollow shaft 138 of the introducer 136. As readily seen in the illustration, the introducer 136 provides a relatively large passageway through the hollow shaft 138 for introduction of the proximal end of an alternate guidewire 48*a*, or the guidewire 48, for passage therethrough. The proximal end of the alternate guidewire 48*a* is aligned to the hollow shaft 138 by the taper 54*a* at the proximal end of the tapered central passageway 54 adjacent to the orifice 244. The introducer 136, having been manually positioned as shown, remains held in that position by the engagement to the flexed, deformed and distended lobes 98a-98n of the self-sealing hemostasis valve 64. Subsequent to passage of the proximal end of the guidewire 48a to a position proximal to the flexed, distended and deformed self-sealing hemostasis valve 64, the introducer 136 can be manually retarded proximally to the position shown in FIG. 37 to disengage from intimate contact with the self-sealing hemostasis valve 64, whereupon a seal is established with the guidewire 48a (or guidewire 48) and the self-sealing hemostasis valve 64 regains sealing qualities relating to the guidewire 48a (or guidewire 48) and cavity 234, such as previously described.

Figure 39:
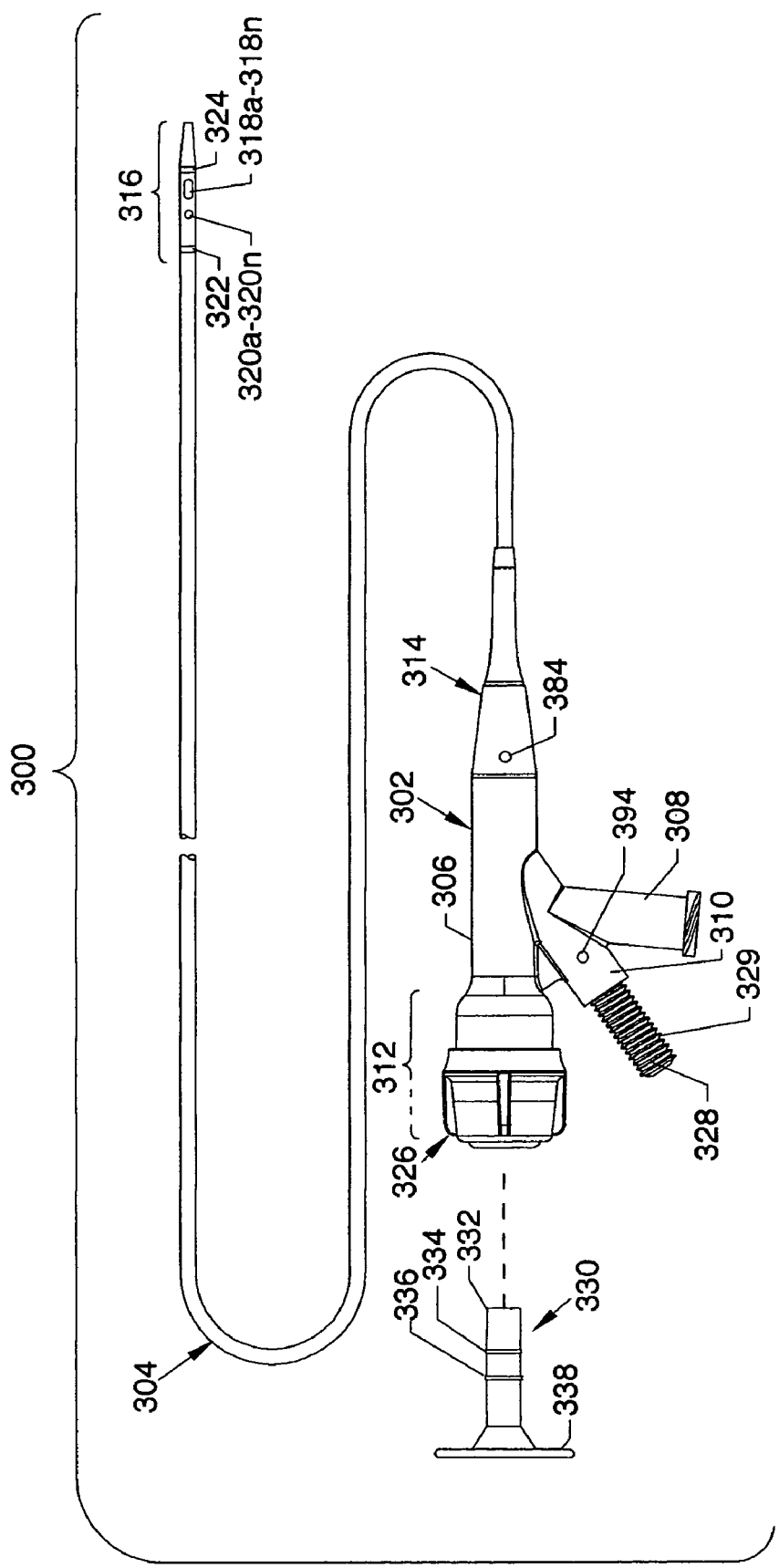
FIG. 39, a fifth alternative embodiment, is a plan view of the visible components of a thrombectomy catheter device having a self-sealing hemostasis valve.

FIG. 39, a fifth alternate embodiment, is a plan view of th visible components of a thrombectomy catheter device having a self-sealing hemostasis valve 300, including a one-piece manifold 302 having multiple structures extending therefrom or attached thereto and including a catheter tube 304 and other components as described herein. The visible portion of the one-piece manifold 302 includes a central tubular body 306, an exhaust branch 308 and a flangeless high pressure connection branch 310 extending angularly from the central tubular body 306, and a partially shown cavity body 312 extending proximally from the central tubular body 306. The proximal end of the catheter tube 304 secures to the manifold 302 by an interceding streamlined flexible strain relief 314. The proximal end of the catheter tube 304 extends through streamlined flexible strain relief 314 to communicate with the manifold 302. The catheter tube 304 extends distally to a tip 316 which is tapered and which can be flexible in design. The tip 316 of the catheter tube 304 includes a plurality of inflow orifices 318a-318n and a plurality of outflow orifices 320a-320n, and radiopaque marker bands 322 and 324, all of which are disclosed and described in detail in previous patent applications and patents by the applicants. Also shown is a hemostasis nut 326 aligned to and snappingly engaged with the proximal region of the cavity body 312, and a threaded high pressure connection port 328 having threads 329 which is secured such as by, but not limited to, adhesive, to the high pressure connection branch 310. Also provided as part of the fifth alternate embodiment is an introducer 330 having a hollow shaft 332, annular rings 334 and 336 about the hollow shaft 332, and an actuating handle 338. The structure of introducer 330 is similar to the structure of introducer 136 which has been previously described with reference to FIG. 15 and the function of which also has been previously described.

Figure 40:
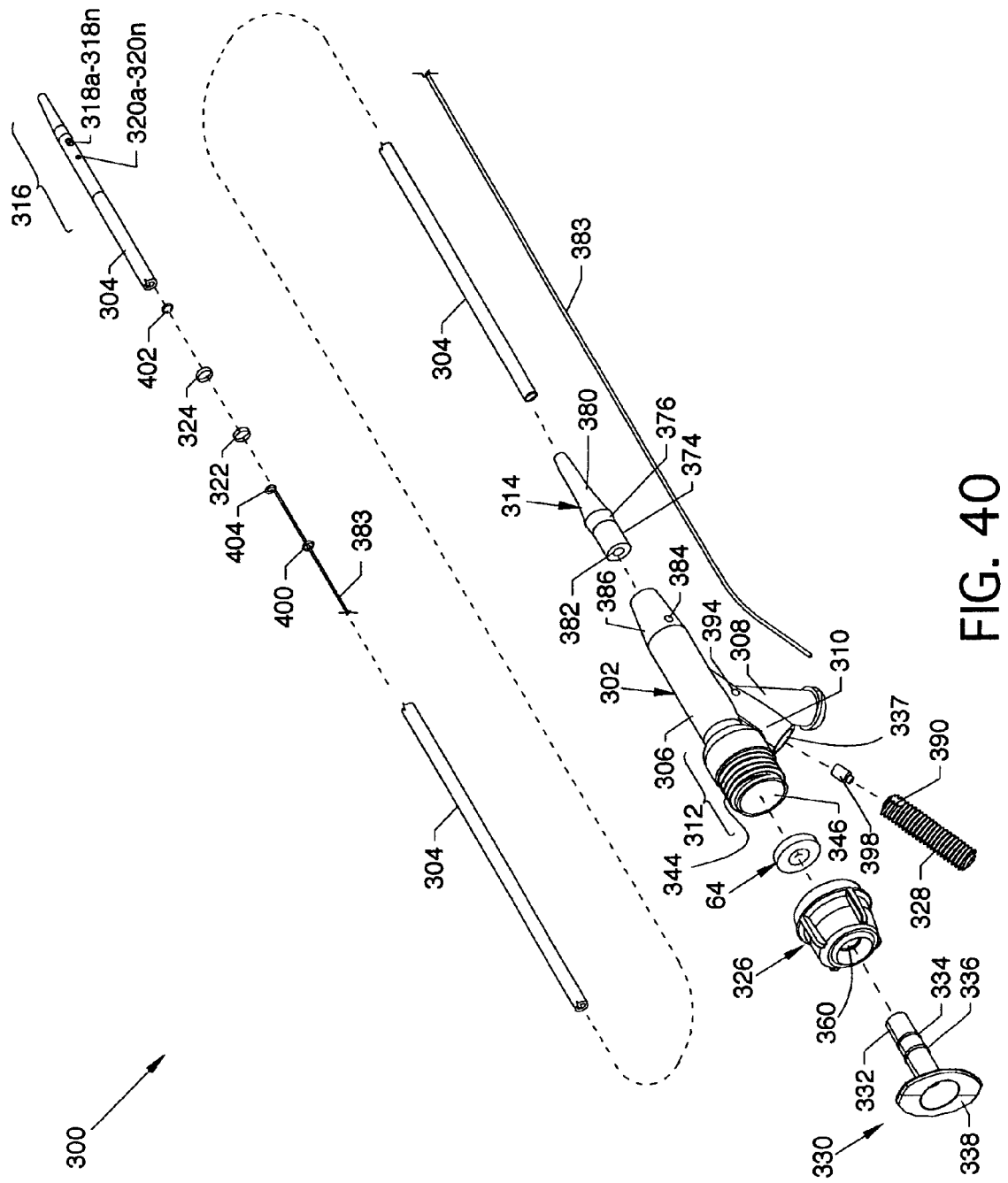
FIG. 40 is an isometric exploded view of the fifth alternate embodiment thrombectomy catheter device having a self-sealing hemostasis valve.
Figure 41:
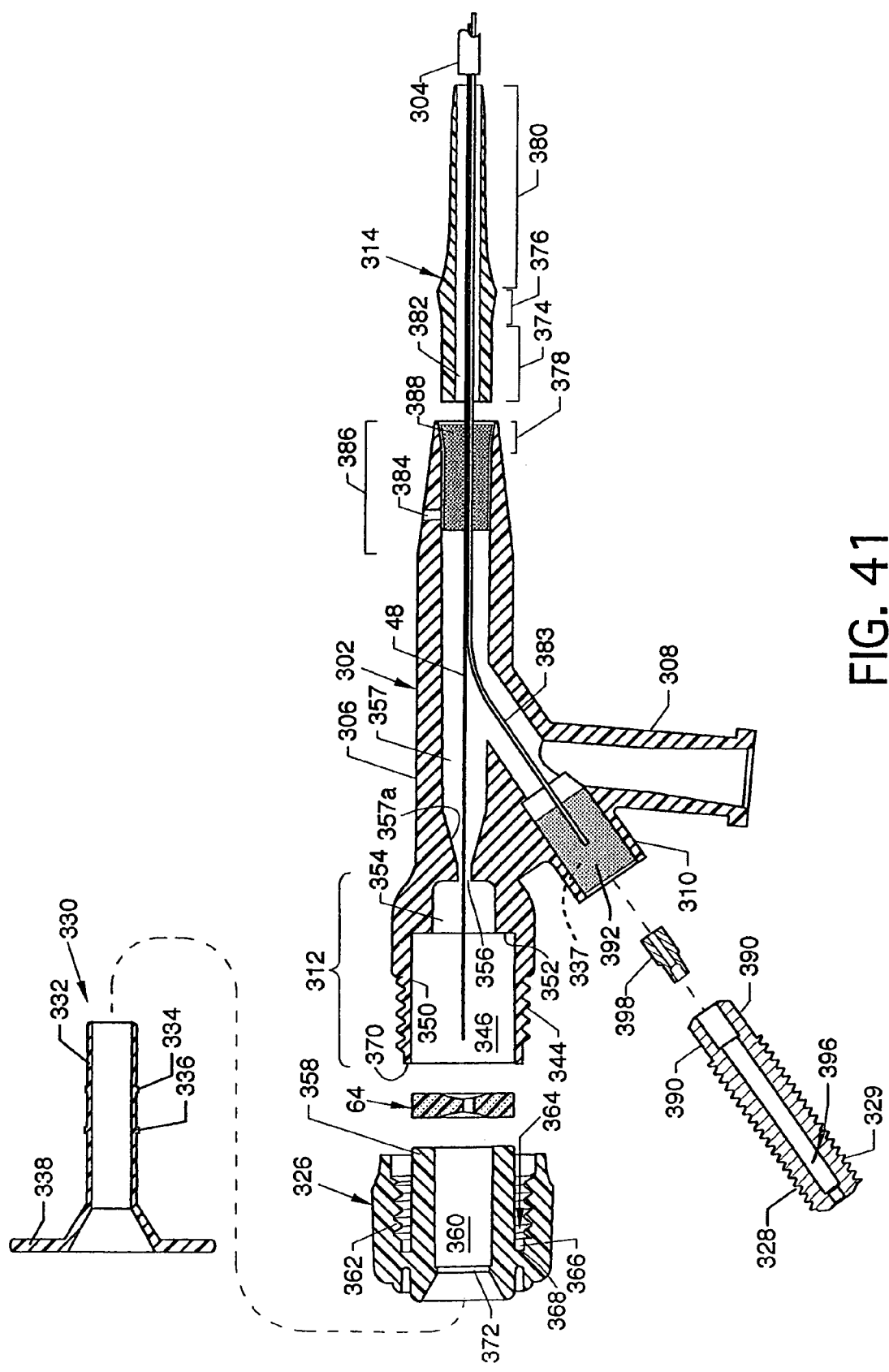
FIG. 41 is an exploded view in partial cross section of the components of the fifth alternate embodiment thrombectomy catheter device having a self-sealing hemostasis valve.

FIG. 40 is an isometric exploded view of the thrombectomy catheter device having a self-sealing hemostasis valve 300, and FIG. 41 is an exploded view in partial cross section of the components of the fifth alternate embodiment thrombectomy catheter device having a self-sealing hemostasis valve 300. The fifth alternate embodiment provides a thrombectomy catheter device having a self-sealing hemostasis valve 300 having fewer components and simplified structure where the use of complex threaded surfaces and structures is minimized. Such simplification is provided by the inclusion of the streamlined flexible strain relief 314 which is fitted and adhesively or otherwise suitably affixed to the distal interior portion of the manifold 302, and by the inclusion of a threaded high pressure connection port 328 which is fitted and adhesively or otherwise suitably affixed to the interior of the high pressure connection branch passageway 337 of the high pressure connection branch 310.

The fifth alternate embodiment provides a thrombectomy catheter device having a self-sealing hemostasis valve 300 which features the hemostasis nut 326 which aligns over and about threads 344 at the proximal region of the manifold 302. The thrombectomy catheter device having a self-sealing hemostasis valve 300 utilizes a number of the components, structures, and features of the previously described thrombectomy catheter devices having a self-sealing hemostasis valve 10, 10a, 10b, 10c and 10d and also operates in similar fashions according to the teachings of the invention, but includes a different arrangement and/or type of components that align within and/or which can be associated with and which can be accommodated internally by an alternately configured cavity 346 located in the cavity body 312 of the manifold 302. The cavity 346 is for the most part tubular in shape including a tubular cavity wall 350 and a planar surface 352 which is annular and circular and which intersects the tubular cavity wall 350. A cavity extension 354, being for the most part tubular, extends distally from the cavity 346 beginning at the planar surface 352 to intersect and connect with an orifice 356. The orifice 356 is common to the cavity extension 354, the cavity 346, and a tapered central passageway 357 located central to the central tubular body 306. The cavity 346 accommodates the self-sealing hemostasis valve 64, previously described in detail with reference to FIGS. 4, 5 and 6, which aligns to planar surface 352.

Figure 42:
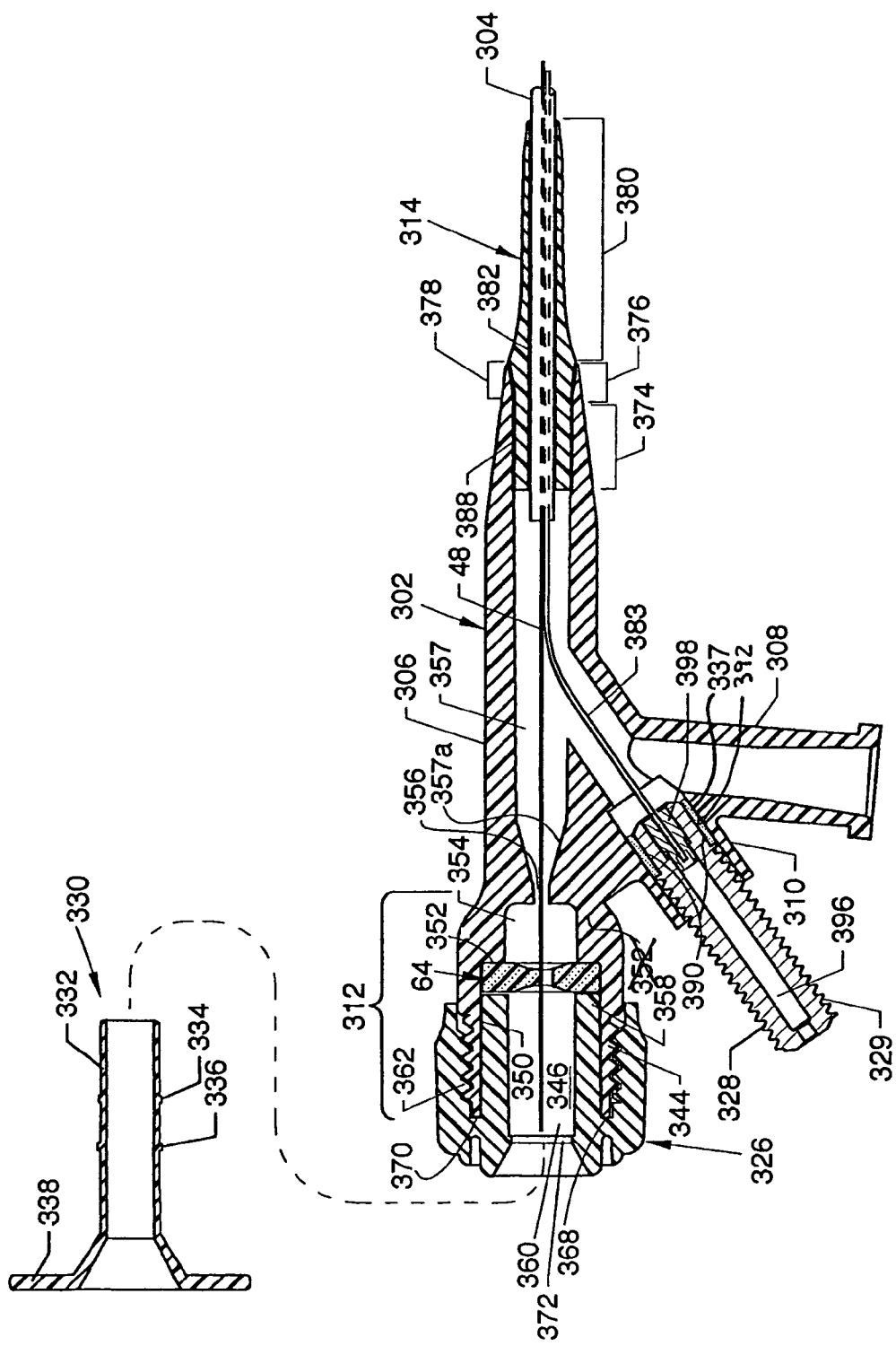
FIG. 42 is a view in partial cross section of the assembled components of the fifth alternate embodiment shown over and about and with the use of a guidewire and showing the introducer detached.

Also provided as part of the fifth alternate embodiment is the introducer 330, previously described as introducer 136 and having like components and functions, having a hollow shaft 332, annular rings 334 and 336 about the hollow shaft 332, and an actuating handle 338. The hollow shaft 332 accommodatingly aligns in the hemostasis nut 326. The hemostasis nut 326 includes a centrally located cylindrical boss 358, a beveled passageway 360 extending through and in part forming the cylindrical boss 358, and internal threads 362 distanced from the cylindrical boss 358 by a distally located space 364 extending along the internal threads 362 and along the distal portion of the cylindrical boss 358. A proximally located space 366 is located adjacent to the distally located space 364. An annular stop surface 368 is located at the proximal region of the proximally located space 366. The distally located space 364 accommodates the proximal end 370 of the manifold 302 including threads 344 located along and about the outer proximal portion of the cavity body 312 of the manifold 302. Also included in the hemostasis nut 326 is an annular lip 372 which can be utilized for snap engagement of the introducer 330 or other particular styles or types of introducers as required. The hemostasis nut 326 threadingly engages the manifold 302 where the internal threads 362 of the hemostasis nut 326 engage and are advanced along the threads 344 of the manifold 302 until advancement of the hemostasis nut 326 is predeterminately stopped by impingement of the annular stop surface 368 against the proximal end 370 of the manifold 302, whereby and whereupon the cylindrical boss 358 is brought to bear directly against the self-sealing hemostasis valve 64 resultingly bringing pressure to bear as required against the self-sealing hemostasis valve 64 to effect sealing with the cavity wall 350 of the cavity 346, to seal the self-sealing hemostasis valve 64 to the guidewire 48 and to seal the self-sealing hemostasis valve 64 to the planar surface 352. In the alternative, a suitable adhesive can be applied to the internal threads 362 of the hemostasis nut 326 and/or to the threads 344 of the manifold 302 to ensure permanent fixation of the hemostasis nut 326 to the manifold 302. Such engagement also ensures fixed and nonadjustable sealing of the self-sealing hemostasis valve 64 to a guidewire, such as previously described. The self-sealing hemostasis valve 64 is captured in the cavity 346 by engagement of the hemostasis nut 326 to the cavity body 312 of the manifold 302, as shown in FIG. 42. Due to the similar geometrical configurations of the opposing faces and associated structure therebetween of the self-sealing hemostasis valve 64, the self-sealing hemostasis valve 64 can be inserted into the cavity 346 without regard to the orientation of the opposing sides.

The streamlined flexible strain relief 314 can be fashioned of flexible plastic, rubber or the like and includes a constant radius region 374 adjoined by a short tapered region 376, each region fitting to and being accommodated respectively by the tapered central passageway 357 and an included short tapered region 378 of the tapered central passageway 357 of the manifold 302, as shown in FIG. 42. Adjoining the short tapered region 376 of the streamlined flexible strain relief 314 is a tapered region 380 being located distally thereto. A passageway 382 extends along the length of the streamlined flexible strain relief 314 for accommodation and passage of the guidewire 48 and a high pressure tube 383. An adhesive injection port 384 can be located at a suitable location extending through a tapered exterior region 386 of the manifold 302, which is flangeless, to introduce adhesive 388 to the distal interior region of the manifold 302 including the distal end of the tapered central passageway 357 and the included short tapered region 378 of the tapered central passageway 357. Such adhesive injection can be accomplished when the streamlined flexible strain relief 314 is mated to the distal end of the manifold 302, as shown in FIG. 42, or, adhesive may be applied to the mated surfaces separately, or electronic welding or bonding can be incorporated, or adhesive may be otherwise suitably applied as applicable to the art.

The threaded high pressure connection port 328 has a passageway 396 and is fitted to and adhesively affixed to the interior of the flangeless high pressure connection branch 310 of the manifold 302 opposing flats 390 are located at the distal portion of the threaded high pressure connection port 328 to adequately receive adhesive 392 in close communication to ensure proper physical fixation and adhering of the threaded high pressure connection port 328 within the high pressure connection branch passageway 337 of the high pressure connection branch 310. An adhesive injection port 394 (FIGS. 39 and 40) can be located at a suitable location to extend through the high pressure connection branch 310 of the manifold 302 to introduce adhesive 392 to the interior region of the high pressure connection branch 310. The adhesive 392, in addition to adhering the flats 390 of the threaded high pressure connection port 328 to the high pressure connection branch passageway 337, also bonds the appropriate portions of the threads 329 of the threaded high pressure connection port 328 to the high pressure connection branch passageway 337. Adhesive injection can be accomplished when the threaded high pressure connection port 328 is mated to the high pressure connection branch 310 of the manifold 302, as shown in FIG. 42. Adhesive could also be applied to the mated surfaces separately, or electronic welding or bonding can be incorporated, or adhesive may be otherwise suitably applied as applicable to the art. Also shown is a ferrule 398 which aligns and suitably secures within the passageway 396 of the threaded high pressure connection port 328, the combination of which aligns partially within the high pressure connection branch passageway 337 of the high pressure connection branch 310.

One end of the high pressure tube 383, shown in segmented form, is utilized for delivery of high pressure ablation liquids and suitably secures in a center passage of the ferrule 398 to communicate with the passageway 396 of the threaded high pressure connection port 328. The high pressure tube 383 also extends through the high pressure connection branch passageway 337, through part of the tapered central passageway 357, through the streamlined flexible strain relief 314, through the catheter tube 304, and through exhaust tube support rings 400 and 402 to the tip 316 where termination is provided in the form of a fluid jet emanator 404. The high pressure tube 383 can also be attached to the exhaust tube support ring 400, such as by welding or other suitable means, and can function as support for the catheter tube 304 in the region beneath the radiopaque marker 322. Support of the catheter tube 304 in the region beneath the radiopaque marker 324 can be provided by the exhaust tube support ring 402.

Mode of Operation

Figure 43:
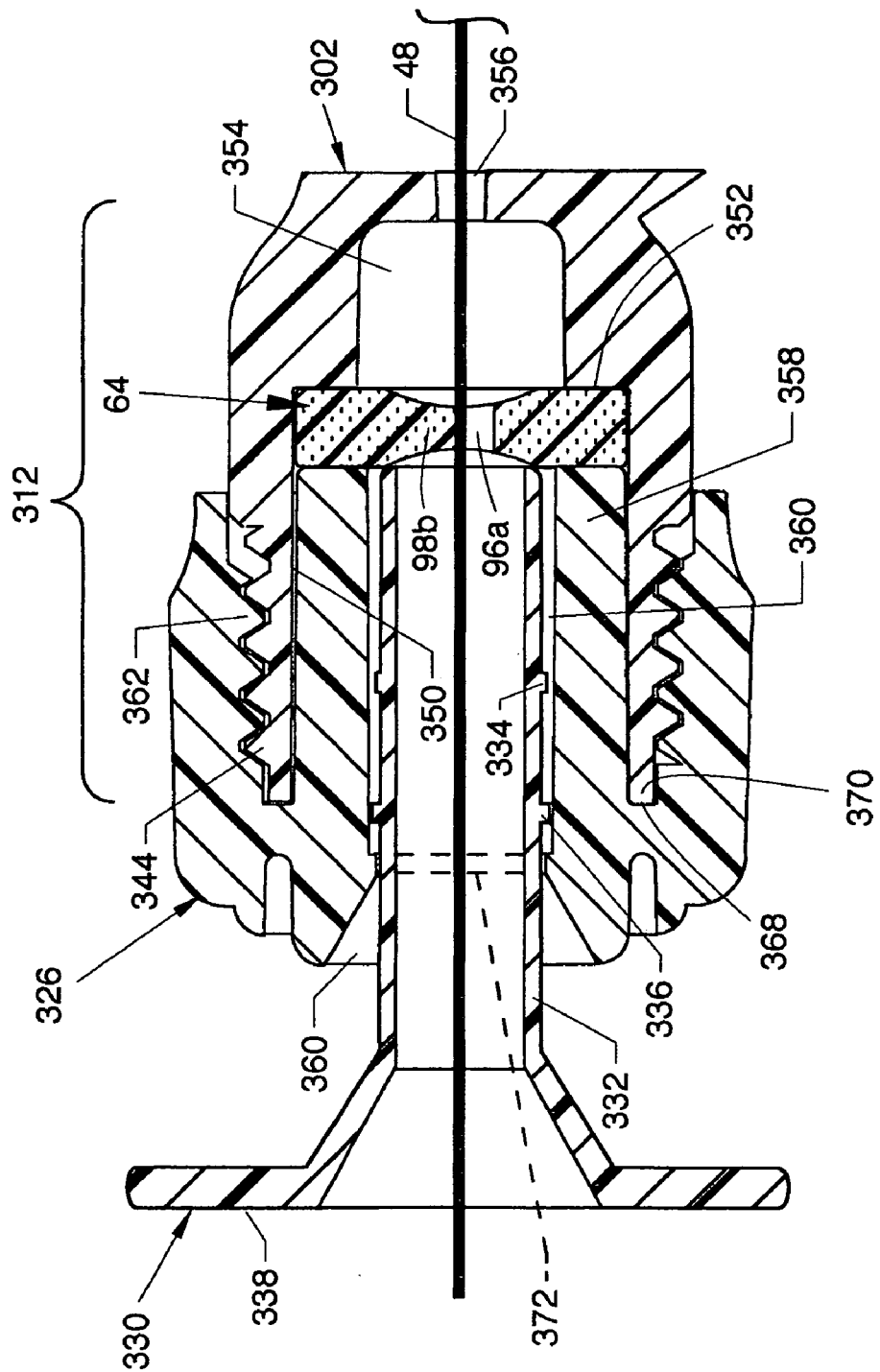
FIG. 43 is a fragmentary view in cross section of the proximal region of the manifold of the fifth alternative embodiment illustrating the introducer in normal engagement with the hemostasis nut and where the hemostasis nut is in fixed nonadjustable engagement with the proximal end of the manifold.

FIG. 42 is a view in partial cross section of the assembled components of FIG. 41 shown loaded and engaged over and about and with the use of a guidewire 48. The introducer 330 is shown disengaged from its normal engaged position in the beveled passageway 360 for clarity. Such loading and engagement occurs much in the same fashion as previously described with reference to FIGS. 10, 19 and 25 where the proximal end of the guidewire 48 enters the tip 316 of the catheter tube 304 and where the proximal guidewire tip is negotiated by the fluid jet emanator 404, the catheter tube 304, the tapered central passageway 357, and the orifice 356 which centers the guidewire 48 with the cavity extension 354 and with the components contained in the cavity 346. Such loading continues through the cavity extension 354, through the junction of the tips of the lobes 98a-98n which concurrently locate with the inboard portion of the slits 96a-96n of the self-sealing hemostasis valve 64 which, as previously described, can be oriented in either direction. Loading continues with the guidewire 48 exiting through the beveled passageway 360 of the hemostasis nut 326 and concentrically and co-located hollow shaft 332 of the introducer 330, as best shown in FIG. 43. Passage of the guidewire 48 through the junction of the tips of the lobes 98a-98n which concurrently locate with the inboard portion of the slits 96a-96n of the self-sealing hemostasis valve 64 causes the tips and areas immediately surrounding the tips of the lobes 98a-98n to sealingly and slidingly deform, distend, flex, conform or otherwise comply to and accommodate the profile of the guidewire 48. The guidewire 48 is shown in sealing and slidable engagement with the self-sealing hemostasis valve 64 where the pressure in the tapered central passageway 357 can be maintained at a setting which allows minimal leakage of fluids, such as blood or saline solution, proximally through the seal created between the self-sealing hemostasis valve 64 and the guidewire 48. Such pressure setting is determined by the fixed position of the cylindrical boss 358 of the hemostasis nut 326 in relation to the self-sealing hemostasis valve 64, as described later in detail. The hemostasis nut 326 serves to keep the self-sealing hemostasis valve 64 positioned without movement within the cavity 346 and to compress the self-sealing hemostasis valve 64 residing in the cavity 346 at a suitable level.

FIG. 43 is a fragmentary view in cross section of the proximal region of the manifold 302 illustrating the introducer 330 in normal engagement with the hemostasis nut 326 and where the hemostasis nut 326 is in fixed nonadjustable engagement with the proximal end 370 located at the proximal region of the manifold 302. The self-sealing hemostasis valve 64 provides for sealing which is nonadjustable about the guidewire 48 in a manner as previously described dependent on the degree of compression applied to the self-sealing hemostasis valve 64 by the fixed position of the hemostasis nut 326. Compression of the self-sealing hemostasis valve 64 is influenced by the pressure applied thereto by the cylindrical boss 358 extending from the interior of the hemostasis nut 326. Such pressure is determined by the relationship of the longitudinal position of the hemostasis nut 326 with respect to the proximal end 370 of the manifold 302 where the proximal end 370 impinges the annular stop surface 368 to influence such a relationship. If during fabrication the proximal end 370 is of a lengthened dimension proximally, the hemostasis nut 326 would correspondingly be located in a position more proximal, thereby applying less compressive force applied by the cylindrical boss 358 upon the self-sealing hemostasis valve 64, thereby decreasing the sealing capabilities against the guidewire 48 and against the cavity wall 350 of the cavity 346. Conversely, if during fabrication the proximal end 370 is of a shortened dimension distally, the hemostasis nut 326 would correspondingly be located in a position more distal, thereby applying more compressive force by the cylindrical boss 358 upon the self-sealing hemostasis valve 64, thereby increasing the sealing capabilities against the guidewire 48 and against the cavity wall 350 of the cavity 346. The annular ring 336 around and about the hollow shaft 332 of the introducer 330 snappingly engages the annular lip 372 of the beveled passageway 360 to capture the hollow shaft 332 of the introducer 330 within the beveled passageway 360, whereby the introducer 330 is positioned as shown for normal use where the distal end of the introducer 330 is in close proximity to the self-sealing hemostasis valve 64.

Figure 44:
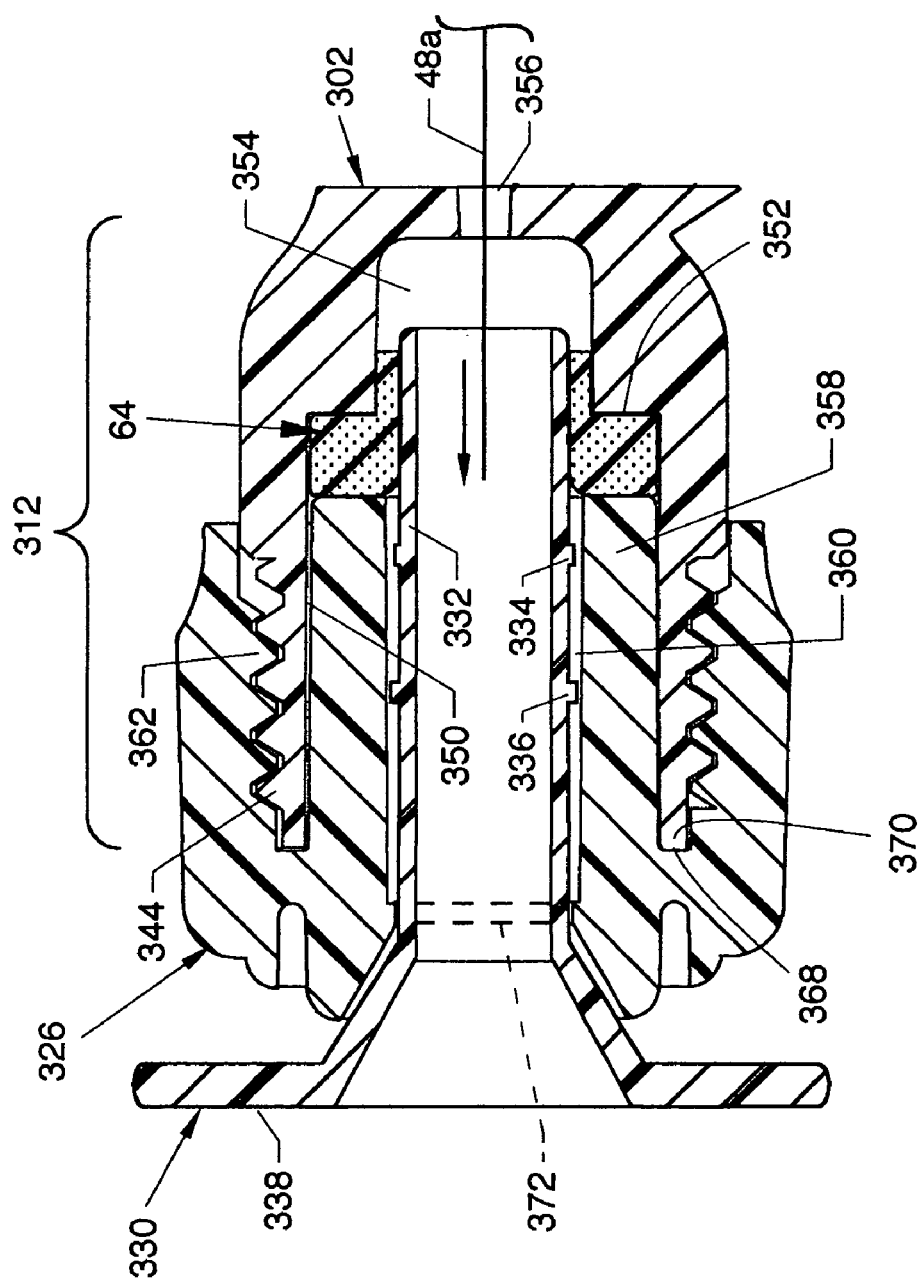
FIG. 44 is a view like FIG. 43 illustrating the function of the introducer to perform alternate functions as required either to bleed air out of the manifold or to aid guidewire movement through the self-sealing hemostasis valve.

FIG. 44 is a view like FIG. 43 illustrating the function of the introducer 330 to perform alternate functions as required either to bleed air or fluids out of the manifold 302 or to aid guidewire movement through the self-sealing hemostasis valve 64. To achieve such usefulness, the actuating handle 338 of the introducer 330 is manually pushed in a distal direction to force the distal end of the hollow shaft 332 towards and through the slits 96a-96n of the self-sealing hemostasis valve 64. Such entry into and through the self-sealing hemostasis valve 64 flexes, deforms and distends the lobes 98a-98n apart and in a distal direction to render the sealing capability against a guidewire, such as guidewire 48, ineffective. The distal portion of the introducer 330 is accommodated by the cavity extension 354 during actuation of the introducer 330 in a distal direction. The ability to spread or open the tips of the lobes 98a-98n is useful for use with an alternate guidewire, such as guidewire 48a, of a thinner or more flexible nature where the reduced thickness or increased flexibility thereof decreases or hinders the ability of the alternate guidewire 48a to successfully navigate, negotiate or pass through the lobes 98a-98n in their normal sealed position. In such state, any air of a pressure higher than ambient in the tapered central passageway 357 and connecting passages or tubes or other pertinent pressure carrying structures is vented to ambient through the hollow shaft 332 of the introducer 330. As readily seen in the illustration, the introducer 330 provides a relatively large passageway through the hollow shaft 332 for introduction of the proximal end of an alternate guidewire 48a, or the guidewire 48, for passage therethrough. The proximal end of the alternate guidewire 48a is aligned to the hollow shaft 332 by a taper 357a (FIGS. 41 and 42) at the proximal end of the tapered central passageway 357 adjacent to the orifice 356. The introducer 330, having been manually positioned as shown, remains held in that position by the engagement to the flexed, deformed and distended lobes 98a-98n of the self-sealing hemostasis valve 64. Subsequent to passage of the proximal end of the guidewire 48a to a position proximal to the flexed, distended and deformed self-sealing hemostasis valve 64, the introducer 330 can be manually retarded proximally to the position shown in FIG. 43 to disengage from intimate contact with the self-sealing hemostasis valve 64, whereupon a seal is established with the guidewire 48a (or guidewire 48) and the self-sealing hemostasis valve 64 regains sealing qualities relating to the guidewire 48a (or guidewire 48) and cavity 346, such as previously described.

Figure 45:
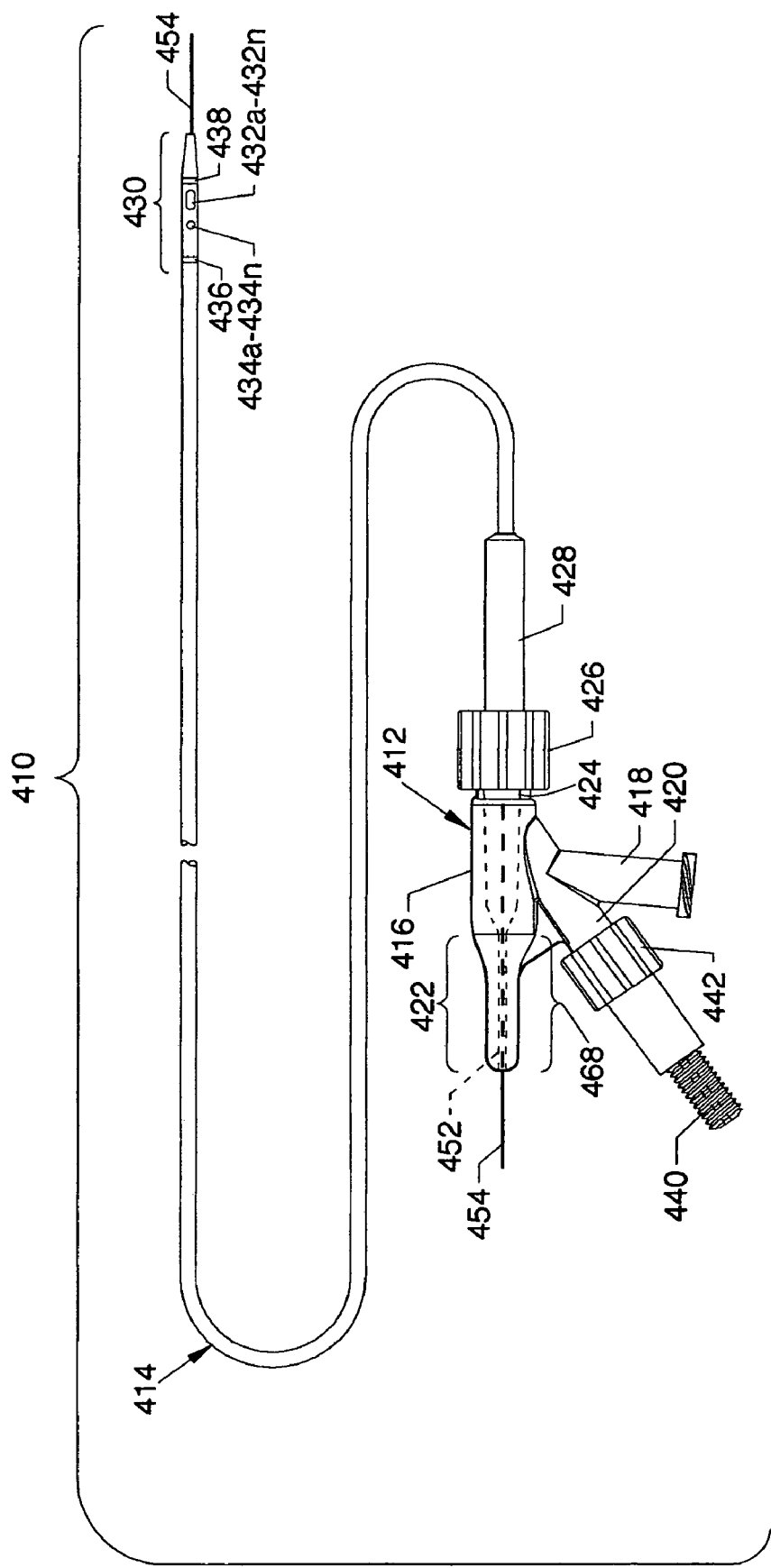
FIG. 45, a sixth alternative embodiment, is a plan view of the visible components of a thrombectomy catheter device having a self-sealing hemostasis valve.
Figure 46:
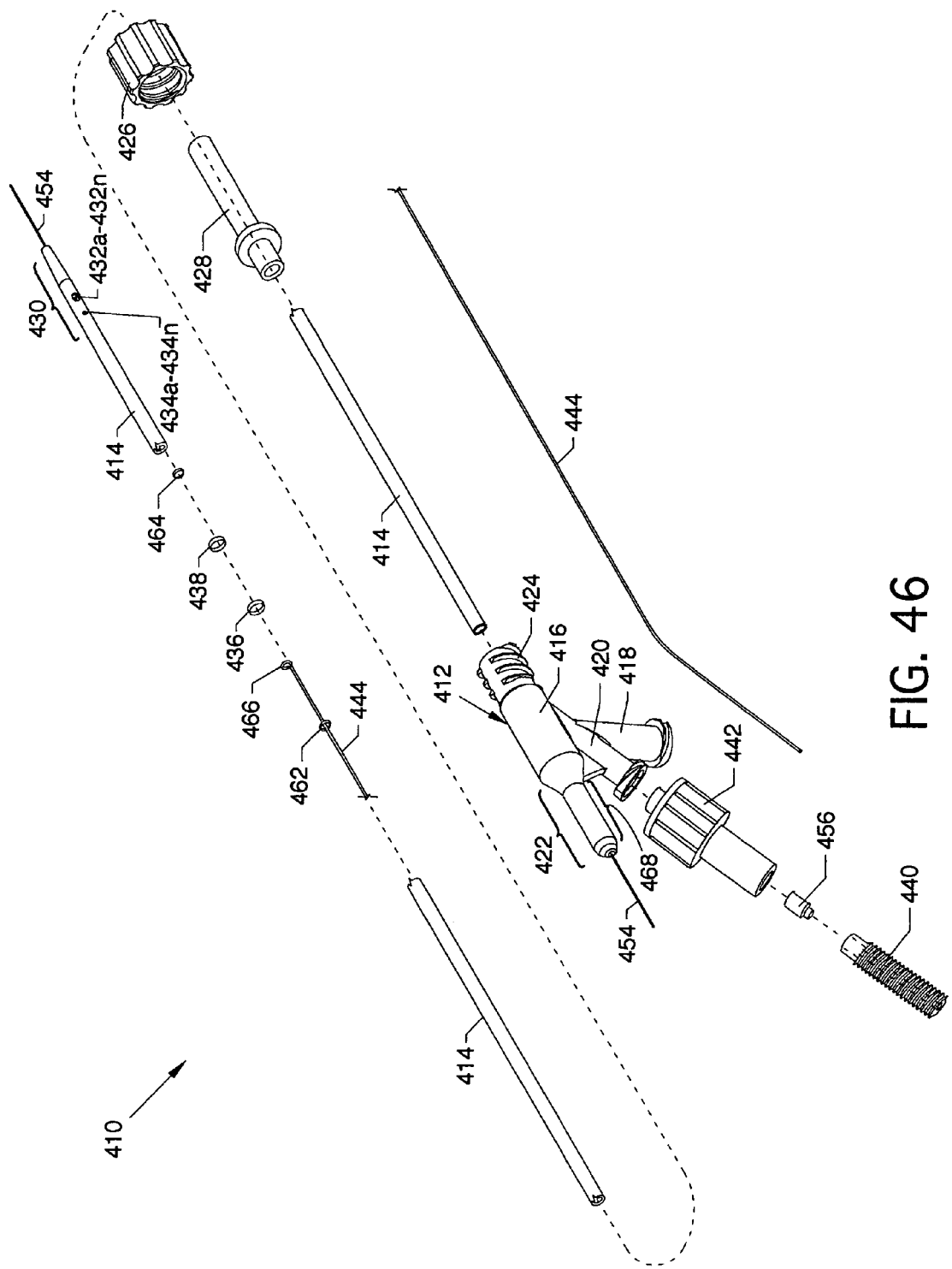
FIG. 46 is an exploded isometric view of the sixth alternate embodiment thrombectomy catheter device having a self-sealing hemostasis valve.

FIG. 45, a sixth alternate embodiment, is a plan view of the visible components of a thrombectomy catheter device having a self-sealing hemostasis valve 410, and FIG. 46 is an isometric exploded view of the thrombectomy catheter device having a self-sealing hemostasis valve 410 including a one-piece manifold 412 having multiple structures extending therefrom or attached thereto and including a catheter tube 414 and other components as described herein. The thrombectomy catheter device having a self-sealing hemostasis valve 410 utilizes a number of the components, structures, and features of the previously described thrombectomy catheter devices having a self-sealing hemostasis valve 10, 10a, 10b, 10c, 10d and 300, and also operates in a somewhat similar fashion according to the teachings of the invention, but includes a different arrangement and/or type of components that align within and/or which can be associated with and which are located adjacent to a central tubular body 416 of the manifold 412. The one-piece manifold 412 includes the central tubular body 416, an exhaust branch 418 and a high pressure connection branch 420 extending angularly from the central tubular body 416, an elongated hemostasis valve body 422 extending proximally from the central tubular body 416, and extending distally from the central tubular body 416, a threaded connection port 424. The proximal end of the catheter tube 414 secures to the manifold 412 by the use of a Luer fitting 426 accommodated by the threaded connection port 424. The proximal end of the catheter tube 414 extends through a strain relief 428 and through the Luer fitting 426 to communicate with the manifold 412. The catheter tube 414 extends distally to a tip 430 which is tapered and which can be flexible in design. The tip 430 of the catheter tube 414 includes a plurality of inflow orifices 432a-432n and a plurality of outflow orifices 434a-434n, and radiopaque marker bands 436 and 438, all of which are disclosed and described in detail in previous patent applications and patents by the applicants. Also shown is a threaded high pressure connection port 440 secured to the high pressure connection branch 420 by a Luer connector 442.

Figure 47:
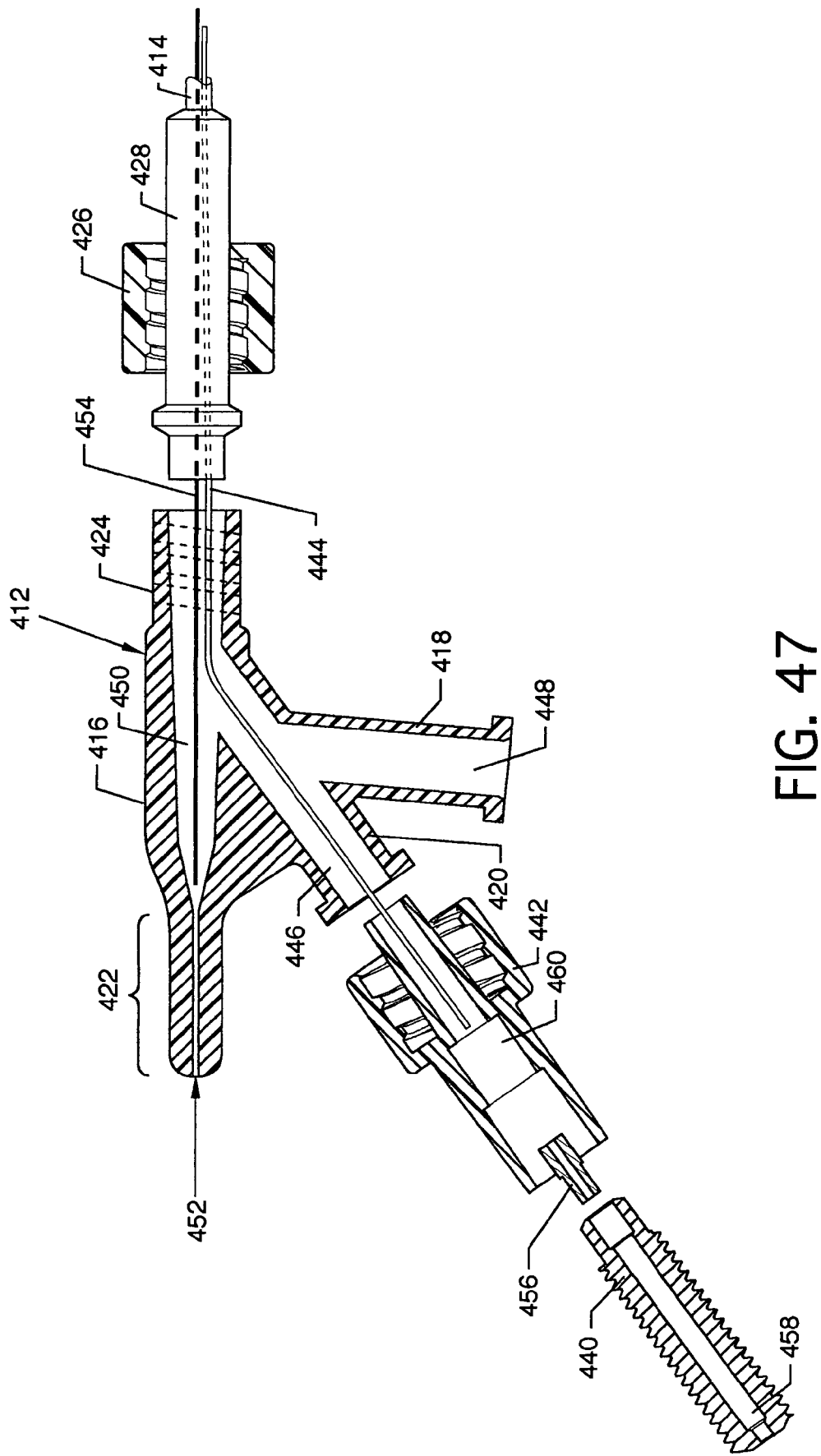
FIG. 47 is an exploded view in partial cross section of the components of the sixth alternate embodiment thrombectomy catheter device having a self-sealing hemostasis valve; and, FIG. 48 is a view in partial cross section of the assembled components of the sixth alternate embodiment shown over and about and with the use of a guidewire.
Figure 48:
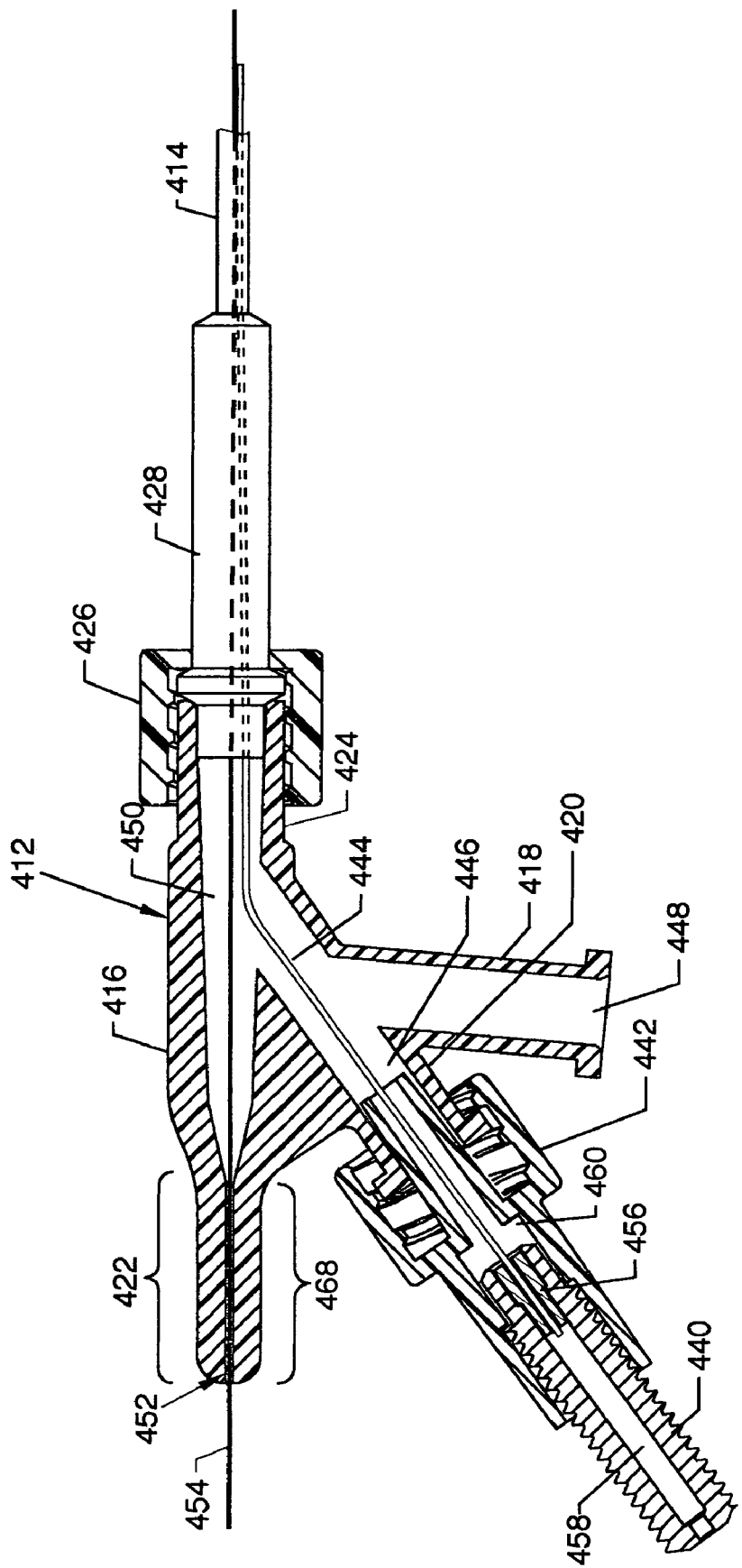

FIG. 47 is an exploded view in cross section of the components of the thrombectomy catheter device having a self-sealing hemostasis valve 410, and FIG. 48 is a view in partial cross section of the assembled components of the thrombectomy catheter device having a self-sealing hemostasis valve 410 each excluding the full length of the catheter tube 414 and the included tip 430, but including the guidewire 454 such as is incorporated in the use of the invention. The catheter tube 414, which also serves and functions as an exhaust tube, and a high pressure tube 444 distal to the strain relief 428 are foreshortened and shown as partial lengths for the purpose of clarity.

With reference to FIG. 47 and FIG. 48, the sixth alternate embodiment is further described. The manifold 412 includes connected and communicating passageways (FIG. 47) including a high pressure connection branch passageway 446, an exhaust branch passageway 448, a tapered central passageway 450 extending from and through the threaded connection port 424 and through the central tubular body 416 to and communicating with an elongated hemostasis valve passageway 452 of defined dimensions, which preferably is cylindrical, co-located with the elongated hemostasis valve body 422, and being located proximal to the central tubular body 416.

Also shown is a ferrule 456 which aligns within a passageway 458 of the threaded high pressure connection port 440, the combination of which aligns partially within the interior passageway 460 of the Luer connector 442. One end of the high pressure tube 444 is utilized for delivery of high pressure ablation liquids and suitably secures in a center passage of the ferrule 456 to communicate with the passageway 458 of the threaded high pressure connection port 440. The high pressure tube 444 also extends through the high pressure connection branch passageway 446, through part of the tapered central passageway 450, through the strain relief 428 and Luer fitting 426, through the catheter tube 414, and through exhaust tube support rings 462 and 464 to the tip 430 where termination is provided in the form of a fluid jet emanator 466. The high pressure tube 444 can also be attached to the exhaust tube support ring 462, such as by welding or other suitable means, and can function as support for the catheter tube 414 in the region beneath the radiopaque marker 436. Support of the catheter tube 414 in the region beneath the radiopaque marker 438 can be provided by the exhaust tube support ring 464.

Mode of Operation

Stationary components and static components are incorporated to form a self-sealing hemostasis valve 468 where the relationship of the elongated hemostasis valve passageway 452 to the portion of a guidewire 454 which actively or passively transits the elongated hemostasis valve passageway 452 located central to the elongated hemostasis valve body 422 forms the self-sealing hemostasis valve 468. For purposes of demonstration and illustration, the length of the elongated hemostasis valve passageway 452 could range from 0.25 inch to 0.50 inch and could have a diameter of 0.015 inch. The guidewire 454 could have a diameter of 0.014 inch thereby having a total clearance of 0.001 inch between the guidewire 454 and the elongated hemostasis valve passageway 452. The interference of the guidewire 454 along and within the interior of the elongated hemostasis valve passageway 452 achieves hemostasis with an acceptable amount of leakage through the self-sealing hemostasis valve 468. Various sizes of guidewires 454 could be used where a matched thrombectomy catheter device having a self-sealing hemostasis valve 410 has an appropriately dimensioned elongated hemostasis valve passageway 452. As in other self-sealing hemostasis valves, the self-sealing hemostasis valve 468 provides for hemostasis when the components are static or when the components are positioned along a guidewire.

Any self-sealing hemostasis seal valve, passageway or other style of seal, such as previously described herein, can exhibit frictional resistance when passed over a guidewire. Such frictional resistance can be reduced by hydrophilically coating the self-sealing hemostasis seal valve, seal or interior of a passageway through which a guidewire passes. The interior of the passageway through which a guidewire passes could also be coated with a hydrogel which expands when hydrated to offer a better seal and where the passageway is kept closed even when a guidewire is not present. The use of hydrogel allows for smooth passage over a guidewire due to its slippery nature.

Various modifications can made to the present invention without departing from the apparent scope thereof.

THROMBECTOMY CATHETER DEVICE HAVING A SELF-SEALING HEMOSTASIS VALVE PARTS LIST

| | |
|---|---|
| 10 | thrombectomy catheter device having a self-sealing hemostasis valve |
| 10a–d | alternative embodiment of thrombectomy catheter device having a self-sealing hemostasis valve |
| 12 | manifold |
| 12a–d | manifold |
| 13 | catheter tube |
| 14 | central tubular body |
| 16 | exhaust branch |
| 18 | high pressure connection branch |
| 20 | cavity body |
| 22 | threaded connection port |
| 26 | Luer fitting |
| 28 | strain relief |
| 30 | tip |
| 32a–n | inflow orifices |
| 34a–n | outflow orifices |
| 36 | radiopaque marker band |
| 38 | radiopaque marker band |
| 40 | hemostasis nut |
| 41 | high pressure tube |
| 42 | threaded high pressure connection port |
| 44 | Luer connector |
| 46 | introducer |
| 48 | guidewire |
| 48a | guidewire |
| 50 | high pressure connection branch passageway |
| 52 | exhaust branch passageway |
| 54 | tapered central passageway |
| 54a | taper |
| 56 | cavity |
| 57 | tubular cavity wall |
| 58 | annular ring |
| 59 | planar surface |
| 60 | angled annular surface |
| 61 | orifice |
| 62 | threads |
| 64 | self-sealing hemostasis valve |
| 66 | elongated washer |
| 68 | cylindrical boss |
| 70 | beveled passageway |
| 71 | proximally located space |
| 72 | internal threads |
| 73 | annular ring |
| 74 | ferrule |
| 75 | passageway |
| 76 | interior passageway |

THROMBECTOMY CATHETER DEVICE HAVING A SELF-SEALING HEMOSTASIS VALVE PARTS LIST

| | |
|---|---|
| 77 | distally located space |
| 78 | exhaust tube support ring |
| 79 | proximal end |
| 80 | exhaust tube support ring |
| 82 | fluid jet emanator |
| 84 | hollow shaft |
| 86 | actuating handle |
| 88 | face |
| 90 | face |
| 92 | recessed surface |
| 94 | recessed surface |
| 95 | edge |
| 96a–n | slits |
| 98a–n | lobes |
| 100 | face |
| 102 | face |
| 104 | recessed passage |
| 106 | recessed passage |
| 108 | central passage |
| 110 | edge |
| 112 | annular lip |
| 120 | cavity |
| 122 | cavity body |
| 124 | cavity wall |
| 126 | truncated conical surface |
| 128 | orifice |
| 130 | dual seal |
| 132 | wide washer |
| 133 | central passage |
| 134 | washer |
| 135 | central passage |
| 136 | introducer |
| 138 | hollow shaft |
| 140 | annular ring |
| 142 | annular ring |
| 144 | actuating handle |
| 146 | truncated conical surface |
| 148 | face |
| 150 | edge |
| 152 | rounded recess |
| 154 | multi-radiused passageway |
| 156 | cavity |
| 158 | cavity body |
| 160 | cavity wall |
| 162 | planar surface |
| 164 | cavity extension |
| 166 | orifice |
| 168 | hemostasis nut |
| 170 | cylindrical boss |
| 172 | beveled passageway |
| 174 | internal threads |
| 176 | proximally located space |
| 178 | distally located space |
| 180 | annular stop surface |
| 182 | threads |
| 184 | annular lip |
| 186 | proximal end |
| 187 | cavity insert |
| 188 | hemostasis nut |
| 190 | cavity |
| 192 | cavity body |
| 194 | cavity wall |
| 196 | planar surface |
| 198 | orifice |
| 200 | recess |
| 202 | passage |
| 204 | cylindrical boss |
| 206 | beveled passageway |
| 208 | internal threads |
| 210 | distally located space |
| 212 | proximally located space |
| 214 | annular stop surface |
| 216 | proximal end |
| 218 | threads |
| 220 | annular lip |
| 222 | face |
| 224 | face |
| 226 | edge |
| 228 | smooth cylindrical surface |
| 230 | hemostasis nut |
| 232 | smooth cylindrical surface |
| 234 | cavity |
| 236 | cavity body |
| 238 | cavity wall |
| 240 | planar surface |
| 242 | cavity extension |
| 244 | orifice |
| 248 | cylindrical boss |
| 250 | beveled passageway |
| 252 | proximally located space |
| 253 | distally located space |
| 254 | annular stop surface |
| 255 | annular lip |
| 256 | proximal end |
| 258 | annular shoulder |
| 300 | thrombectomy catheter device having a self-sealing hemostasis valve |
| 302 | manifold |
| 304 | catheter tube |
| 306 | central tubular body |
| 308 | exhaust branch |
| 310 | high pressure connection branch |
| 312 | cavity body |
| 314 | streamlined flexible strain relief |
| 316 | tip |
| 318a–n | inflow orifices |
| 320a–n | outflow orifices |
| 322 | radiopaque marker band |
| 324 | radiopague marker band |
| 326 | hemostasis nut |
| 328 | threaded high pressure connection port |
| 329 | threads |
| 330 | introducer |
| 332 | hollow shaft |
| 334 | annular ring |
| 336 | annular ring |
| 337 | high pressure connection branch passageway |
| 338 | actuating handle |
| 344 | threads |
| 346 | cavity |
| 350 | cavity wall |
| 352 | planar surface |

THROMBECTOMY CATHETER DEVICE HAVING A SELF-SEALING HEMOSTASIS VALVE
PARTS LIST (continued)

| | |
|---|---|
| 354 | cavity extension |
| 356 | orifice |
| 357 | tapered central passageway |
| 357a | taper |
| 358 | cylindrical boss |
| 360 | beveled passageway |
| 362 | internal threads |
| 364 | distally located space |
| 366 | proximally located space |
| 368 | annular stop surface |
| 370 | proximal end |
| 372 | annular lip |
| 374 | constant radius region |
| 376 | short tapered region |
| 378 | short tapered region |
| 380 | tapered region |
| 382 | passageway |
| 383 | high pressure tube |
| 384 | adhesive injection port |
| 386 | tapered exterior region |
| 388 | adhesive |
| 390 | flat |
| 392 | adhesive |
| 394 | adhesive injection port |
| 396 | passageway |
| 398 | ferrule |
| 400 | exhaust tube support ring |
| 402 | exhaust tube support ring |
| 404 | fluid jet emanator |
| 410 | thrombectomy catheter device having a self-sealing hemostasis valve |
| 412 | manifold |
| 414 | catheter tube |
| 416 | central tubular body |
| 418 | exhaust branch |
| 420 | high pressure connection branch |
| 422 | elongated hemostasis valve body |
| 424 | threaded connection port |
| 426 | Luer fitting |
| 428 | strain relief |
| 430 | tip |
| 432a–n | inflow orifices |
| 434a–n | outflow orifices |
| 436 | radiopaque marker band |
| 438 | radiopaque marker band |
| 440 | threaded high pressure connection port |
| 442 | Luer connector |
| 444 | high pressure tube |
| 446 | high pressure connection branch passageway |
| 448 | exhaust branch passageway |
| 450 | tapered central passageway |
| 452 | elongated hemostasis valve passageway |
| 454 | guidewire |
| 456 | ferrule |
| 458 | passageway |
| 460 | interior passageway |
| 462 | exhaust tube support ring |
| 464 | exhaust tube support ring |
| 466 | fluid jet emanator |
| 468 | self-sealing hemostasis valve |

The invention claimed is:

1. A self-sealing hemostasis valve apparatus, comprising:
   a. a hemostasis valve having
      (1) a first face;
      (2) a second face;
      (3) a circumferential edge between the first face and the second face, the circumferential edge defining a center; and,
      (4) a plurality of slits, each slit parting the valve between the first face and the second face and extending outward from the center, with adjacent slits defining a lobe which is one of a plurality of lobes, and each slit further defining a boundary between adjacent lobes, wherein adjacent lobes are in mutual contact at the boundary defined by each slit;
   b. a hemostasis nut; and,
   c. an elongated washer having two ends and aligned with said center and located between said hemostasis valve and said hemostasis nut so that one of the two ends of the elongated washer contacts the first face or the second face of the hemostasis valve, said two ends having opposing recessed passages, with a central passage therebetween.

2. The self-sealing hemostasis valve apparatus of claim 1, wherein the first face includes a recessed surface.

3. The self-sealing hemostasis valve apparatus of claim 2, wherein the recessed surface is symmetrical.

4. The self-sealing hemostasis valve apparatus of claim 2, wherein the recessed surface is symmetrical about the center.

5. The self-sealing hemostasis valve apparatus of claim 4, wherein the recessed surface which is symmetrical about the center is a radiused surface.

6. The self-sealing hemostasis valve apparatus of claim 2, wherein the recessed surface includes the center and the extent of each slit is limited to the recessed surface.

7. The self-sealing hemostasis valve apparatus of claim 1, wherein each slit is linear and extends radially from the center.

8. The self-sealing hemostasis valve apparatus of claim 7, wherein the slits are radially symmetrically distributed such that the lobes are identical.

9. The self-sealing hemostasis valve apparatus of claim 1, wherein the first face includes a symmetrical recessed surface and the second face includes a symmetrical recessed surface, and wherein the symmetrical recessed surface of the first face is opposed to the symmetrical recessed surface of the second face such that the valve is thinner at the center than at the circumferential edge.

10. The self-sealing hemostasis valve apparatus of claim 9, wherein the symmetrical recessed surfaces are radiused.

11. The self-sealing hemostasis valve apparatus of claim 1, wherein the plurality of slits includes three slits.

12. The self-sealing hemostasis valve apparatus of claim 11, wherein the plurality of lobes includes three lobes, each of the three lobes being identical to the other two lobes of the plurality of lobes.

13. The self-sealing hemostasis valve apparatus of claim 12, wherein each of the three lobes is thinnest at the center.

14. The self-sealing hemostasis valve apparatus of claim 1, wherein each of the lobes has a first face and a second face, and the first face of each lobe has a radiused recess surface, each radiused recess surface of the first face of each lobe being symmetrical about the center of the valve such that each lobe is thinnest at the center.

15. The self-sealing hemostasis valve apparatus of claim 14, wherein the second face of each lobe has a radiused recess surface, each radiused recess surface of the second face of each lobe being symmetrical about the center of the valve.

16. The self-sealing hemostasis valve apparatus of claim 15, wherein the radiused recess surface of the first face of each lobe is opposed to the radiused recess surface of the second face of each lobe, and wherein the radii of both the first face and the second face of each lobe are identical.

17. The self-sealing hemostasis valve apparatus of claim 1, wherein the valve is formed of flexible, pliable and resilient material.

18. The self-sealing hemostasis valve apparatus of claim 17, wherein the material is medical grade silicone.

19. The self-sealing hemostasis valve apparatus of claim 1, wherein each of the lobes decreases in flexibility away from the center of the valve.

20. A thrombectomy catheter device, comprising:
  a. a manifold;
  b. a self-sealing hemostasis valve within the manifold, the valve including:
    (1) a first face;
    (2) a second face;
    (3) a circumferential edge between the first face and the second face, the circumferential edge defining a center; and,
    (4) a plurality of slits, each slit parting the valve between the first face and the second face and extending outward from the center, with adjacent slits defining a lobe which is one of a plurality of lobes, and each slit further defining a boundary between adjacent lobes, wherein adjacent lobes are in mutual contact at the boundary defined by each slit;
  c. an elongated washer having two ends and aligned with said center and located so that one of the two ends of the elongated washer contacts the first face or the second face of the hemostasis valve, said elongated washer having two recessed passages and a central passage; and,
  d. a fluid jet emanator.

21. The device of claim 20, wherein the manifold includes a cavity body and the valve is captured within the cavity body.

22. The device of claim 21, wherein the diameter of the cavity body is such that the valve is slightly oversize relative to the cavity body.

23. The device of claim 22, wherein the manifold further includes a hemostasis nut engaging the cavity body to capture the valve within the cavity body.

24. The device of claim 23, wherein the hemostasis nut may be manipulated to alter sealing characteristics of the valve.

25. The device of claim 24, further comprising:
  a. a first washer contacting a face of the valve; and,
  b. a second washer, the second washer contacting an opposite face of the valve, the first and second washers together defining a dual seal of the valve.

26. The device of claim 25, wherein the hemostasis nut includes a boss which impinges on the first washer such that the first and second washers cause the valve, interposed between the washers, to compress, deform, distend, flex, conform, comply to and accommodate a guidewire such that a higher pressure is maintained at one face of the valve relative to the other face of the valve whilst a guidewire passes therethrough.

27. The device of claim 23, wherein the hemostasis nut is nonadjustable.

28. The device of claim 23, wherein the elongated washer is interposed between the valve and the hemostasis nut and is captured within the cavity body along with the valve.

29. The device of claim 28, wherein the elongated washer is formed of a material selected from the group consisting of polycarbonate and aluminum.

30. The device of claim 28, wherein the valve provides slidable and sealing engagement with a guidewire passing therethrough.

31. The device of claim 30, further comprising, in combination, an introducer for facilitating introduction of a guidewire through the valve.

32. The device of claim 31, wherein the device is characterized by a preset pressure maintenance by the valve.

33. The device of claim 31, wherein the hemostasis nut includes a cylindrical boss which impinges on the elongated washer such that the washer causes the valve to compress, deform, distend, flex, conform, comply to and accommodate the guidewire such that a higher pressure is maintained at one face of the valve relative to the other face of the valve whilst the guidewire passes therethrough.

34. A hemostasis valve combination, comprising:
  a. a first face, the first face having a recessed surface;
  b. a second face; the second face having a recessed surface opposed to the recessed surface of the first face;
  c. a circumferential edge between the first face and the second face, the circumferential edge defining a center, and the center being thinner than the circumference;
  d. a plurality of slits, each of the slits parting the valve between the opposed recessed surfaces and extending outwardly from the center, with adjacent slits defining a lobe which is one of a plurality of lobes, each lobe having mutual contact with at least one adjacent lobe at the boundary defined by the slit which separates the lobe from the at least one adjacent lobe;
  e. means for preventing the plurality of lobes from flexing in a first direction but allowing the plurality of lobes to flex in a second direction, such that the hemostasis valve allows flow in the second direction but denies flow in the first direction, the means for preventing the plurality of lobes from flexing in a first direction but allowing the plurality of lobes to flex in a second direction comprising a washer and a recessed passage; and,
  f. wherein at least a portion of the means for preventing the plurality of lobes from flexing in a first direction but allowing the plurality of lobes to flex in a second direction is located adjacent to the face of the hemostasis valve which is oriented towards the first direction.

35. The hemostasis valve combination of claim 34, wherein the hemostasis valve allows passage of a guidewire while retaining the characteristic of allowing flow in the second direction and denying flow in the first direction.

36. The hemostasis valve combination of claim 34, wherein the first direction is distal in a thrombectomy catheter.

37. The hemostasis valve combination of claim 34, wherein the means for preventing the plurality of lobes from flexing in a first direction but allowing the plurality of lobes to flex in a second direction includes an elongated washer, where the elongated washer further comprises a recessed passage and a planar surface.

38. The hemostasis valve combination of claim 37, wherein the planar surface is a planar surface distally arranged in a manifold to contact the hemostasis valve, and the elongated washer is proximally arranged in the manifold to contact the hemostasis valve.

39. The hemostasis valve combination of claim 38, further comprising a passage leading distally from the center of the hemostasis valve and a passage leading proximally from the recessed passage of the elongated washer.

40. The hemostasis valve combination of claim 39, wherein the elongated washer is held by a hemostasis nut.

41. The hemostasis valve combination of claim 40, wherein the hemostasis nut may be manipulated to modify the sealing properties of the valve.

42. The hemostasis valve combination of claim 40, wherein the hemostasis nut is fixed to the surrounding manifold.

43. The hemostasis valve combination of claim 40, wherein the hemostasis nut is adjustable along threads provided on the manifold, so as to drive the elongated washer distally into or proximally away from the hemostasis valve.

44. A thrombectomy catheter device, comprising:
 a. a manifold;
 b. a self-sealing hemostasis valve within the manifold, the valve including:
  (1) a first face;
  (2) a second face;
  (3) a circumferential edge between the first face and the second face, the circumferential edge defining a center; and,
  (4) a plurality of slits, each slit parting the valve between the first face and the second face and extending outward from the center, with adjacent slits defining a lobe which is one of a plurality of lobes, and each slit further defining a boundary between adjacent lobes, wherein adjacent lobes are in mutual contact at the boundary defined by each slit;
 c. an elongated washer having two ends and at least one recessed passage and aligned with said center and located so that one of the two ends of the elongated washer contacts the first face or the second face of the hemostasis valve;
 d. a fluid jet emanator;
 e. wherein the manifold includes a cavity body and the hemostasis valve is captured within the cavity body, the diameter of the cavity body being such that the hemostasis valve is slightly oversize relative to the cavity body;
 f. wherein the manifold further includes a hemostasis nut engaging the cavity body to capture the valve within the cavity body; and,
 g. wherein the elongated washer is interposed between the valve and the hemostasis nut and is captured within the cavity body along with the valve.

45. The device of claim 44, wherein the elongated washer is formed of a material selected from the group consisting of polycarbonate and aluminum.

46. The device of claim 44, wherein the valve provides slidable and sealing engagement with a guidewire passing therethrough.

47. A hemostasis valve combination, comprising:
 a. a first face, the first face having a recessed surface;
 b. a second face; the second face having a recessed surface opposed to the recessed surface of the first face;
 c. a circumferential edge between the first face and the second face, the circumferential edge defining a center, and the center being thinner than the circumference;
 d. a plurality of slits, each of the slits parting the valve between the opposed recessed surfaces and extending outwardly from the center, with adjacent slits defining a lobe which is one of a plurality of lobes, each lobe having mutual contact with at least one adjacent lobe at the boundary defined by the slit which separates the lobe from the at least one adjacent lobe;
 e. means for preventing the plurality of lobes from flexing in a first direction but allowing the plurality of lobes to flex in a second direction, such that the hemostasis valve allows flow in the second direction but denies flow in the first direction; and,
 f. wherein the means for preventing the plurality of lobes from flexing in a first direction but allowing the plurality of lobes to flex in a second direction includes a washer with a recessed passage allowing the lobes to flex in the second direction, and a planar surface preventing the lobes from flexing in the first direction.

48. The hemostasis valve combination of claim 47, wherein the washer is held by a hemostasis nut, and wherein the hemostasis nut may be manipulated to modify the sealing properties of the hemostasis valve.

\* \* \* \* \*